United States Patent
Zhou et al.

(10) Patent No.: US 11,248,208 B2
(45) Date of Patent: Feb. 15, 2022

(54) MULTIPLE ANTIGEN SPECIFIC CELL THERAPY METHODS

(71) Applicants: SYZ Cell Therapy Co., Guangdong (CN); HRYZ (SHENZHEN) BIOTECH CO., Guangdong (CN)

(72) Inventors: Xiangjun Zhou, Shenzhen (CN); Yifan Ma, Shenzhen (CN); Yanyan Han, Guangdong (CN); Jin Li, Shenzhen (CN); Longqing Tang, Shenzhen (CN); Junyun Liu, Shenzhen (CN); Dongyun Wu, Shenzhen (CN)

(73) Assignees: SYZ Cell Therapy Co., Guangdong (CN); HRYZ (Shenzhen) Biotech Co., Guangdong (CN)

( * ) Notice: Subject to any disclaimer, the term of this patent is extended or adjusted under 35 U.S.C. 154(b) by 0 days.

(21) Appl. No.: 17/043,613

(22) PCT Filed: Mar. 29, 2019

(86) PCT No.: PCT/CN2019/080535
§ 371 (c)(1),
(2) Date: Sep. 29, 2020

(87) PCT Pub. No.: WO2019/185041
PCT Pub. Date: Oct. 3, 2019

(65) Prior Publication Data
US 2021/0017495 A1  Jan. 21, 2021

(30) Foreign Application Priority Data
Mar. 30, 2018 (WO) ............... PCT/CN2018/081338

(51) Int. Cl.
C12N 5/0783 (2010.01)
A61K 35/17 (2015.01)
A61P 35/00 (2006.01)

(52) U.S. Cl.
CPC ............ *C12N 5/0638* (2013.01); *A61K 35/17* (2013.01); *A61P 35/00* (2018.01); *C12N 2501/02* (2013.01); *C12N 2501/2302* (2013.01); *C12N 2501/2307* (2013.01); *C12N 2501/2315* (2013.01); *C12N 2501/2321* (2013.01); *C12N 2501/24* (2013.01); *C12N 2501/50* (2013.01); *C12N 2501/515* (2013.01); *C12N 2501/999* (2013.01); *C12N 2502/1121* (2013.01)

(58) Field of Classification Search
CPC .............. C12N 5/0638; C12N 2501/02; C12N 2501/2302; C12N 2501/2307; C12N 2501/2315; C12N 2501/2321; C12N 2501/24; C12N 2501/50; C12N 2501/515; C12N 2501/999; C12N 2502/1121; A61P 35/00; A61K 35/17
See application file for complete search history.

(56) References Cited

U.S. PATENT DOCUMENTS

| | | |
|---|---|---|
| 5,388,946 A | 2/1995 | Baur |
| 5,580,859 A | 12/1996 | Felgner |
| 5,589,466 A | 12/1996 | Felgner |
| 5,976,546 A | 11/1999 | Laus |
| 6,080,409 A | 6/2000 | Laus |
| 6,210,662 B1 | 4/2001 | Laus |
| 6,326,193 B1 | 12/2001 | Liu |
| 7,999,092 B2 | 8/2011 | Han |
| 10,967,054 B2 | 4/2021 | Xiangjun et al. |
| 2003/0082806 A1 | 5/2003 | Berenson |
| 2005/0170503 A1 | 8/2005 | Falo, Jr. |
| 2006/0153821 A1 | 7/2006 | Falo, Jr. |
| 2012/0244620 A1 | 9/2012 | Boynton |
| 2012/0269860 A1 | 10/2012 | Karlsson-parra |
| 2015/0202291 A1 | 7/2015 | Bosch |
| 2016/0362658 A1 | 12/2016 | Leen |
| 2018/0078624 A1* | 3/2018 | Zhou ............... A61K 35/14 |
| 2019/0321478 A1 | 10/2019 | Alten et al. |
| 2021/0113676 A1 | 4/2021 | Zhou et al. |
| 2021/0154285 A1 | 5/2021 | Zhou et al. |
| 2021/0198341 A1 | 7/2021 | Zhou et al. |

FOREIGN PATENT DOCUMENTS

| | | |
|---|---|---|
| CN | 1353575 A | 6/2002 |
| CN | 1541113 A | 10/2004 |
| CN | 101336291 A | 12/2008 |
| CN | 102597222 A | 7/2012 |
| CN | 102625832 A | 8/2012 |
| CN | 104946588 A | 9/2015 |
| CN | 106645677 A | 5/2017 |
| CN | 107530392 A | 1/2018 |
| EP | 2215220 B1 | 1/2018 |
| JP | 2002539805 A | 11/2002 |
| JP | 2013502235 A | 1/2013 |
| WO | 2000057705 A1 | 10/2000 |
| WO | 2001029058 A1 | 4/2001 |
| WO | 2001029192 A2 | 4/2001 |
| WO | 2001096584 A2 | 12/2001 |
| WO | 2002000730 A2 | 1/2002 |
| WO | 2007067782 A2 | 6/2007 |
| WO | 2011028531 A1 | 3/2011 |
| WO | 2011053223 A1 | 5/2011 |

(Continued)

OTHER PUBLICATIONS

Brinke et al., Monophosphoryl lipid A plus IFNγ maturation of dendritic cells induces antigen-specific CD8+ cytotoxic T cells with high cytolytic potential. Cancer Immunology, Immunotherapy, vol. 59 (2010) pp. 1185-1195. (Year: 2010).*

Yoo et al., Efficacy of dendritic cells matured early with OK-432 (Picibanil®), prostaglandin E2 and interferon-α as a vaccine for a hormone refractory prostate cancer cell line. Journal of Korean Medical Science, vol. 25 (2010) pp. 1284-1290. (Year: 2010).*

(Continued)

*Primary Examiner* — Kara D Johnson
(74) *Attorney, Agent, or Firm* — Morrison & Foerster LLP

(57) ABSTRACT

The present invention provides methods of preparing a population of activated T cells by co-culturing T cells with dendritic cells loaded with a plurality of tumor antigen peptides. Also provided are methods of treating cancer in an individual using the activated T cells, pharmaceutical compositions and kits for cell-based cancer immunotherapy.

19 Claims, 14 Drawing Sheets

(56) References Cited

FOREIGN PATENT DOCUMENTS

| WO | 2015069770 A1 | 5/2015 |
|---|---|---|
| WO | 2016145578 A1 | 9/2016 |
| WO | 2016146035 A1 | 9/2016 |
| WO | 2016154628 A1 | 9/2016 |
| WO | 2019183924 A1 | 10/2019 |
| WO | 2019185041 A1 | 10/2019 |
| WO | 2019196087 A1 | 10/2019 |
| WO | 2019196088 A1 | 10/2019 |
| WO | 2019196923 A1 | 10/2019 |
| WO | 2019196924 A1 | 10/2019 |

OTHER PUBLICATIONS

Altadill, A. et al. (Oct. 2009; e-published on Apr. 16, 2009). "Liver Expression Of Matrix Metalloproteases And Their Inhibitors In Hepatocellular Carcinoma," Dig. Liver. Dis. 41(10):740-748.

Andreatta, M. (Feb. 15, 2016, e-pub. Oct. 29, 2015). "Gapped Sequence Alignment Using Artificial Neural Networks: Application To The MHC Class I System," Nielsen M. Bioinformatics 32(4):511-517.

Bernal, M. et al. (Sep. 2012, e-pub. Jul. 26, 2012). "Implication Of The β2-microglobulin Gene In The Generation Of Tumor Escape Phenotypes" Cancer Immunol. Immunother 61(9):1359-1371.

Boix, L. et al. (Jan. 1994). "C-Met mRNA Overexpression in Human Hepatocellular Carcinoma," Hepatology 19(1):88-91.

Boss (Boß) C.N. et al. (Jun. 1, 2007). "Identification and Characterization of T-Cell Epitopes Deduced from RGS5, a Novel Broadly Expressed Tumor Antigen," Clinical Cancer Research 13(11):3347-3355.

Boussiotis, V.A. (Dec. 4, 2014). "Somatic Mutations and Immunotherapy Outcome With CTLA-4 Blockade in Melanoma" N. Engl. J. Med. 371(23):2230-2232.

Bressac, B. et al. (Mar. 1, 1990). "Abnormal Structure and Expression of p53 Gene in Human Hepatocellular Carcinoma," Proc. Natl. Acad. Sci. U.S.A. 87(5):1973-1977.

Butterfield, L.H. et al. (May 1, 2006). "A Phase I/II Trial Testing Immunization of Hepatocellular Carcinoma Patients with Dendritic Cells Pulsed with Four α-Fetoprotein Peptides," Clinical Cancer Research 12(9):2817-2825.

Cha, E. et al. (May 28, 2014). "Improved Survival with T Cell Clonotype Stability after Anti-CTLA-4 Treatment in Cancer Patients," Sci. Transl. Med. 6(238):238r-270r.

Challa-Malladi, M. et al. (Dec. 13, 2011; e-published on Dec. 1, 2011). "Combined Genetic Inactivation of β2-Microglobulin and CD58 Reveals Frequent Escape from Immune Recognition in Diffuse Large B Cell Lymphoma," Cancer Cell 20(6):728-740.

Chapuis, A.G. et al. (Mar. 20, 2012; e-published on Mar. 5, 2012). "Transferred Melanoma-Specific CD8+ T Cells Persist, Mediate Tumor Regression, and Acquire Central Memory Phenotype," Proc Natl Acad Sci USA 109(12):4592-4597.

Cheever, M.A. et al. (Jun. 1, 2011; e-published on Apr. 6, 2011). "PROVENGE (Sipuleucel-T) In Prostate Cancer: The First FDA-Approved Therapeutic Cancer Vaccine," Clinical Cancer Research 17(11):3520-3526.

Chen, J.L. et al. (Jul. 15, 2000). "Identification of NY-ESO-1 Peptide Analogues Capable of Improved Stimulation of Tumor-Reactive CTL," The Journal of Immunology 165(2):948-955.

Chen, W. et al. (Mar./Apr. 2016). "Cancer Statistics in China, 2015" CA. Cancer. J. Clin. 66(2):115-132.

Chen, W. et al. (May 31, 2004). "Immune Responses of Dendritic Cells Pulsed With Myeloma Antigen," J Clin Intern Med 21(5): 331-333., (English Abstract Only).

Cicinnati, V.R. et al. (Dec. 15, 2006; e-published Sep. 22, 2006). "Increased Frequencies of CD8+ T Lymphocytes Recognizing Wild-Type P53-Derived Epitopes In Peripheral Blood Correlate with Presence Of Epitope Loss Tumor Variants in Patients with Hepatocellular Carcinoma," International Journal of Cancer 119(12):2851-2860.

Ciygan, V.N. (2004). "Anticancer Immune System," Reviews of Human Pharmacology and Drug Therapy 3(3):68-74. (English Translation of the Abstract Only).

Deng J. et al. (Jan. 31, 2007). "Anti-Tumor Immunity Induced By Activated Dendritic Cells with Tumor Antigen from HIFU-Treated Tumors," Chin J Cancer Prev. Treat 14(3):181-184. (English Translation of the Abstract Only).

European Supplementary Search Report dated Jul. 6, 2018 for EP Application No. 16764215.6 filed on Aug. 22, 2017, seven pages.

Garrido, F. et al. (Jul. 15, 2010). "'Hard' and 'Soft' Lesions Underlying the HLA Class I Alterations in Cancer Cells: Implications for Immunotherapy," International Journal of Cancer 127(2):249-256.

Gehring, A.J. et al. (Aug. 2009; e-published on Apr. 23, 2009). "Profile of Tumor Antigen-Specific CD8 T Cells in Patients with Hepatitis B Virus-Related Hepatocellular Carcinoma," Gastroenterology 137(2):682-690.

Gehring, A.J. et al. (Jul. 2011, e-pub. Nov. 23, 2010). Engineering Virus-Specific T cells that Target HBV Infected Hepatocytes and Hepatocellular Carcinoma Cell Lines. Journal of Hepatology 55:103-110.

Golub, T.R. et al. (1999). "Molecular Classification of Cancer: Class Discovery and Class Prediction by Gene Expression Monitoring," Science 286:531-537.

Grupp, S.A. et al. (Apr. 18, 2013, e-pub. Mar. 25, 2013). "Chimeric Antigen Receptor-Modified T Cells for Acute Lymphoid Leukemia," The New England Journal of Medicine 368:1509-1518.

Han, Y. (May 27, 2015). "Abstract 19: A Novel Cancer Immunotherapy with Multiple Tumor Antigen Activated Autologous T Cells for Hepatocellular Carcinoma," Cytotherapy 17(Suppl. S):S12, one page.

Holmes, I. et al. (2012, e-pub. Feb. 3, 2012). "Dirichlet Multinomial Mixtures: Generative Models for Microbial Metagenomics," PLoS One 7(2):e30126, 15 pages.

Hu, M. et al. (Sep. 2013; e-published on Jul. 19, 2013). "Over-Expression of Regulator of G Protein Signaling 5 Promotes Tumor Metastasis By Inducing Epithelial-Mesenchymal Transition in Hepatocellular Carcinoma Cells," Journal of Surgical Oncology 108(3):192-196.

Idenoue, S. et al. (Feb. 15, 2005). "A Potent Immunogenic General Cancer Vaccine That Targets Surviving, an Inhibitor of Apoptosis Proteins," Clinical Cancer Research 11(4):1474-1482.

International Preliminary Report on Patentability dated Oct. 15, 2020, for International Patent Application No. PCT/CN2018/081338 filed on Mar. 30, 2018, 8 pages.

International Preliminary Report on Patentability dated Oct. 15, 2020, for International Patent Application No. PCT/CN2019/080535 filed on Mar. 29, 2019, 7 pages.

International Preliminary Report on Patentability dated Sep. 28, 2017, for International Patent Application No. PCT/CN2015/074227 filed on Mar. 13, 2015, 8 pages.

International Preliminary Report on Patentability dated Sep. 28, 2017, for International Patent Application No. PCT/CN2016/076165 filed on Mar. 11, 2016, 8 pages.

International Search Report and Written Opinion dated Aug. 17, 2018 for International Patent Application No. PCT/CN2018/081338 filed on Mar. 30, 2018, 11 pages.

International Search Report and Written Opinion dated Jul. 4, 2019, for International Patent Application No. PCT/CN2019/080535 filed on Mar. 29, 2019, 10 pages.

International Search Report and Written Opinion dated Jun. 16, 2016 for International Patent Application No. PCT/CN2016/076165 filed on Mar. 11, 2016, 14 pages.

International Search Report dated Dec. 22, 2015 for International Patent Application No. PCT/CN2015/074227 filed on Mar. 13, 2015, 8 pages.

Ito, T. et al. (May 2000). "Survivin Promotes Cell Proliferation In Human Hepatocellular Carcinoma," Hepatology 31(5):1080-1085.

Jiao, B. et al. (2007). "Effect of Anti-Carcinoma of T Lymphocyte Activated By Dendritic Cells Modified By Large Intestine Tumor Antigen," Journal of Zhengzhou University, Medical Sciences (Department Of General Surgery the Affiliated Hospital, Zunyi Medical College) 42(6):1094-1096, 4 pages.

(56) References Cited

OTHER PUBLICATIONS

Kalos, M. et al. (Jul. 25, 2013). "Adoptive T Cell Transfer for Cancer Immunotherapy in the Era of Synthetic Biology," Immunity 39(1):49-60.
Kantoff, P.W. et al. (Jul. 29, 2010). "Sipuleucel-T immunotherapy for Castration-Resistant Prostate Cancer." The New England Journal of Medicine 363(5):411-422.
Kobayashi, E. et al. (Nov. 2013, e-pub. Oct. 13, 2013). "A New Cloning And Expression System Yields And Validates TCRs From Blood Lymphocytes Of Patients With Cancer Within 10 Days," Nature Medicine 19(11):1542-1546.
Komori, H. et al. (May 1, 2006). "Identification of HLA-A2- or HLA-A24-Restricted CTL Epitopes Possibly Useful for Glypican-3-Specific Immunotherapy of Hepatocellular Carcinoma," Clinical Cancer Research 12(9):2689-2697.
Koopman, L.A. et al. (Mar. 20, 2000). "Multiple Genetic Alterations Cause Frequent, and Heterogeneous Human Histocompatibility Leukocyte Antigen Class I Loss in Cervical Cancer," The Journal of Experimental Medicine 191(6):961-975.
Le, D.T. et al. (Jun. 25, 2015). "PD-1 Blockade In Tumors With Mismatch-Repair Deficiency," The New England Journal of Medicine 372(26):2509-2520.
Li, X. et al. (Aug. 2009). "Anti-tumor Effect of Cytotoxicity T Lymphocytes Activated by Dendritic Cells Loaded with Salivary Adenoid Cystic Carcinoma Antigen," Modern Oncology 17(8):1434-1436, (English Translation of the Abstract only).
Marshall, J.L. et al. (Feb. 1, 2005; e-published on Dec. 21, 2004). "Phase I Study of Sequential Vaccinations with Fowlpox-CEA(6D)-TRICOM Alone and Sequentially with Vaccinia-CEA(6D)-TRICOM, with and Without Granulocyte-Macrophage Colony-Stimulating Factor, in Patients with Carcinoembryonic Antigen-Expressing Carcinomas," Journal of Clinical Oncology 23(4):720-731.
Martin, B. et al. (2014; e-pub. Jun. 4, 2014). "Restoration of HCV-Specific CD8+ T Cell Function by Interferon-Free Therapy," Journal of Hepatology 61:538-543.
Melia, W. M. et al. (Aug. 15, 1981). "Plasma Carcinoembryonic Antigen in the Diagnosis and Management of Patients with Hepatocellular Carcinoma," Cancer 48(4):1004-1008.
Mizukoshi, E. et al. (Jun. 2006). "Cytotoxic T Cell Responses to Human Telomerase Reverse Transcriptase in Patients with Hepatocellular Carcinoma," Hepatology 43(6):1284-1294.
Nakamura, S. et al. (Aug. 2006). "Expression and Immunogenicity of NY-ESO-1 in Hepatocellular Carcinoma," Journal of Gastroenterology Hepatology 21(8):1281-1285.
Nishida, N. et al. (Jun. 15, 1994). "Amplification and Overexpression of the Cyclin D1 Gene in Aggressive Human Hepatocellular Carcinoma," Cancer Research 54(12):3107-3110.
Niu, H. et al. (Sep. 30, 2004). "Experimental and Clinical Research of Dendritic Cell and Syngeneic 1-12 Immunotherapy of Brain Glioma" The Chinese-German Journal of Clinical Oncology 3(3):147-150.
Okuyama, R. (Nov. 2013). "Immunological Responses to a Multi-Peptide Vaccine Targeting Cancer-Testis Antigens and VEGFRS in Advanced Pancreatic Cancer Patients," OncoImmunology 2(11):e27010-1-e27010-7.
Palucka, K. et al. (Jul. 25, 2013). "Dendritic-Cell-Based Therapeutic Cancer Vaccines," Immunity 39(1):38-48.
Porter, D.L. et al. (Aug. 25, 2011). "Chimeric Antigen Receptor-Modified T Cells in Chronic Lymphoid Leukemia," The New England Journal of Medicine 365:725-733.
Powell, Jr., D.J., et al. (Jan. 1, 2005; e-published on Dec. 20, 2004). "Transition of Late-Stage Effector T Cells to CD27+ CD28+ Tumor-Reactive Effector Memory T Cells in Humans After Adoptive Cell Transfer Therapy," Blood 105(1):241-250.
Qijun, Q. et al. (Apr. 2015). "Precision cancer immunotherapy: From theory to practice," Chin J Cancer Biother 22(2):151-158, (English Translation of the Abstract only).
Rapoport, A.P. et al. (Jan. 20, 2011; e-published on Oct. 28, 2010). "Combination Immunotherapy Using Adoptive T-Cell Transfer and Tumor Antigen Vaccination on the Basis of hTERT And Survivin After ASCT For Myeloma," Blood 117(3):788-797.
Restifo, N.P. et al. (Apr. 2012). "Adoptive Immunotherapy For Cancer: Harnessing The T Cell Response," Nat. Rev. Immunol. 12:269-281.
Robbins, P.F. et al. (Jun. 2013; e-published on May 5, 2013). "Mining Exomic Sequencing Data to Identify Mutated Antigens Recognized by Adoptively Transferred Tumor-Reactive T Cells." Nature Medicine 19(6):747-752.
Sawada, Y. et al. (2016; e-published on Jan. 19, 2016). "Phase II Study of the GPC3-Derived Peptide Vaccine as an Adjuvant Therapy for Hepatocellular Carcinoma Patients," OncoImmunology 5(5):e1129483-1-e1129483-8.
Sayem, M.A. et al. (Jan. 2016; e-published Aug. 31, 2015). "Identification of Glypican-3-Derived Long Peptides Activating Both CD8+ And CD4+ T Cells; Prolonged Overall Survival in Cancer Patients with Th Cell Response," OncoImmunology 5(1):e1062209-1-e1062209-14.
Schag, K. et al. (Jun. 1, 2004). "Identification of C-Met Oncogene as a Broadly Expressed Tumor-Associated Antigen Recognized by Cytotoxic T-Lymphocytes," Clinical Cancer Research 10(11):3658-3666.
Schuler, P. J. et al. (May 1, 2014; e-published on Feb. 28, 2014). "Phase I Dendritic Cell p53 Peptide Vaccine for Head and Neck Cancer," Clin. Cancer. Res. 20(9):2433-2444.
Schurich, A. et al. (May 2011). "Role of the Coinhibitory Receptor Cytotoxic T Lymphocyte Antigen-4 on Apoptosis-Prone CD8 T Cells in Persistent Hepatitis B Virus Infection," Hepatology 53(5):1494-1503.
Shukla, S.A. et al. (Nov. 2015; e-published on Sep. 15, 2015). "Comprehensive Analysis of Cancer-Associated Somatic Mutations in Class I HLA Genes," Nature Biotechnology 33(11):1152-1158.
Snyder, A. et al. (Dec. 4, 2014). "Genetic Basis for Clinical Response to CTLA-4 Blockade in Melanoma," The New England Journal of Medicine 371(23):2189-2199.
Suzuki, H. et al. (2013). "Multiple Therapeutic Peptide Vaccines Consisting of Combined Novel Cancer Testis Antigens and Anti-Angiogenic Peptides for Patients with Non-Small Cell Lung Cancer," Journal of Translational Medicine 11(97):1-10.
Topalian, S.L. et al. (Apr. 1, 2014, e-pub. Mar. 3, 2014). "Survival, Durable Tumor Remission, And Long-Term Safety In Patients With Advanced Melanoma Receiving Nivolumab," J. Clin. Oncol. 32(10):1020-1030.
Tran, E. et al. (May 9, 2014). "Cancer Immunotherapy Based on Mutation Specific CD4+ T Cells in a Patient with Epithelial Cancer," Science 344(6184):641-645.
Trimble, C. L. et al. (Nov. 21, 2015; e-published on Sep. 17, 2015). "Safety, Efficacy, and Immunogenicity of VGX-3100, A Therapeutic Synthetic DNA Vaccine Targeting Human Papillomavirus 16 and 18 E6 and E7 Proteins for Cervical Intraepithelial Neoplasia 2/3: A Randomised, Double-Blind, Placebo-Controlled Phase 2b Trial," The Lancet 386(10008):2078-2088, 22 pages.
U.S. Appl. No. 17/115,620, filed Dec. 8, 2020, by Xiangjun Zhou et al. (U.S. Patent Application is not submitted herewith pursuant to the waiver of 37 C.F.R § 1.98(a)(2)(iii) issued by the Office on Sep. 21, 2004.).
Umemoto, Y. et al. (Jan. 2015; e-published Feb. 8, 2014). "Prognostic Impact of Programmed Cell Death 1 Ligand 1 Expression in Human Leukocyte Antigen Class I-Positive Hepatocellular Carcinoma After Curative Hepatectomy," J Gastroenterol 50(1):65-75.
Van Allen, E.M. et al. (Oct. 9, 2015; e-published on Sep. 10, 2015). "Genomic Correlates of Response to CTLA-4 Blockade in Metastatic Melanoma," Science 350(6257):207-211, 13 pages.
Vigneron, N. et al. (Jul. 15, 2013). "Database of T Cell-Defined Human Tumor Antigens: the 2013 Update," Cancer Immunity 13:15, pp. 1-6.
Walter, S. et al. (Aug. 2012; e-published on Jul. 29, 2012). "Multipeptide Immune Response to Cancer Vaccine IMA901 After Single-Dose Cyclophosphamide Associates with Longer Patient Survival," Nature Medicine 18(8):1254-1261.

(56) References Cited

OTHER PUBLICATIONS

Wolchok, J.D. et al. (Nov. 27, 2014). "Cancer: Antitumor Immunity Gets a Boost," Nature 515(7528):496-498.
Written Opinion of the International Searching Authority dated Dec. 22, 2015 for International Patent Application No. PCT/CN2015/074227 filed on Mar. 13, 2015, 6 pages.
Yang, X. et al. (2009; e-published on Dec. 19, 2008). "An Introduction to Epitope Prediction Methods and Software" Rev. Med. Virol. 19(2):77-96.
Ye, Y. et al. (Sep. 30, 2007). "T Lymphocytes Activation by Dendritic Cells Loaded with the Tumor Antigen From 1-12 Breast Cancer Cells MCF-7," Chin J Cancer Prevtreat 14(17):1288-1289. (English Translation of the Abstract only).
Yoshida, T. et al. (Nov. 2015). "The History of the Research and Development of Human Anti-Human PD-1 Antibody Nivolumab as a new Immune Checkpoint Inhibitor," Medchem News 25(4):193-197. (English Translation of the Abstract Only).
Yuan, J. et al. (Dec. 23, 2008). "CTLA-4 Blockade Enhances Polyfunctional NY-ESO-1 Specific T Cell Responses in Metastatic Melanoma Patients with Clinical Benefit," Proceedings of the National Academy of Sciences USA 105(51):20410-20415.
Zhang, Hong-Mei, et al. (2009). "Experimental Study of Hepatoma Specific T-cell Response Induced by Dendritic Cells Loaded with Whole Cell Antigen in Different Strategies," China Cancer 18(3):226-229. (English Translation of the Abstract only).
Bissinger, A.L. et al. (2002). "Isolation and Expansion Of Human Cytomegalovirus-Specific Cytotoxic T Lymphocytes Using Interferon-Secretion Assay," Experimental Hematology 30:1178-1184.
Brosterhus, H. et al. (1999). "Enrichment and Detection Of Live Antigen-Specific CD4+ and CD8+ T Cells Based On Cytokine Secretion," Eur. J. Immunol. 29:4053-4059.
Buonaguro, L. et al. (Jan. 2011, e-pub. Nov. 3, 2010). "Translating Tumor Antigens into Cancer Vaccines," Clinical And Vaccine Immunology 18(1):23-34.
Cadhila, B. et al. (2017). "Enabling T Cell Recruitment to Tumours as a Strategy for Improving Adoptive T Cell Therapy," European Oncology & Haematology 13(1):66-73.
Datta, R. et al. (Nov. 1992). "Ionizing Radiation Activates Transcription of the EGR1 Gene Via CArG Elements," Proc. Natl. Acad. Sci. USA 89(1):10149-10153.
Davis, M.M. et al. (Apr. 1998). "Ligand Recognition By αβ T Cell Receptors," Annu Rev Immunol 16:(15):523-544.
Davis, M.M. et al. (Aug. 4, 1988). "T-Cell Antigen Receptor Genes and T-Cell Recognition," Nature 334:395-402.
Durgeau, A. et al. (Jan. 22, 2018). "Recent Advances in Targeting CD8 T-Cell Immunity for More Effective Cancer Immunotherapy," Front. Immunol. 22:1-14.
Edgar, R.C. (2004, e-pub. Mar. 19, 2004). "MUSCLE: Multiple Sequence Alignment With High Accuracy And High Throughput," Nucleic Acids Research 32(5):1792-1797.
Edgar, R.C. (Aug. 19, 2004). "MUSCLE: A Multiple Sequence Alignment Method With Reduced Time And Space Complexity," BMC Bioinformatics 5(113):1-19.
Gingrich, J.R. et al. (1998). "Inducible Gene Expression in the Nervous System of Transgenic Mice," Annual Rev. Neurosci. 21:377-405.
Han, Y. et al. (Mar. 22, 2017). "Dynamic and Specific Immune Responses Against Multiple Tumor Antigens Were Elicited In Patients With Hepatocellular Carcinoma After Cell-Based Immunotherapy," J. Transl. Med. 15(1):64, 13 pages.
Hollingsworth. R.E. et al. (2019, e-pub. Feb. 8, 2019). "Turning the Corner On Therapeutic Cancer Vaccines," Vaccines 4(7):1-10.
IMGT Scientific Chart (Mar. 25, 1997). "Definition of the FR-IMGT and CDR-IMG Regions," Located at http://www.imgt.org/IMGTScienlificChart/Nomenclaturel IMGT-FRCDRdefinition.html, last visited on Jan. 22, 2021, 2 pages.
International Search Report and Written Opinion of the International Searching Authority dated Jul. 17, 2019, for International Patent Application No. PCT/CN2019/082407, filed Apr. 12, 2019, 9 pages.
IPAR AnalyzerTM User's Guide. Brochure from iRepertoire Inc., V20200916, located at https:/lirepertoire.com/wp-content/uploads/2020102/20200916-iPair-demo_CRSedits.pclf last visited Jan. 22, 2021, 19 pages.
Kim, J.H. et al. (Apr. 2011). "High Cleavage Efficiency of a 2A Peptide Derived from Porcine Teschovirus-1 in Human Cell Lines, Zebrafish and Mice," PLOS One 6(4):e18556, 8 pages.
Larche, M. (2008). "Determining MHC Restriction of T-Cell Responses," No. 6 in Methods Mol. Med., Jones, M.G. et al. eds., Humana Press, Totowa, New Jersey, USA, 138:57-72, 27 pages.
Lefranc, M.-P. (1999). "The IMGT Unique Numbering For Immunoglobulins, T-Cell Receptors, and Ig-Like Domains," The Immunologist 7(4):132-136.
Lichtenegger, F. S. et al. (Feb. 27, 2018). "Targeting LAG-3 and IPD-1 to Enhance T Cell Activation by Antigen-Presenting Cells," Frontiers in Immunology 9:1-12.
Mader, S. et al. (Jun. 1993). "A Steroid-Inducible Promoter for the Controlled Overexpression of Cloned Genes in Eukaryotic Cells." Proc. Natl. Acad. Sci. USA 90:5603-5607.
Manome, Y. et al. (Oct. 1993). "Coinduction of c-jun Gene Expression and Internucleosomal DNA Fragmentation by Ionizing Radiation," Biochemistry 32(40):10607-10613.
Melero, I. et al. (Aug. 2015). "Evolving Synergistic Combinations Of Targeted Immunotherapies To Combat Cancer," Nature Review Cancer 15:457-472.
Spencer, D. M. et al. (Nov. 12, 1993). "Controlling Signal Transduction with Synthetic Ligands," Science 262(5136):1019-1024.
Ui-Tel, K. et al. (2000). "Sensitive Assay of RNA Interference in Drosophila and Chinese Hamster Cultured Cells Using Firefly Luciferase Gene As Target," FEBS Letters 479:79-82.
Zhang, L. et al. (Mar. 31, 2018). Progress in T Cell Receptor-Gene Engineered T Cell Immunotherapy for Solid Tumors, Tumor 38:256-263.

\* cited by examiner

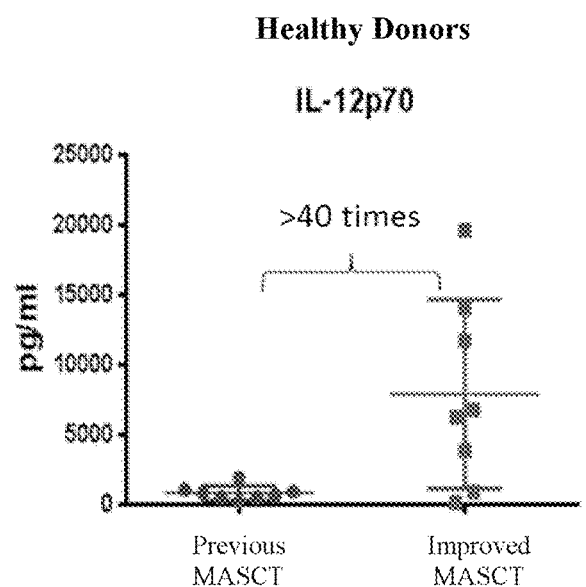
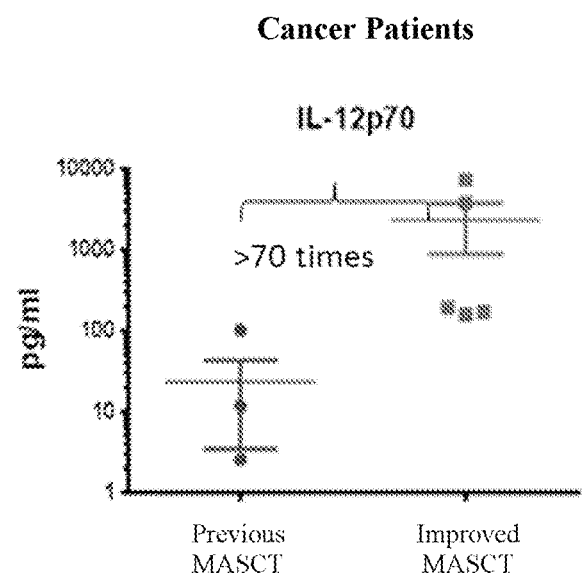
FIG. 6A
FIG. 6B
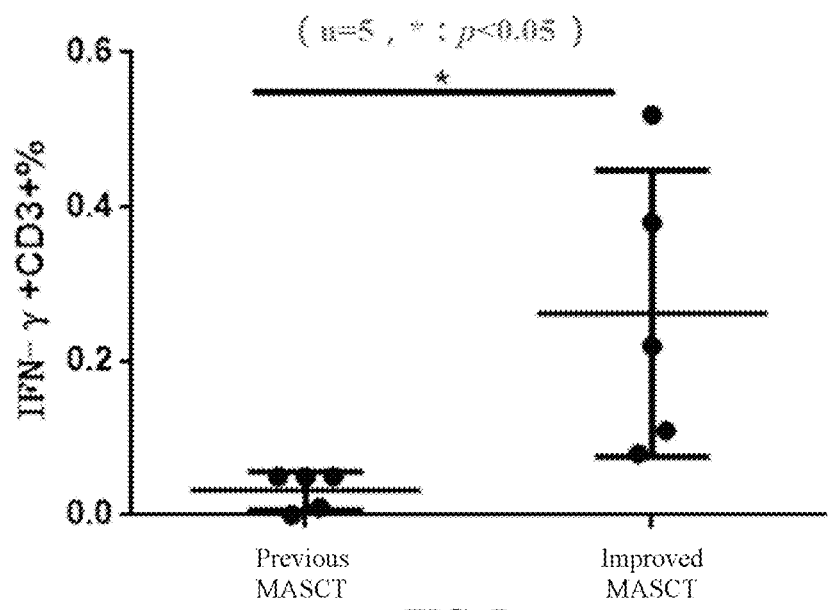
FIG. 7

| Patients | Cancer type | NeoMASCT treated times | Prediction algorithm | | | | | | | |
|---|---|---|---|---|---|---|---|---|---|---|
| | | | netMHC | | | | MASNEO | | | |
| | | | NeoAg number | Responding NeoAg number | Responding rate | | NeoAg number | Responding NeoAg number | Responding rate | |
| #1 | HCC | 10 | 3 | 2 | 66.7% | | 4 | 2 | 50% | |
| #2 | HCC | 5 | 4 | 4 | 100% | | 5 | 5 | 100% | |
| #3 | HCC | 3 | 2 | 1 | 50% | | 4 | 3 | 75% | |
| #4 | HCC | 3 | 2 | 0 | 0% | | 6 | 4 | 66.7% | |
| #5 | HCC | 4 | 5 | 2 | 40% | | 7 | 4 | 57.1% | |
| #6 | HCC | 4 | 5 | 3 | 60% | | 8 | 4 | 50% | |
| #7 | Endometrial cancer | 1 | | nd | | | 4 | 1 | 25% | |
| #8 | Colon cancer | 3 | | nd | | | 9 | 8 | 88.9% | |
| Summary | | | 21 | 12 | 57.1% | | 47 | 31 | 66% | |

HCC: hepatocellular carcinoma
nd: not done
NeoAg: neoantigen

FIG. 11

MULTIPLE ANTIGEN SPECIFIC CELL THERAPY METHODS

CROSS-REFERENCE TO RELATED APPLICATIONS

This application is a national stage application under 35 U.S.C. § 371 of International Application No. PCT/CN2019/080535, filed internationally on Mar. 29, 2019, which claims the priority benefit of International Patent Application No. PCT/CN2018/081338, filed Mar. 30, 2018, the contents of which are incorporated herein by reference in their entirety.

FIELD OF THE INVENTION

The present application relates to the field of cancer immunotherapy. More specifically, this application provides methods, compositions and kits for treating cancer in an individual using activated T cells.

BACKGROUND OF THE INVENTION

The human body has an elaborate immune system to defend itself against diseases. Unleashing the body's own immunity against cancer has been a long-standing ideal in oncology. Natural immune response against a tumor is elicited by tumor antigens. Antigen presenting cells (APCs), notably dendritic cells (DCs), can process and present the tumor antigens on their cell surface. Upon maturation, DCs loaded with tumor antigens can trigger T cell response, which involves cytotoxic T cells, helper T cells, and functionally distinct effecter and memory T cells against cancer cells expressing the tumor antigens. A particularly powerful type of T cell response involves production of cytotoxic T cells that can kill cancer cells by releasing cytokines, enzymes, and cytotoxins, or by inducing pro-apoptosis signaling cascades via cell-cell interactions.

Cell-based cancer immunotherapy seeks to treat cancer by administering to patients immunity-mediating cells prepared to target tumor antigens. FDA-approved PROVENGE® (sipuleucel-T) is a DC-based therapy, comprising exposing a patient's peripheral blood mononuclear cells (PBMCs) to a fusion protein comprising a tumor-derived antigen coupled to a cytokine, and then infusing the PBMCs, presumably containing activated DCs that can present the tumor-derived antigen to T cells, to the patient. See, U.S. Pat. No. 6,210,662. Adoptive T-cell therapy involves isolating tumor-infiltrating lymphocytes (TIL) from a patient's tumor, expanding the TILs ex vivo, and infusing the TILs back to the patient after depleting the patient's native non-myeloid lymphocytes. See, Restifo N P et al. (2012) *Nat. Rev. Immunol.* 12: 269-81. T cells with engineered T cell receptors (TCR-T) or chimeric antigen receptors (CAR-T) further expand the capacity of adoptive T-cell therapy methods by modifying the microenvironment of T cell-tumor interactions. Recently, a Multiple Antigen Specific Cell Therapy ("MASCT") method has been designed to harness the therapeutic capacity of both DCs and activated T cells in order to provide a safe, durable and customizable treatment to cancer patients. See, International Patent Application Publication No. WO2016145578A1.

The disclosures of all publications, patents, patent applications and published patent applications referred to herein are hereby incorporated herein by reference in their entirety.

BRIEF SUMMARY OF THE INVENTION

The present application provides methods of preparing activated T cells, and methods of treating cancer in an individual using the activated T cells.

One aspect of the present application provides a method of preparing a population of activated T cells, the method comprising: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising MPLA; and c) co-culturing the population of dendritic cells loaded with the plurality of tumor antigen peptides and a population of T cells, thereby obtaining the population of activated T cells. In some embodiments, step c) comprises co-culturing the population of dendritic cells loaded with the plurality of tumor antigen peptides and a population of T cells in a co-culture medium comprising an interleukin cocktail, an immune checkpoint inhibitor and an anti-CD3 antibody. In some embodiments, step c) comprises: co-culturing the population of dendritic cells loaded with the plurality of tumor antigen peptides and a population of T cells in an initial co-culture medium comprising a plurality of cytokines and an immune checkpoint inhibitor to provide a co-culture; and adding an anti-CD3 antibody to the co-culture, thereby obtaining the population of activated T cells. In some embodiments, the anti-CD3 antibody is added to the co-culture at about 3 to 7 days (such as about 5 days) after the co-culturing starts. In some embodiments, the population of dendritic cells loaded with the plurality of tumor antigen peptides and the population of T cells are co-cultured for at least about 10 days in the presence of the anti-CD3 antibody.

In some embodiments according to any one of the methods described above, the DC maturation medium comprises INFγ and MPLA. In some embodiments, the DC maturation medium further comprises PGE2. In some embodiments, the INFγ is present in the DC maturation medium at a concentration of at least about 100 IU/mL. In some embodiments, the MPLA is present in the DC maturation medium at a concentration of at least about 0.5 μg/mL. In some embodiments, the PGE2 is present in the DC maturation medium at a concentration of at least about 0.1 μg/mL.

One aspect of the present application provides a method of preparing a population of activated T cells, the method comprising: a) contacting a population of dendritic cells with a plurality of tumor antigen peptides to obtain a population of dendritic cells loaded with the plurality of tumor antigen peptides; b) co-culturing the population of dendritic cells loaded with the plurality of tumor antigen peptides and a population of T cells in an initial co-culture medium comprising a plurality of cytokines and an immune checkpoint inhibitor to provide a co-culture; and c) adding an anti-CD3 antibody to the co-culture at about 3 to 7 days (such as about 5 days) after the co-culturing starts, thereby obtaining the population of activated T cells. In some embodiments, the population of dendritic cells loaded with the plurality of tumor antigen peptides and the population of T cells are co-cultured for at least about 10 days in the presence of the anti-CD3 antibody. In some embodiments, step a) further comprises culturing the population of dendritic cells loaded with the plurality of tumor antigen peptides in a DC maturation medium comprising a toll-like receptor (TLR) agonist. In some embodiments, the TLR agonist is selected from the group consisting of MPLA, Poly I:C, resquimod, gardiquimod, and CL075.

In some embodiments according to any one of the methods described above, the plurality of cytokines comprises IL-2, IL-7, IL-15 and IL-21. In some embodiments, the IL-2 is present in the initial co-culture medium at a concentration of at least about 500 IU/mL.

In some embodiments according to any one of the methods described above, the immune checkpoint inhibitor is an anti-PD-1 antibody. In some embodiments, the anti-PD-1 antibody is present in the initial co-culture medium at a concentration of at least about 10 µg/mL.

In some embodiments according to any one of the methods described above, the population of T cells is present in a population of PBMCs.

In some embodiments according to any one of the methods described above, the population of dendritic cells is obtained by inducing differentiation of a population of monocytes from PBMCs.

In some embodiments according to any one of the methods described above, the population of dendritic cells and the population of T cells are obtained from the same individual. In some embodiments, the population of dendritic cells and the population of T cells are derived from PBMCs of the same individual.

In some embodiments according to any one of the methods described above, the plurality of tumor antigen peptides is a plurality of synthetic tumor antigen peptides. In some embodiments, the plurality of tumor antigen peptides is not obtained from a cell sample.

In some embodiments according to any one of the methods described above, the plurality of tumor antigen peptides comprises general tumor antigen peptide(s), cancer-type specific antigen peptide(s), and/or neoantigen peptides. In some embodiments, the plurality of tumor antigen peptides comprises one or more neoantigen peptides. In some embodiments, the plurality of tumor antigen peptides comprises (e.g., consists of) neoantigen peptides. In some embodiments, the plurality of tumor antigen peptides comprises at least about 5 (e.g., at least about 10, 20, 30, 40 or more) different tumor antigen peptides.

Also provided is an isolated population of activated T cells prepared using any one of the methods described above.

Further provided is a method of treating a cancer in an individual, comprising administering to the individual an effective amount of the activated T cells prepared using any one of the methods described above. In some embodiments, the method further comprises administering to the individual an effective amount of dendritic cells loaded with the plurality of tumor antigen peptides. In some embodiments, the population of dendritic cells and the population of T cells are obtained from the individual being treated. In some embodiments, the activated T cells are administered to the individual for at least three times. In some embodiments, the activated T cells are administered intravenously. In some embodiments, the dendritic cells loaded with the plurality of tumor antigen peptides are administered for at least three times. In some embodiments, the dendritic cells loaded with the plurality of tumor antigen peptides are administered subcutaneously, intradermally or intravenously. In some embodiments, the individual is a human individual. In some embodiments, the cancer is a solid cancer, such as hepatocellular carcinoma, gastric cancer, bladder cancer, soft tissue sarcoma, colorectal cancer, endometrial cancer, or lung cancer.

Further provided are pharmaceutical compositions, kits, and articles of manufacture for use in any one of the methods described above.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE DRAWINGS

FIG. 6A shows IL-2 secretion levels by induced antigen-loaded mature DCs from healthy donors using different DC preparation methods.

FIG. 6B shows IL-2 secretion levels by induced antigen-loaded mature DCs from cancer patients using different DC preparation methods.

FIG. 7 shows percentages of IFN-γ producing tumor antigen-specific T cells in co-cultures prepared using different methods.

FIG. 11 shows rates of specific T-cell response against neoantigen peptides in eight patients who responded to improved MASCT treatments using the neoantigen peptides ("neo-MASCT").

DETAILED DESCRIPTION OF THE INVENTION

Figure 1A:
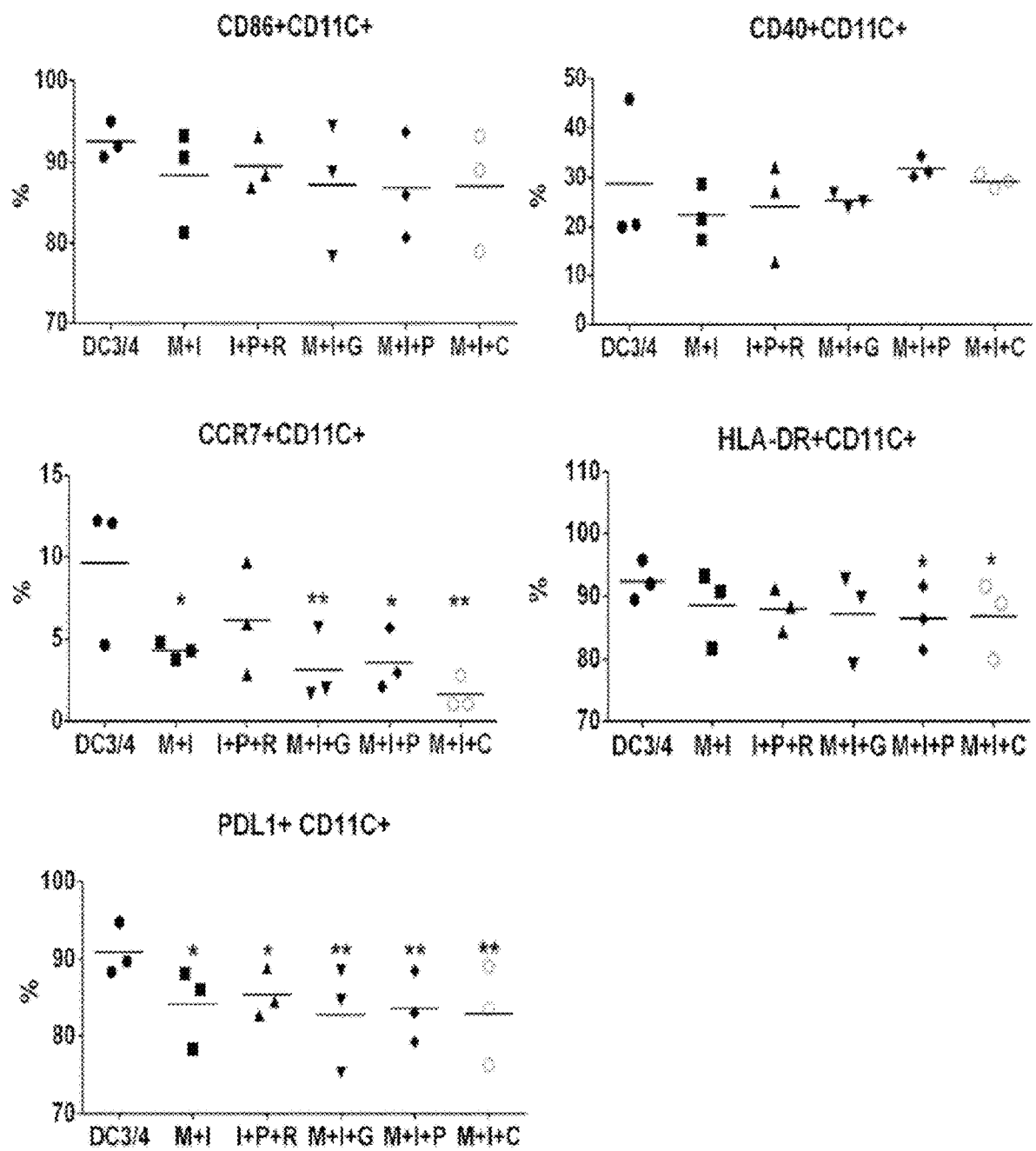
FIG. 1A shows expression levels of co-stimulatory molecules on mature DCs after incubation in DC maturation media containing various Toll-like receptors (TLRs) or combinations.

The present application provides improved methods of preparing activated T cells by co-culturing T cells with dendritic cells (DCs) loaded with a plurality of tumor antigen peptides. In some embodiments, the method uses a DC maturation medium comprising MPLA to induce maturation of antigen-loaded DCs, a co-culture medium comprising an interleukin cocktail and an immune checkpoint inhibitor (e.g., anti-PD-1 antibody) for co-culture of T cells with antigen-loaded DCs, and/or delayed addition of anti-CD3 antibody to the co-culture to provide activated T cells with an enhanced proportion of tumor antigen-specific T cells and a reduced proportion of immunosuppressive regulatory T cells (Tregs). Using the methods disclosed herein, IL-12 secretion by antigen-loaded mature DCs derived from cancer patients increased by about 70 times, while the percentage of tumor antigen-specific T cells in the co-culture increased by about 2-4 times compared to those using exemplary protocols of a previously reported Multiple Antigen Specific Cell Therapy ("MASCT" or "previous MASCT") method as disclosed in WO2016145578A1. Methods for treating cancer using the activated T cells described herein are referred to as the "improved MASCT" methods. The improved MASCT methods offer enhanced treatment efficacy and duration of response in patients having cancer, including solid cancer.

Accordingly, one aspect of the present application provides a method of preparing a population of activated T cells, the method comprising: a) contacting a population of dendritic cells with a plurality of tumor antigen peptides to obtain a population of dendritic cells loaded with the plurality of tumor antigen peptides; b) co-culturing the population of dendritic cells loaded with the plurality of tumor antigen peptides and a population of T cells in an initial co-culture medium comprising a plurality of cytokines and an immune checkpoint inhibitor to provide a co-culture, and c) adding an anti-CD3 antibody to the co-culture at about 3 to 7 days after the co-culturing starts, thereby obtaining the population of activated T cells.

Another aspect of the present application provides a method of preparing a population of activated T cells, the method comprising: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising MPLA; c) co-culturing the population of dendritic cells loaded with the plurality of tumor antigen peptides and a population of T cells, thereby obtaining the population of activated T cells.

Activated T cells prepared using the methods described herein, methods of treating cancer, compositions, kits, and articles of manufacture are also provided.

I. Definitions

Terms are used herein as generally used in the art, unless otherwise defined as follows.

As used herein, "treatment" or "treating" is an approach for obtaining beneficial or desired results including clinical results. For purposes of this invention, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread (e.g., metastasis) of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The terms "individual," "subject" and "patient" are used interchangeably herein to describe a mammal, including humans. An individual includes, but is not limited to, human, bovine, horse, feline, canine, rodent, or primate. In some embodiments, the individual is human. In some embodiments, an individual suffers from a disease, such as cancer. In some embodiments, the individual is in need of treatment.

As is understood in the art, an "effective amount" refers to an amount of a composition (e.g. antigen-loaded DCs, or activated T cells) sufficient to produce a desired therapeutic outcome (e.g., reducing the severity or duration of, stabilizing the severity of, or eliminating one or more symptoms of cancer). For therapeutic use, beneficial or desired results include, e.g., decreasing one or more symptoms resulting from the disease (biochemical, histologic and/or behavioral), including its complications and intermediate pathological phenotypes presented during development of the disease, increasing the quality of life of those suffering from the disease, decreasing the dose of other medications required to treat the disease, enhancing effect of another medication, delaying the progression of the disease, and/or prolonging survival of patients.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "combination therapy" means that a first agent is administered in conjunction with another agent. "In conjunction with" refers to administration of one treatment modality in addition to another treatment modality, such as administration of activated T cells described herein in addition to administration of another agent (such as an immune checkpoint inhibitor) to the same individual. As such, "in conjunction with" refers to administration of one treatment modality before, during, or after delivery of the other treatment modality to the individual. Such combinations are considered to be part of a single treatment regimen or regime.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to an individual without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein, the terms "cell", "cell line", and "cell culture" are used interchangeably and all such designations include progeny. It is understood that all progeny may not be precisely identical in DNA content, due to deliberate or inadvertent mutations. Variant progeny that have the same function or biological activity as the original cells are included.

The term "peptide" refers to a polymer of amino acids no more than about 100 amino acids (including fragments of a protein), which may be linear or branched, comprise modified amino acids, and/or be interrupted by non-amino acids. The term also encompasses an amino acid polymer that has been modified naturally or by intervention, including, for example, disulfide bond formation, glycosylation, lipidation, acetylation, phosphorylation, or any other manipulation or modification. Also included within this term are, for example, peptides containing one or more analogs of an amino acid (including, for example, unnatural amino acids, etc.), as well as other modifications known in the art. The peptides described herein may be naturally-occurring, i.e., obtained or derived from a natural source (e.g., blood) or synthesized (e.g., chemically synthesized or by synthesized by recombinant DNA techniques).

As used herein, "a plurality of tumor antigen peptides," "multiple tumor antigen peptides," "a pool of tumor antigen peptides" and "a tumor antigen peptides pool" are used interchangeably to refer to a combination of two or more tumor antigen peptides.

As used herein, "dendritic cells loaded with a plurality of tumor antigen peptides" and "antigen-loaded dendritic cells" are used interchangeably to refer to dendritic cells that have enhanced presentation of one or more tumor antigen peptides among the plurality of tumor antigen peptides.

As used herein, "activated T cells" refer to a population of monoclonal (e.g. encoding the same TCR) or polyclonal (e.g. with clones encoding different TCRs) T cells that have T cell receptors that recognize at least one tumor antigen peptide. Activated T cells may contain one or more subtypes of T cells, including, but not limited to, cytotoxic T cells, helper T cells, natural killer T cells, γδ T cells, regulatory T cells, and memory T cells.

As used herein, "immune checkpoint inhibitor" refers to an agent (including an antibody) that inhibits or blocks an inhibitory immune checkpoint molecule on an immune cell (such as T cell) or a tumor cell. "Immune checkpoint molecules" include molecules that turn up an immune signal (i.e., "co-stimulatory molecules"), or molecules that turn down an immune signal (i.e., "inhibitory immune checkpoint molecules") against a tumor cell.

The term "antibody" used herein is used in the broadest sense and specifically covers monoclonal antibodies (including full length monoclonal antibodies), multispecific antibodies (e.g., bispecific antibodies), and antibody fragments so long as they exhibit the desired biological activity.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

As use herein, the term "specifically binds to," "recognizes," "specifically recognizes," "targets," or is "specific for" refers to measurable and reproducible interactions such as binding between a target and an antibody, or a receptor and a ligand, or a receptor and an epitope/MHC complex, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to an antigen peptide (or an epitope) has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

The term "about X-Y" used herein has the same meaning as "about X to about Y."

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "an," and "the" include plural referents unless the context clearly dictates otherwise.

II. Methods of Preparing Activated T Cells

The present application provides methods of preparing activated T cells with enhanced proportion of tumor antigen-specific T cells and/or reduced proportion of immunosuppressive regulatory T cells (Tregs). In some embodiments, tumor antigen-specific T cells are activated T cells that elicit specific response to one or more of the tumor antigen peptides used to load the DCs. Methods of detecting and quantifying such tumor antigen-specific T cells are known in the art, including, but not limited to, detection by staining with pentamers and other multimers (such as dextramers), or detection of IFNγ-production by T cells after stimulation by tumor antigen peptides.

Accordingly, in some embodiments, there is provided a method of preparing a population of activated T cells, the method comprising: a) co-culturing a population of dendritic cells loaded with a plurality of tumor antigen peptides and a population of T cells in an initial co-culture medium comprising a plurality of cytokines and an immune checkpoint inhibitor to provide a co-culture; and c) adding an anti-CD3 antibody to the co-culture at about 3 to 7 days after the co-culturing starts, thereby obtaining the population of activated T cells. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 μg/mL. In some embodiments, the anti-CD3 antibody is added to the co-culture at about 5 days after the co-culturing starts. In some embodiments, the population of dendritic cells loaded with the plurality of tumor antigen peptides and the population of T cells are co-cultured for at least about 10 days in the presence of the anti-CD3 antibody. In some embodiments, the population of T cells is present in a population of PBMCs.

In some embodiments, there is provided a method of preparing a population of activated T cells, the method comprising: a) contacting a population of dendritic cells with a plurality of tumor antigen peptides to obtain a population of dendritic cells loaded with the plurality of tumor antigen peptides; b) co-culturing the population of dendritic cells loaded with the plurality of tumor antigen peptides and a population of T cells in an initial co-culture medium comprising a plurality of cytokines and an immune checkpoint inhibitor to provide a co-culture; and c) adding an anti-CD3 antibody to the co-culture at about 3 to 7 days after the co-culturing starts, thereby obtaining the population of activated T cells. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 μg/mL. In some embodiments, the anti-CD3 antibody is added to the co-culture at about 5 days after the co-culturing starts. In some embodiments, the population of dendritic cells loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of dendritic cells and the population of T cells are obtained from the same individual.

In some embodiments, there is provided a method of preparing a population of activated T cells, the method comprising: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising a toll-like receptor (TLR) agonist; (c) co-culturing the population of dendritic cells loaded with the plurality of tumor antigen peptides and a population of T cells in an initial co-culture medium comprising a plurality of cytokines and an immune checkpoint inhibitor to provide a co-culture; and d) adding an anti-CD3 antibody to the co-culture at about 3 to 7 days after the co-culturing starts, thereby obtaining the population of activated T cells. In some embodiments, the TLR agonist is selected from the group consisting of MPLA, Poly I:C, resquimod, gardiquimod, and CL075. In some embodiments, the DC maturation medium comprises PGE2. In some embodiments, the PGE2 is present in the DC maturation medium at a concentration of at least about 0.1 μg/mL. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 μg/mL. In some embodiments, the anti-CD3 antibody is added to the co-culture at about 5 days after the co-culturing starts. In some embodiments, the population of dendritic cells loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of dendritic cells and the population of T cells are obtained from the same individual.

In some embodiments, there is provided a method of preparing a population of activated T cells, the method comprising: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising MPLA; and c) co-culturing the population of dendritic cells loaded with the plurality of tumor antigen peptides and a population of T cells, thereby obtaining the population of activated T cells. In some embodiments, step c) comprises co-culturing the population of dendritic cells loaded with the plurality of tumor antigen peptides and a population of T cells in a co-culture medium comprising an interleukin cocktail, an immune checkpoint inhibitor and an anti-CD3 antibody. In some embodiments, the population of dendritic cells loaded with the plurality of tumor antigen peptides and the population of T cells are co-cultured for at least about 10 days in the presence of the anti-CD3 antibody. In some embodiments, the DC maturation medium comprises INFγ and MPLA. In some embodiments, the DC maturation medium further comprises PGE2. In some embodiments, the MPLA is present in the DC maturation medium at a concentration of at least about 0.5 μg/mL. In some embodiments, the INFγ is present in the DC maturation medium at a concentration of at least about 100 IU/mL. In some embodiments, the PGE2 is present in the DC maturation medium at a concentration of at least about 0.1 μg/mL. In some embodiments, the plurality of cytokines comprises IL-2, IL-7, IL-15 and IL-21. In some embodiments, the IL-2 is present in the co-culture medium at a concentration of at least about 500 IU/mL. In some embodiments, the immune checkpoint inhibitor is an anti-PD-1 antibody. In some embodiments, the anti-PD-1 antibody is present in the co-culture medium at a concentration of at least about 10 μg/mL. In some embodiments, the population of dendritic cells loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of dendritic cells and the population of T cells are obtained from the same individual.

In some embodiments, there is provided a method of preparing a population of activated T cells, the method comprising: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising MPLA; c) co-culturing the population of dendritic cells loaded with the plurality of tumor antigen peptides and a population of T cells in an initial co-culture medium comprising a plurality of cytokines and an immune checkpoint inhibitor to provide a co-culture; and d) adding an anti-CD3 antibody to the co-culture, thereby obtaining the population of activated T cells. In some embodiments, the anti-CD3 antibody is added to the co-culture when the co-culturing starts. In some embodiments, the anti-CD3 antibody is added to the co-culture after the co-culturing starts. In some embodiments, the DC maturation medium comprises INFγ and MPLA. In some embodiments, the DC maturation medium further comprises PGE2. In some embodiments, the MPLA is present in the DC maturation medium at a concentration of at least about 0.5 μg/mL. In some embodiments, the INFγ is present in the DC maturation medium at a concentration of at least about 100 IU/mL. In some embodiments, the PGE2 is present in the DC maturation medium at a concentration of at least about 0.1 μg/mL. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 μg/mL. In some embodiments, the population of dendritic cells loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of dendritic cells and the population of T cells are obtained from the same individual.

In some embodiments, there is provided a method of preparing a population of activated T cells, the method comprising: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising MPLA; c) co-culturing the population of dendritic cells loaded with the plurality of tumor antigen peptides and a population of T cells in an initial co-culture medium comprising a plurality of cytokines and an immune checkpoint inhibitor to provide a co-culture; and d) adding an anti-CD3 antibody to the co-culture at about 3 to 7 days after the co-culturing starts, thereby obtaining the population of activated T cells. In some embodiments, the DC maturation medium comprises INFγ and MPLA. In some embodiments, the DC maturation medium further comprises PGE2. In some embodiments, the MPLA is present in the DC maturation medium at a concentration of at least about 0.5 μg/mL. In some embodiments, the INFγ is present in the DC maturation medium at a concentration of at least about 100 IU/mL. In some embodiments, the PGE2 is present in the DC maturation medium at a concentration of at least about 0.1 μg/mL. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 µg/mL. In some embodiments, the anti-CD3 antibody is added to the co-culture at about 5 days after the co-culturing starts. In some embodiments, the population of dendritic cells loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of dendritic cells and the population of T cells are obtained from the same individual.

In some embodiments, there is provided a method of preparing a population of activated T cells, the method comprising: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising MPLA, INFγ and PGE2; c) co-culturing the population of dendritic cells loaded with the plurality of tumor antigen peptides and a population of T cells in an initial co-culture medium comprising a plurality of cytokines comprising IL-2, IL-7, IL-15 and IL-21 and an anti-PD-1 antibody to provide a co-culture; and d) adding an anti-CD3 antibody to the co-culture at about 3 to 7 days (e.g., about 5 days) after the co-culturing starts, thereby obtaining the population of activated T cells. In some embodiments, the MPLA is present in the DC maturation medium at a concentration of at least about 0.5 µg/mL. In some embodiments, the INFγ is present in the DC maturation medium at a concentration of at least about 100 IU/mL. In some embodiments, the PGE2 is present in the DC maturation medium at a concentration of at least about 0.1 µg/mL. In some embodiments, the IL-2 is present in the initial co-culture medium at a concentration of at least about 500 IU/mL. In some embodiments, the anti-PD-1 antibody is present in the initial co-culture medium at a concentration of at least about 10 µg/mL. In some embodiments, the population of dendritic cells loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of dendritic cells and the population of T cells are obtained from the same individual.

Also provided are isolated population of activated T cells and isolated population of dendritic cells loaded with a plurality of tumor antigen peptides prepared using any of the methods described herein.

Antigen Loading of Dendritic Cells

The methods of preparing tumor-antigen specific T cells use dendritic cells loaded with a plurality of tumor antigen peptides. In some embodiments, the dendritic cells loaded with a plurality of tumor antigen peptides are freshly prepared. The improved MASCT methods described herein may comprise one or more of the following steps: (1) obtaining PBMCs from an individual; (2) obtaining a population of monocytes from the PBMCs; (3) inducing differentiation of the population of monocytes into immature DCs; (4) contacting the immature DCs with a plurality of tumor antigen peptides to obtain a population of DCs loaded with the plurality of tumor antigen peptides; and (5) culturing the population of DCs loaded with the plurality of tumor antigen peptides in a DC maturation medium comprising a TLR agonist (such as MPLA).

In some embodiments, the dendritic cells loaded with a plurality of tumor antigen peptides are prepared by: (a) contacting a population of dendritic cells with a plurality of tumor antigen peptides to obtain a population of dendritic cells loaded with the plurality of tumor antigen peptides, and (b) culturing the population of dendritic cells loaded with the plurality of tumor antigen peptides in a DC maturation medium comprising a toll-like receptor (TLR) agonist. Exemplary TLR agonists include, but are not limited to, MPLA (monophosphoryl lipid A), Poly I:C, resquimod, gardiquimod, and CL075. Cytokines and other appropriate molecules, such as INFγ and PGE2 (prostaglandin E2) may be further included in the culturing media in the maturation step.

In some embodiments, the dendritic cells loaded with a plurality of tumor antigen peptides are prepared by: (a) contacting a population of dendritic cells with a plurality of tumor antigen peptides to obtain a population of dendritic cells loaded with the plurality of tumor antigen peptides, and (b) culturing the population of dendritic cells loaded with the plurality of tumor antigen peptides in a DC maturation medium comprising MPLA, INFγ and PGE2.

In some embodiments, the dendritic cells loaded with a plurality of tumor antigen peptides are prepared by: (a) inducing differentiation of a population of monocytes into immature DCs; (b) contacting a population of immature dendritic cells with a plurality of tumor antigen peptides to obtain a population of dendritic cells loaded with the plurality of tumor antigen peptides; and (c) culturing the population of dendritic cells loaded with the plurality of tumor antigen peptides in a DC maturation medium comprising MPLA, INFγ and PGE2. In some embodiments, the population of monocytes is obtained from PBMCs.

The DC maturation medium may comprise a suitable concentration of MPLA, INFγ and/or PGE2. In some embodiments, the DC maturation medium comprises MPLA at a concentration of at least about 0.5 µg/mL, such as at least about any one of 1, 2, 3, 4, 5, 6, 7, 8, 9, 10 or more µg/mL. In some embodiments, the DC maturation medium comprises MPLA at a concentration of any one of about 0.5-10, 1-5, 5-10, or 2.5-7.5 µg/mL. In some embodiments, the DC maturation medium comprises INFγ at a concentration of at least about 100 IU/mL, such as at least about any one of 150, 200, 250, 300, 400, 500, 600, 800, 1000 or more IU/mL. In some embodiments, the DC maturation medium comprises INFγ at a concentration of about any one of 100-1000, 100-250, 250-500, 500-1000, or 250-750 IU/mL. In some embodiments, the DC maturation medium comprises PGE2 at a concentration of at least about 0.1 µg/mL, such as at least about any one of 0.15, 0.2, 0.25, 0.3, 0.4, 0.5, or more µg/mL. In some embodiments, the DC maturation medium comprises PGE2 at a concentration of about any one of 0.1-0.5, 0.1-0.3, 0.25-0.5 or 0.2-0.4 µg/mL.

The immature dendritic cells loaded with a plurality of tumor antigen peptides may be induced by TLR agonists to mature for at least about any one of 1, 2, 3, 4, 5, 6, 7, 8, 9, 10, 15, or 20 days. In some embodiments, the dendritic cells loaded with a plurality of tumor antigen peptides are induced to mature for about 8 days.

In some embodiments, the antigen-loaded dendritic cells are mature dendritic cells that present one or more tumor antigen peptides of the plurality of tumor antigen peptides. The mature dendritic cells prepared by any of the methods described herein may present at least about any one of 1, 5, 10, 15, 20, 25, 30, 35, 40, 50, 60, 70, 80 or more tumor antigen peptides. Compared to naïve dendritic cells, or dendritic cells that have not been loaded with a plurality of tumor antigen peptides, the multiple-antigen loaded dendritic cells may have enhanced level of presentation for at least about any of 1, 5, 10, 15, 20, 25, 30, 35, 40, 50, 60, 70, 80 or more tumor antigen peptides. In some embodiments, the mature dendritic cells have enhanced level of presentation for more than 10 tumor antigen peptides. In some embodiments, the mature dendritic cells have enhanced level of presentation of about any of 1, 2, 3, 4, 5, 6, 7, 8, 9, 10, 11, 12, 13, 14, 15, or more tumor antigen peptides derived from proteins selected from the group consisting of hTERT, p53, Survivin, NY-ESO-1, CEA, CCND1, RGS5, MMP7, VEGFR1, VEGFR2, MUC1, HER2, MAGE-A1, MAGE-A3, CDCA1, WT1, KRAS, PARP4, MLL3, MTHFR, HBcAg, HBV polymerase, GPC3, SSX, and AFP.

In some embodiments, the antigen-loaded dendritic cells are prepared by pulsing the plurality of tumor antigen peptides into the population of dendritic cells, such as immature dendritic cells, or dendritic cells contained in or derived (such as differentiated) from the PBMCs. As known in the art, pulsing refers to a process of mixing cells, such as dendritic cells, with a solution containing antigen peptides, and optionally subsequently removing the antigen peptides from the mixture. The population of dendritic cells may be contacted with a plurality of tumor antigen peptides for seconds, minutes, or hours, such as about at least any one of 30 seconds, 1 minute, 5 minutes, 10 minutes, 15 minutes, 20 minutes, 30 minutes, 1 hour, 5 hours, 10 hours, 12 hours, 14 hours, 16 hours, 18 hours, 20 hours, 22 hours, 1 day, 2 days, 3 days, 4 days, 5 days, 6 days, one week, 10 days, or more. The concentration of each tumor antigen peptide used in the contacting step may be at least about any one of 0.1, 0.5, 1, 2, 3, 5, or 10 μg/mL. In some embodiments, the concentration of the tumor antigen peptides is about 0.1-200 μg/mL, including for example about any of 0.1-0.5, 0.5-1, 1-10, 10-50, 50-100, 100-150, or 150-200 μg/mL.

In some embodiments, the population of dendritic cells is contacted with the plurality of tumor antigen peptides in the presence of a composition that facilitates the uptake of the plurality of tumor antigen peptides by the dendritic cells. In some embodiments, compounds, materials or compositions may be included in a solution of the plurality of tumor antigen peptides to facilitate peptide uptake by the dendritic cells. Compounds, materials or compositions that facilitate the uptake of the plurality of tumor antigen peptides by the dendritic cells include, but are not limited to, lipid molecules and peptides with multiple positively charged amino acids. In some embodiments, more than about any of 50%, 60%, 70%, 80%, 90%, or 95% of the tumor antigen peptides are uptaken by the population of dendritic cells. In some embodiments, more than about any of 50%, 60%, 70%, 80%, 90%, or 95% of the dendritic cells in the population uptake at least one tumor antigen peptide.

Dendritic cells (such as immature dendritic cells) may be obtained from various sources, including autologous sources, i.e. from the individual receiving the treatment. A convenient source of dendritic cells is the PBMCs from the peripheral blood. For example, monocytes, a type of white blood cells, are abundant in PBMCs, comprising about 5-30% of total PBMCs. Monocytes can be induced to differentiate into dendritic cells, such as immature dendritic cells, using cytokines. In some embodiments, the immature dendritic cells are prepared by obtaining a population of PBMCs, obtaining a population of monocytes from the population of PBMCs, and contacting the population of monocytes with a plurality of cytokines to obtain a population of immature dendritic cells. Exemplary cytokines that may be used to induce differentiation of monocytes include, but are not limited to, GM-CSF and IL-4, with conditions (such as concentrations, temperature, $CO_2$ level etc.) known in the art.

The adherent fraction of PBMCs contains the majority of monocytes in PBMCs. In some embodiments, the monocytes from the adherent fraction of PBMCs are contacted with cytokines to obtain a population of immature dendritic cells. PBMCs can be conveniently obtained by centrifugation of a sample of peripheral blood, or using apheresis methods to collect from an individual. In some embodiments, the population of PBMCs is obtained by density gradient centrifugation of a sample of human peripheral blood. In some embodiments, the sample is from the individual that receives the multiple-antigen loaded dendritic cells, activated T cells, or other immunotherapeutic compositions prepared using the multiple-antigen loaded dendritic cells.

Further provided by the present application is an isolated population of dendritic cells prepared by any of the embodiments of the methods described herein. In some embodiments, the isolated population of dendritic cells is capable of eliciting MHC-restricted T cell response in vivo or ex vivo. In some embodiments, the MHC-restricted T cell response is mediated by both MHC class I and MHC class II molecules. In some embodiments, the isolated population of dendritic cells is capable of inducing differentiation and proliferation of tumor antigen-specific T cells.

Preparation of Activated T Cells

The methods described herein for preparing activated T cells comprise co-culturing a population of T cells with a population of dendritic cells loaded with a plurality of tumor antigen peptides. In some embodiments, the population of dendritic cells loaded with the plurality of tumor antigen peptides and the population of T cells are cultured in a co-culture medium comprising a plurality of cytokines, an immune checkpoint inhibitor, and an anti-CD3 antibody. In some embodiments, the activated T cells are prepared by: (a) co-culturing the population of dendritic cells loaded with a plurality of tumor antigen peptides and a population of T cells in an initial co-culture medium comprising a plurality of cytokines and an immune checkpoint inhibitor to provide a co-culture; and (b) adding an anti-CD3 antibody to the co-culture.

In some embodiments, the co-culture medium (including the initial co-culture medium) comprises a plurality of cytokines (also referred herein as "cytokine cocktail"). Exemplary cytokines include, but are not limited to, IL-2, IL-7, IL-15, IL-21 and the like. In some embodiments, the co-culture medium (including the initial co-culture medium) comprises IL-2, IL-7, IL-15 and IL-21. In some embodiments, each cytokine in the cytokine cocktail is present at a concentration of at least about any one of 0.1, 0.5, 1, 2, 3, 4, 5, 10, 15, 20, 25, 30, 40, 50 or higher ng/mL. In some embodiments, each cytokine in the cytokine cocktail is present at a concentration of about any one of 0.1-1, 1-5, 5-10, 10-20, 20-30, 1-30, 1-10, 30-50 or 1-50 ng/mL. In some embodiments, the IL-2 is present at least about any of 100, 200, 300, 400, 500, 600, 700, 800, 900, 1000, 1500, or 2000 IU/ml in the co-culture medium (including the initial co-culture medium). In some embodiments, the IL-2 is present at a concentration of about any one of 100-500, 500-1000, 1000-1500, 1500-2000, 100-2000, 500-1500, 100-1000 or 1000-2000 IU/ml. The cytokines may facilitate activation, maturation, and/or proliferation of the T cells, to prime T cells for later differentiation into effector T cells and memory T cells, and/or suppress the percentage of $T_{REG}$ in the population of activated T cells in the co-culture.

In some embodiments, the co-culture medium (including the initial co-culture medium) comprises one or more (such as any of 1, 2, 3, or more) immune checkpoint inhibitors. Any known immune checkpoint inhibitors may be used. In some embodiments, the immune checkpoint inhibitor is a natural or engineered ligand of an inhibitory immune checkpoint molecule, including, for example, ligands of CTLA-4 (e.g., B7.1, B7.2), ligands of TIM-3 (e.g., Galectin-9), ligands of A2a Receptor (e.g., adenosine, Regadenoson), ligands of LAG-3 (e.g., MHC class I or MHC class II molecules), ligands of BTLA (e.g., HVEM, B7-H4), ligands of KIR (e.g., MHC class I or MHC class II molecules), ligands of PD-1 (e.g., PD-L1, PD-L2), ligands of IDO (e.g., NKTR-218, Indoximod, NLG919), and ligands of CD47 (e.g., SIRP-alpha receptor).

The immune checkpoint inhibitors may be of any suitable molecular modality, including, but not limited to, small molecules, nucleic acids (such as DNA, RNAi, or aptamer), peptides, or proteins (such as antibodies).

In some embodiments, the immune checkpoint inhibitor is an antibody (such as antagonist antibody) that targets an inhibitory immune checkpoint protein selected from the group consisting of anti-CTLA-4 (e.g., Ipilimumab, Tremelimumab, KAHR-102), anti-TIM-3 (e.g., F38-2E2, ENUM005), anti-LAG-3 (e.g., BMS-986016, IMP701, IMP321, C9B7W), anti-KIR (e.g., Lirilumab and IPH2101), anti-PD-1 (e.g., Nivolumab, Pidilizumab, Pembrolizumab, BMS-936559, atezolizumab, Pembrolizumab, MK-3475, AMP-224, AMP-514, STI-A1110, TSR-042), anti-PD-L1 (e.g., KY-1003 (EP20120194977), MCLA-145, RG7446, BMS-936559, MEDI-4736, MSB0010718C, AUR-012, STI-A1010, PCT/US2001/020964, MPDL3280A, AMP-224, Dapirolizumab pegol (CDP-7657), MEDI-4920), anti-CD73 (e.g., AR-42 (OSU-HDAC42,HDAC-42,AR42,AR 42,OSU-HDAC 42,OSU-HDAC-42,NSC D736012,HDAC-42,HDAC 42,HDAC42,NSCD736012,NSC-D736012), MEDI-9447), anti-B7-H3 (e.g., MGA271, DS-5573a, 8H9), anti-CD47 (e.g., CC-90002, TTI-621, VLST-007), anti-BTLA, anti-VISTA, anti-A2aR, anti-B7-1, anti-B7-H4, anti-CD52 (such as alemtuzumab), anti-IL-10, anti-IL-35, and anti-TGF-f3 (such as Fresolumimab). In some embodiments, the antibody is a monoclonal antibody. In some embodiments, the antibody is a full-length antibody. In some embodiments, the antibody is an antigen-binding fragment selected from the group consisting of Fab, Fab', F(ab')$_2$, Fv, scFv, BiTE, nanobody, and other antigen-binding subsequences of the full length antibody or engineered combinations thereof. In some embodiments, the antibody is a human antibody, a humanized antibody, or a chimeric antibody. In some embodiments, the antibody is a bispecific or multi-specific antibody.

In some embodiments, the immune checkpoint inhibitor is an inhibitor of PD-1. In some embodiments, the immune checkpoint inhibitor is an anti-PD-1 antibody. Exemplary anti-PD-1 antibodies include, but are not limited to, Nivolumab, pembrolizumab, pidilizumab, BMS-936559, and atezolizumab, Pembrolizumab, MK-3475, AMP-224, AMP-514, STI-A1110, and TSR-042. In some embodiments, the immune checkpoint inhibitor is nivolumab (for example, OPDIVO®). In some embodiments, the immune checkpoint inhibitor is Pembrolizumab (for example, KEYTRUDA®). In some embodiments, the immune checkpoint inhibitor is SHR-1210. In some embodiments, the initial co-culture medium comprises IL-2, IL-7, IL-15, IL-21 and an anti-PD-1 antibody (e.g., SHR-1210).

A suitable concentration of the immune checkpoint inhibitor (e.g., anti-PD-1 antibody) in the co-culture medium (including the initial co-culture medium) include, but are not limited to, at least about any of 1, 2, 5, 10, 15, 20, 25 or more µg/mL. In some embodiments, the immune checkpoint inhibitor (e.g., anti-PD-1 antibody) is present in the co-culture medium (including the initial co-culture medium) is any one of about 1 µg/mL to about 10 µg/mL, about 10 µg/mL to about 20 µg/mL, about 1 µg/mL to about 25 µg/mL, or about 5 µg/mL to about 20 µg/mL.

The anti-CD3 antibody may be present in the co-culture at the time the co-culturing starts, or added to the co-culture after the co-culturing of the antigen-loaded dendritic cells and the T cells starts. In some embodiments, the anti-CD3 antibody is included in the co-culture medium (including the initial co-culture medium). In some embodiments, the initial co-culture medium does not comprise the anti-CD3 antibody. In some embodiments, the anti-CD3 antibody is added to the co-culture at about any one of 1, 2, 3, 4, 5, 6, 7, or more days after the co-culturing starts. In some embodiments, the anti-CD3 antibody is added to the co-culture at about any one of 1-7, 1-3, 3-5, 5-7 or 3-7 days after the co-culturing starts. In some embodiments, the anti-CD3 antibody is added to the co-culture at about 5 days after the co-culturing starts. Any suitable anti-CD3 antibody may be used, including, but not limited to OKT3.

In some embodiments, the population of T cells and the population of dendritic cells are derived from the same individual, such as an individual with a cancer (e.g., low to moderate grade cancer). In some embodiments, the population of T cells, the population of dendritic cells, or both is derived from autologous sources, i.e., from the individual that receives the activated T cells, the multiple-antigen loaded dendritic cells, or both.

In some embodiments, the population of T cells and the population of dendritic cells loaded with the plurality of tumor antigen peptides are co-cultured for at least about any one of 2, 4, 6, 8, 10, 12, 14, 16, 18, 20, 22, 24, 26, 28, or 30 days. In some embodiments, the population of T cells is co-cultured with the population of dendritic cells loaded with the plurality of tumor antigen peptides for about 7 days to about 21 days, such as about any one of 7-14, 14-21, 12-18, 10-16, 10, 14 , 16, 18 , or 21 days. In some embodiments, the population of T cells is co-cultured with the population of dendritic cells loaded with the plurality of tumor antigen peptides for about 10 days. In some embodiments, the population of T cells is co-cultured with the population of dendritic cells loaded with the plurality of tumor antigen peptides for about 14 days.

In some embodiments, the population of T cells and the population of dendritic cells loaded with the plurality of tumor antigen peptides are co-cultured in the presence of the anti-CD3 antibody for at least about any one of 1, 2, 3, 4, 5, 6, 7, 8, 9, 10, 12, 15, 20, or more days. In some embodiments, the population of T cells and the population of dendritic cells loaded with the plurality of tumor antigen peptides are co-cultured in the presence of the anti-CD3 antibody for about any one of 1-20, 5-15, 1-10, or 10-20 days.

The population of T cells used in any embodiment of the methods described herein may be derived from a variety of sources. A convenient source of T cells is from the PBMCs of the human peripheral blood. The population of T cells may be isolated from the PBMCs, or alternatively, a population of PBMCs enriched with T cells (such as by addition of T cell specific antibodies and cytokines) can be used in the co-culture. In some embodiments, the PBMCs are obtained by density gradient centrifugation of a sample of peripheral blood. In some embodiments, the population of T cells is present in the PBMCs. In some embodiments, PBMCs are used in the co-culture.

Further provided by the present application is an isolated population of activated T cells prepared by any embodiment of the methods described herein. Also provided herein is a co-culture useful for treating cancer in an individual, comprising a population of T cells and a population of dendritic cells loaded with a plurality of tumor antigen peptides. In some embodiments, the population of T cells and the population of dendritic cells loaded with the plurality of tumor antigen peptides are derived from the same individual, such as the individual being treated.

The isolated population of activated T cells and the co-culture described in this section may be used for treating cancer, such as solid caner. Immunotherapeutic compositions comprising the isolated population of activated T cells or the co-culture are useful for treating cancer, preventing tumor progression or metastasis, or reducing cancer immune escape are provided herein. The isolated population of activated T cells and the co-culture may also be used in the manufacture of a medicament for treating cancer, preventing tumor progression or metastasis, or reducing cancer immune escape.

It is intended that any of the steps and parameters described herein for preparing a population of dendritic cells loaded with a plurality of tumor antigen peptides or for preparing a population of activated T cells can be combined with any of the steps and parameters described herein for the improved MASCT method, as if each and every combination is individually described.

Plurality of Tumor Antigen Peptides

The methods described herein use a plurality of tumor antigen peptides to prepare dendritic cells and activated T cells that can trigger specific T cell response ex vivo and in vivo. In some embodiments, the plurality of tumor antigen peptides is a plurality of synthetic tumor antigen peptides. In some embodiments, the plurality of tumor antigen peptides is not obtained from a cell sample, such as a lysed cell composition.

In some embodiments, each tumor antigen peptide comprises at least about any one of 1, 2, 3, 4, 5, or 10 epitopes from a single protein antigen (including a neoantigen). In some embodiments, each tumor antigen peptide in the plurality of tumor antigen peptides comprises at least one epitope recognizable by a T cell receptor. In some embodiments, the plurality of tumor antigen peptides comprises at least one tumor antigen peptide that comprises at least 2 epitopes from a single protein antigen. The tumor antigen peptide can be a naturally derived peptide fragment from a protein antigen containing one or more epitopes, or an artificially designed peptide with one or more natural epitope sequences, wherein a linker peptide can optionally be placed in between adjacent epitope sequences. In some preferred embodiments, the epitopes contained in the same tumor antigen peptide are derived from the same protein antigen.

The tumor antigen peptide may contain at least one MHC-I epitope, at least one MHC-II epitope, or both MHC-I epitope(s) and MHC-II epitope(s). In some embodiments, the plurality of tumor antigen peptides comprises at least one peptide comprising an MHC-I epitope. In some embodiments, the plurality of tumor antigen peptides comprises at least one peptide comprising an MHC-II epitope. In some embodiments, at least one tumor antigen peptide in the plurality of tumor antigen peptides comprises both MHC-I and MHC-II epitopes.

Special design strategies can be applied to the sequence of the tumor antigen peptides (including neoantigen peptides) in order to optimize the immune response to dendritic cells loaded with the tumor antigen peptides. Typically, a peptide longer than the exact epitope peptide can increase uptake of the peptide into dendritic cells. In some embodiments, an MHC-I or MHC-II epitope sequence is extended at the N terminus or the C terminus or both termini according to the natural sequence of the protein harboring the epitope to obtain an extended sequence, wherein the extended sequence is amenable for presentation by both class I and class II HLA molecules, and by different subtypes of HLA molecules in different individuals. In some embodiments, the epitope sequence is extended at one or both termini by at least about any one of 1, 2, 3, 4, 5, 6, 7, 8, 9, 10, 12, 15, or 20 amino acid residues to generate the extended epitope. In some embodiments, the peptides comprising an MHC-I or MHC-II epitope further comprise additional amino acids flanking the epitope at the N-terminus, the C-terminus, or both. In some embodiments, each tumor antigen peptide in the plurality of tumor antigen peptides is at least about any one of 7, 8, 9, 10, 15, 20, 25, 30, 35, 40, 45, 50, 60, 70, 80, 90, or 100 amino acids long. Different tumor antigen peptides in the plurality of tumor antigen peptides may have the same length, or different lengths. In some embodiments, the plurality of tumor antigen peptides is each about 20-40 amino acids long.

In some embodiments, the amino acid sequences of one or more epitope peptides used to design a tumor antigen peptide in the present application are based on sequences known in the art or available in public databases, such as the Peptide Database (Vigneron N. et al. *Cancer Immunity*, 13:15 (2013)).

In some embodiments, the amino acid sequences of one or more epitope peptides are predicted based on the sequence of the antigen protein using a bioinformatics tool for T cell epitope prediction. Exemplary bioinformatics tools for T cell epitope prediction are known in the art, for example, see Yang X. and Yu X. (2009) "An introduction to epitope prediction methods and software" *Rev. Med. Virol.* 19(2): 77-96. In some embodiments, the sequence of the antigen protein is known in the art or available in public databases. In some embodiments, the sequence of the antigen protein is determined by sequencing a sample (such as a tumor sample) of the individual being treated.

The present application contemplates tumor antigen peptides derived from any tumor antigens and epitopes known in the art, including neoantigens and neoepitopes, or specially developed or predicted using bioinformatics tools by the inventors.

In some embodiments, the plurality of tumor antigen peptides comprises a first core group of general tumor antigen peptides. In some embodiments, the plurality of tumor antigen peptides further comprises a second group of cancer-type specific antigen peptides. In some embodiments, the plurality of tumor antigen peptides comprises one or more neoantigen peptides. In some embodiments, neoantigen peptides are cancer-type specific antigen peptides. In some embodiments, the plurality of tumor antigen peptides consists of the first core group of general tumor antigen peptides. In some embodiments, the plurality of tumor antigen peptides consists of the first core group of general tumor antigen peptides and the second group of cancer-type specific antigen peptides. In some embodiments, the plurality of tumor antigen peptides consists of neoantigen peptides. In some embodiments, the plurality of tumor antigen peptides comprises a first core group of general tumor antigen peptides and one or more neoantigen peptides. In some embodiments, the plurality of tumor antigen peptides comprises a first core group of general tumor antigen peptides, a second group of cancer-type specific antigen peptides, and one or more neoantigen peptides.

The first core group of general tumor antigen peptides is derived from tumor antigens commonly overexpressed by a variety of cancers of different types. Therefore, the first core group of general tumor antigen peptides is useful to prepare dendritic cells and/or activated T cells for treating individuals with different cancer types. For example, in some embodiments, the first core group of general tumor antigen peptides is useful for methods described herein for treating a variety of cancers, such as lung cancer, colon cancer, gastric cancer, prostate cancer, melanoma, lymphoma, pancreatic cancer, ovarian cancer, breast cancer, glioma, esophageal cancer, nasopharyngeal carcinoma, cervical cancer, renal carcinoma, or hepatocellular carcinoma. Exemplary tumor antigen peptides of the first core group include, but are not limited to, peptides derived from hTERT, p53, Survivin, NY-ESO-1, CEA, CCND1, MET, MUC1, Her2, MAGEA1, MAGEA3, WT-1, RGS5, MMP7, VEGFR (such as VEGFR1 and VEGFR2), and CDCA1. The first core group may comprise peptides derived from at least about any one of 1, 2, 5, 10, 15, 20, 25, 30, 40, 50, 60, 70, 80 or more tumor antigens. The first core group may comprise at least about any one of 1, 2, 5, 10, 15, 20, 25, 30, 40, 50, 60, 70, 80 or more general tumor antigen peptides. In some embodiments, the first core group comprises more than one general tumor antigen peptides. In some embodiments, the first core group comprises about 10 to about 20 general tumor antigen peptides.

The second group of cancer-type specific antigen peptides is derived from tumor antigens that are overexpressed only in one or a limited number of cancer types. Therefore, the second group of cancer-type specific antigen peptides is useful to prepare dendritic cells and/or activated T cells for treating individuals with a particular type of cancer. Exemplary cancer-type specific antigen peptides for treating hepatocellular carcinoma (HCC) include, but are not limited to, peptides derived from SSX, AFP, and GPC3. In some embodiments, one or more cancer -specific antigen peptide is a virus-specific antigen peptide derived from a virus that can induce cancer, or relates to cancer development in the individual when infecting the individual. In some embodiments, the virus-specific antigen peptide is specific to the subtype of the virus infecting the individual. Exemplary virus-specific antigen peptides for treating an HCC patient with concurrent infection of HBV include, but are not limited to, peptides derived from HBV core antigen (HBcAg), and HBV DNA polymerase. In some embodiments, the second group comprises virus-specific antigen peptides derived from HBV antigens, wherein the method is to treat hepatocellular carcinoma in an individual. In some embodiments, the second group comprises virus-specific antigen peptides derived from HPV antigens, wherein the method is to treat cervical cancer in an individual. In some embodiments, the second group comprises virus-specific antigen peptides derived from EBV antigens, wherein the method is to treat nasopharyngeal carcinoma in an individual. The second group of cancer-type specific antigen peptides may comprise peptides derived from at least about any one of 1, 2, 5, 10, 15, 20, 25, 30, 40, 50 or more cancer-type specific antigens. The second group of cancer-type specific antigen peptides may comprise at least about any one of 1, 2, 5, 10, 15, 20, 25, 30, 40, 50 or more cancer-type specific antigen peptides. In some embodiments, the second group comprises more than one cancer-type specific antigen peptides. In some embodiments, the second group comprises about 1 to about 10 cancer-type specific antigen peptides. In some embodiments, the type of cancer targeted by the cancer-type specific antigen peptides is selected from the group consisting essentially of hepatocellular carcinoma, cervical cancer, nasopharyngeal carcinoma, endometrial cancer, colorectal cancer, breast cancer, and lymphoma.

In some embodiments, the plurality of tumor antigen peptides comprises one or more (such as any of 1, 2, 3, 4, 5, 6, 7, 8, 9, 10 or more) neoantigen peptides. In some embodiments, the plurality of tumor antigen peptides consists of neoantigen peptides. In some embodiments, the plurality of tumor antigen peptides comprises neoantigen peptides and no general tumor antigen peptides. In some embodiments, the plurality of tumor antigen peptides comprises one or more general tumor antigen peptides and one or more neoantigen peptides. In some embodiments, the plurality of tumor antigen peptides comprises one or more general tumor antigen peptides, one or more cancer-type specific antigen peptides, and one or more neoantigen peptides. The neoantigen peptides are derived from neoantigens. Neoantigens are newly acquired and expressed antigens present in tumor cells of the individual, such as the individual being treated for cancer. In some embodiments, neoantigens are derived from mutant protein antigens that are only present in cancer cells, but absent in normal cells. Neoantigens may be uniquely present in the tumor cells (such as all tumor cells or a portion of tumor cells) of the individual being treated for cancer, or present in individuals having similar types of cancer as the individual being treated. In some embodiments, the neoantigen is a clonal neoantigen. In some embodiments, the neoantigen is a subclonal neoantigen. In some embodiments, the neoantigen is present in at least about any of 10%, 20%, 30%, 40%, 50%, 60%, 70%, 80%, 90%, 95% or more tumor cells in the individual. In some embodiments, the neoantigen peptide comprises an MHC-I restricted neoepitope. In some embodiments, the neoantigen peptide comprises an MHC-II restricted neoepitope. In some embodiments, the neoantigen peptide is designed to facilitate presentation of the neoepitope by both class I and class II MHC molecules, for example, by extending the neoepitope at both the N- and the C-termini. Exemplary neoantigen peptides include, but are not limited to, neoepitope derived from mutant KRAS (e.g., $KRAS^{G12A}$), PARP4 (e.g., $PARP4^{T1170I}$), MLL3 (e.g., $MLL3^{C988F}$), and MTHFR (e.g., $MTHFR^{A222V}$).

Neoantigen peptides can be selected based on the genetic profile of one or more tumor sites of the individual being treated, and neoantigens are not be expressed in normal tissues. In some embodiments, the genetic profile of the tumor sample comprises sequence information of the full genome. In some embodiments, the genetic profile of the tumor sample comprises sequence information of the exome. In some embodiments, the genetic profile of the tumor sample comprises sequence information of cancer-associated genes.

Neoantigen peptides suitable for use in the present application may be derived from any mutant proteins, such as those encoded by mutant cancer-associated genes, in the tumor cells. In some embodiments, the neoantigen peptide comprises a single neoepitope derived from a cancer-associated gene. In some embodiments, the neoantigen peptide comprises more than one (such as 2, 3, or more) neoepitope derived from a cancer-associated gene. In some embodiments, the neoantigen peptide comprises more than one (such as 2, 3, or more) neoepitope derived from more than one (such as 2, 3, or more) cancer-associated genes. In some embodiments, the plurality of tumor antigens comprises a plurality of neoantigen peptides derived from a single cancer-associated gene. In some embodiments, the plurality of tumor antigens comprises a plurality of neoantigen peptides derived from more than one (such as any of 2, 3, 4, 5, or more) cancer-associated genes.

Cancer-associated genes are genes that are overexpressed in cancer cells, but expressed at low levels in normal cells. Exemplary cancer-associated genes include, but are not limited to, ABL1, AKT1, AKT2, AKT3, ALK, ALOX12B, APC, AR, ARAF, ARID1A, ARID1B, ARID2, ASXL1, ATM, ATRX, AURKA, AURKB, AXL, B2M, BAP1, BCL2, BCL2L1, BCL2L12, BCL6, BCOR, BCORL1, BLM, BMPR1A, BRAF, BRCA1, BRCA2, BRD4, BRIP1, BUB1B, CADM2, CARD11, CBL, CBLB, CCND1, CCND2, CCND3, CCNE1, CD274, CD58, CD79B, CDC73, CDH1, CDK1, CDK2, CDK4, CDK5, CDK6, CDK9, CDKN1A, CDKN1B, CDKN1C, CDKN2A, CDKN2B, CDKN2C, CEBPA, CHEK2, CIITA, CREBBP, CRKL, CRLF2, CRTC1, CRTC2, CSF1R, CSF3R, CTNNB1, CUX1, CYLD, DDB2, DDR2, DEPDC5, DICER1, DIS3, DMD, DNMT3A, EED, EGFR, EP300, EPHA3, EPHA5, EPHA7, ERBB2, ERBB3, ERBB4, ERCC2, ERCC3, ERCC4, ERCC5, ESR1, ETV1, ETV4, ETV5, ETV6, EWSR1, EXT1, EXT2, EZH2, FAM46C, FANCA, FANCC, FANCD2, FANCE, FANCF, FANCG, FAS, FBXW7, FGFR1, FGFR2, FGFR3, FGFR4, FH, FKBP9, FLCN, FLT1, FLT3, FLT4, FUS, GATA3, GATA4, GATA6, GLI1, GLI2, GLI3, GNA11, GNAQ, GNAS, GNB2L1, GPC3, GSTM5, H3F3A, HNF1A, HRAS, ID3, IDH1, IDH2, IGF1R, IKZF1, IKZF3, INSIG1, JAK2, JAK3, KCNIP1, KDM5C, KDM6A, KDM6B, KDR, KEAP1, KIT, KRAS, LINC00894, LMO1, LMO2, LMO3, MAP2K1, MAP2K4, MAP3K1, MAPK1, MCL1, MDM2, MDM4, MECOM, MEF2B, MEN1, MET, MITF, MLH1, MLL (KMT2A), MLL2 (KTM2D), MPL, MSH2, MSH6, MTOR, MUTYH, MYB, MYBL1, MYC, MYCL1 (MYCL), MYCN, MYD88, NBN, NEGR1, NF1, NF2, NFE2L2, NFKBIA, NFKBIZ, NKX2-1, NOTCH1, NOTCH2, NPM1, NPRL2, NPRL3, NRAS, NTRK1, NTRK2, NTRK3, PALB2, PARK2, PAX5, PBRM1, PDCD1LG2, PDGFRA, PDGFRB, PHF6, PHOX2B, PIK3C2B, PIK3CA, PIK3R1, PIM1, PMS1, PMS2, PNRC1, PRAME, PRDM1, PRF1, PRKAR1A, PRKCI, PRKCZ, PRKDC, PRPF40B, PRPF8, PSMD13, PTCH1, PTEN, PTK2, PTPN11, PTPRD, QKI, RAD21, RAF1, RARA, RB1, RBL2, RECQL4, REL, RET, RFWD2, RHEB, RHPN2, ROS1, RPL26, RUNX1, SBDS, SDHA, SDHAF2, SDHB, SDHC, SDHD, SETBP1, SETD2, SF1, SF3B1, SH2B3, SLITRK6, SMAD2, SMAD4, SMARCA4, SMARCB1, SMC1A, SMC3, SMO, SOCS1, SOX2, SOX9, SQSTM1, SRC, SRSF2, STAG1, STAG2, STAT3, STAT6, STK11, SUFU, SUZ12, SYK, TCF3, TCF7L1, TCF7L2, TERC, TERT, TET2, TLR4, TNFAIP3, TP53, TSC1, TSC2, U2AF1, VHL, WRN, WT1, XPA, XPC, XPO1, ZNF217, ZNF708, and ZRSR2.

In some embodiments, the plurality of tumor antigen peptides comprises at least one (such as at least about any of 1, 2, 3, 4, 5, 6, 7, 8, 9, 10, 11, 12, 13, 14, 15 or more) tumor antigen peptide each comprising one or more epitopes encoded by a cancer-associated gene selected from the group consisting of hTERT, p53, Survivin, NY-ESO-1, CEA, CCND1, RGS5, MMP7, VEGFR1, VEGFR2, MUC1, HER2, MAGE-A1, MAGE-A3, CDCA1, WT1, KRAS, PARP4, MLL3, MTHFR, HBcAg, HBV polymerase, GPC3, SSX, and AFP. In some embodiments, the plurality of tumor antigen peptides comprises at least 10 tumor antigen peptides. In some embodiments, the plurality of tumor antigen peptides comprises tumor antigen peptides derived from hTERT, p53, Survivin, NY-ESO-1, CEA, CCND1, MUC1, Her2, MAGEA1, MAGEA3, WT-1, RGS5, VEGFR1, VEGFR2, and CDCA1.

In some embodiments, the plurality of tumor antigen peptides is present in a composition having at least about any one of 95%, 96%, 97%, 98%, 99%, 99.9% or higher percentage of tumor antigen peptides. In some embodiments, the purity of the plurality of tumor antigen peptides is at least about 98%. In some embodiments, the solubility of the plurality of tumor antigen peptides in the medium for pulsing the tumor antigen peptides into the dendritic cells is at least about any one of 80%, 85%, 90%, 95%, 98%, 99%, 99.9% or higher. In some embodiments, the plurality of tumor antigen peptides is about 100% soluble in the medium for pulsing the tumor antigen peptides into the dendritic cells.

III. Methods of Treatment

The present application provides cell-based immunotherapy methods of treating cancer in an individual, comprising administering to the individual an effective amount of activated T cells prepared using any one of the methods described in Section II. In some embodiments, the method further comprises administering to the individual an effective amount of dendritic cells loaded with a plurality of tumor antigen peptides.

In some embodiments, there is provided a method of treating a cancer (e.g., solid cancer) in an individual, comprising administering to the individual an effective amount of activated T cells, wherein the activated T cells are prepared by: (a) co-culturing a population of dendritic cells loaded with a plurality of tumor antigen peptides and a population of T cells in an initial co-culture medium comprising a plurality of cytokines and an immune checkpoint inhibitor to provide a co-culture; and b) adding an anti-CD3 antibody to the co-culture at about 3 to 7 days after the co-culturing starts, thereby obtaining the population of activated T cells. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 μg/mL. In some embodiments, the anti-CD3 antibody is added to the co-culture at about 5 days after the co-culturing starts. In some embodiments, the population of dendritic cells loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of dendritic cells and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of dendritic cells loaded with the plurality of tumor antigen peptides. In some embodiments, the dendritic cells loaded with the plurality of tumor antigen peptides are administered for at least three times. In some embodiments, the dendritic cells loaded with the plurality of tumor antigen peptides are administered subcutaneously, intradermally or intravenously. In some embodiments, the plurality of tumor antigen peptides comprises tumor antigen peptides derived from hTERT, p53, Survivin, NY-ESO-1, CEA, CCND1, MUC1, Her2, MAGEA1, MAGEA3, WT-1, RGS5, VEGFR1, VEGFR2, and CDCA1. In some embodiments, the cancer is a solid cancer selected from the group consisting of hepatocellular carcinoma, gastric cancer, bladder cancer, soft tissue sarcoma, colorectal cancer, endometrial cancer, and lung cancer.

In some embodiments, there is provided a method of treating a cancer (e.g., solid cancer) in an individual, comprising administering to the individual an effective amount of activated T cells, wherein the activated T cells are prepared by: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising MPLA; and c) co-culturing the population of dendritic cells loaded with the plurality of tumor antigen peptides and a population of T cells, thereby obtaining the population of activated T cells. In some embodiments, step c) comprises co-culturing the population of dendritic cells loaded with the plurality of tumor antigen peptides and a population of T cells in a co-culture medium comprising an interleukin cocktail, an immune checkpoint inhibitor and an anti-CD3 antibody. In some embodiments, the population of dendritic cells loaded with the plurality of tumor antigen peptides and the population of T cells are co-cultured for at least about 10 days in the presence of the anti-CD3 antibody. In some embodiments, the DC maturation medium comprises INFγ and MPLA. In some embodiments, the DC maturation medium further comprises PGE2. In some embodiments, the MPLA is present in the DC maturation medium at a concentration of at least about 0.5 µg/mL. In some embodiments, the INFγ is present in the DC maturation medium at a concentration of at least about 100 IU/mL. In some embodiments, the PGE2 is present in the DC maturation medium at a concentration of at least about 0.1 µg/mL. In some embodiments, the plurality of cytokines comprises IL-2, IL-7, IL-15 and IL-21. In some embodiments, the IL-2 is present in the co-culture medium at a concentration of at least about 500 IU/mL. In some embodiments, the immune checkpoint inhibitor is an anti-PD-1 antibody. In some embodiments, the anti-PD-1 antibody is present in the co-culture medium at a concentration of at least about 10 µg/mL. In some embodiments, the population of dendritic cells loaded with the plurality of tumor antigen peptides and the population of T cells are co-cultured for at least about 10 days in the presence of the anti-CD3 antibody. In some embodiments, the population of T cells is present in a population of PBMCs. n some embodiments, the population of dendritic cells and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of dendritic cells loaded with the plurality of tumor antigen peptides. In some embodiments, the dendritic cells loaded with the plurality of tumor antigen peptides are administered for at least three times. In some embodiments, the dendritic cells loaded with the plurality of tumor antigen peptides are administered subcutaneously, intradermally or intravenously. In some embodiments, the plurality of tumor antigen peptides comprises tumor antigen peptides derived from h LERT, p53, Survivin, NY-ESO-1, CEA, CCND1, MUC1, Her2, MAGEA1, MAGEA3, WT-1, RGS5, VEGFR1, VEGFR2, and CDCA1. In some embodiments, the cancer is a solid cancer selected from the group consisting of hepatocellular carcinoma, gastric cancer, bladder cancer, soft tissue sarcoma, colorectal cancer, endometrial cancer, and lung cancer.

In some embodiments, there is provided a method of treating a cancer (e.g., solid cancer) in an individual, comprising administering to the individual an effective amount of activated T cells, wherein the activated T cells are prepared by: a) contacting a population of dendritic cells with a plurality of tumor antigen peptides to obtain a population of dendritic cells loaded with the plurality of tumor antigen peptides; b) co-culturing the population of dendritic cells loaded with the plurality of tumor antigen peptides and a population of T cells in an initial co-culture medium comprising a plurality of cytokines and an immune checkpoint inhibitor to provide a co-culture; and c) adding an anti-CD3 antibody to the co-culture at about 3 to 7 days after the co-culturing starts, thereby obtaining the population of activated T cells. In some embodiments, step (a) further comprises culturing the population of dendritic cells loaded with the plurality of tumor antigen peptides in a DC maturation medium comprising a toll-like receptor (TLR) agonist. In some embodiments, the TLR agonist is selected from the group consisting of MPLA, Poly I: C, resquimod, gardiquimod, and CL075. In some embodiments, the DC maturation medium comprises PGE2. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 µg/mL. In some embodiments, the anti-CD3 antibody is added to the co-culture at about 5 days after the co-culturing starts. In some embodiments, the population of dendritic cells loaded with the plurality of tumor antigen peptides and the population of T cells are co-cultured for at least about 10 days in the presence of the anti-CD3 antibody. In some embodiments, the population of dendritic cells and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of dendritic cells loaded with the plurality of tumor antigen peptides. In some embodiments, the dendritic cells loaded with the plurality of tumor antigen peptides are administered for at least three times. In some embodiments, the dendritic cells loaded with the plurality of tumor antigen peptides are administered subcutaneously, intradermally or intravenously. In some embodiments, the plurality of tumor antigen peptides comprises tumor antigen peptides derived from hTERT, p53, Survivin, NY-ESO-1, CEA, CCND1, MUC1, Her2, MAGEA1, MAGEA3, WT-1, RGS5, VEGFR1, VEGFR2, and CDCA1. In some embodiments, the cancer is a solid cancer selected from the group consisting of hepatocellular carcinoma, gastric cancer, bladder cancer, soft tissue sarcoma, colorectal cancer, endometrial cancer, and lung cancer.

In some embodiments, there is provided a method of treating a cancer (e.g., solid cancer) in an individual, comprising administering to the individual an effective amount of activated T cells, wherein the activated T cells are prepared by: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising MPLA; c) co-culturing the population of dendritic cells loaded with the plurality of tumor antigen peptides and a population of T cells in an initial co-culture medium comprising a plurality of cytokines and an immune checkpoint inhibitor to provide a co-culture; and d) adding an anti-CD3 antibody to the co-culture, thereby obtaining the population of activated T cells. In some embodiments, the anti-CD3 antibody is added to the co-culture when the co-culturing starts. In some embodiments, the anti-CD3 antibody is added to the co-culture after the co-culturing starts. In some embodiments, the DC maturation medium comprises INFγ and MPLA. In some embodiments, the DC maturation medium further comprises PGE2. In some embodiments, the MPLA is present in the DC maturation medium at a concentration of at least about 0.5 µg/mL. In some embodiments, the INFγ is present in the DC maturation medium at a concentration of at least about 100 IU/mL. In some embodiments, the PGE2 is present in the DC maturation medium at a concentration of at least about 0.1 µg/mL. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 µg/mL. In some embodiments, the population of dendritic cells loaded with the plurality of tumor antigen peptides and the population of T cells are co-cultured for at least about 10 days in the presence of the anti-CD3 antibody. In some embodiments, the population of dendritic cells and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of dendritic cells loaded with the plurality of tumor antigen peptides. In some embodiments, the dendritic cells loaded with the plurality of tumor antigen peptides are administered for at least three times. In some embodiments, the dendritic cells loaded with the plurality of tumor antigen peptides are administered subcutaneously, intradermally or intravenously. In some embodiments, the plurality of tumor antigen peptides comprises tumor antigen peptides derived from hTERT, p53, Survivin, NY-ESO-1, CEA, CCND1, MUC1, Her2, MAGEA1, MAGEA3, WT-1, RGS5, VEGFR1, VEGFR2, and CDCA1. In some embodiments, the cancer is a solid cancer selected from the group consisting of hepatocellular carcinoma, gastric cancer, bladder cancer, soft tissue sarcoma, colorectal cancer, endometrial cancer, and lung cancer.

In some embodiments, there is provided a method of treating a cancer (e.g., solid cancer) in an individual, comprising administering to the individual an effective amount of activated T cells, wherein the activated T cells are prepared by: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising MPLA; c) co-culturing the population of dendritic cells loaded with the plurality of tumor antigen peptides and a population of T cells in an initial co-culture medium comprising a plurality of cytokines and an immune checkpoint inhibitor to provide a co-culture; and d) adding an anti-CD3 antibody to the co-culture at about 3 to 7 days after the co-culturing starts, thereby obtaining the population of activated T cells. In some embodiments, the DC maturation medium comprises INFγ and MPLA. In some embodiments, the DC maturation medium further comprises PGE2. In some embodiments, the MPLA is present in the DC maturation medium at a concentration of at least about 0.5 µg/mL. In some embodiments, the INFγ is present in the DC maturation medium at a concentration of at least about 100 IU/mL. In some embodiments, the PGE2 is present in the DC maturation medium at a concentration of at least about 0.1 µg/mL. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 µg/mL. In some embodiments, the anti-CD3 antibody is added to the co-culture at about 5 days after the co-culturing starts. In some embodiments, the population of dendritic cells loaded with the plurality of tumor antigen peptides and the population of T cells are co-cultured for at least about 10 days in the presence of the anti-CD3 antibody. In some embodiments, the population of dendritic cells and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of dendritic cells loaded with the plurality of tumor antigen peptides. In some embodiments, the dendritic cells loaded with the plurality of tumor antigen peptides are administered for at least three times. In some embodiments, the dendritic cells loaded with the plurality of tumor antigen peptides are administered subcutaneously, intradermally or intravenously. In some embodiments, the plurality of tumor antigen peptides comprises tumor antigen peptides derived from h IERT, p53, Survivin, NY-ESO-1, CEA, CCND1, MUC1, Her2, MAGEA1, MAGEA3, WT-1, RGS5, VEGFR1, VEGFR2, and CDCA1. In some embodiments, the cancer is a solid cancer selected from the group consisting of hepatocellular carcinoma, gastric cancer, bladder cancer, soft tissue sarcoma, colorectal cancer, endometrial cancer, and lung cancer.

In some embodiments, there is provided a method of treating a cancer (e.g., solid cancer) in an individual, comprising administering to the individual an effective amount of activated T cells, wherein the activated T cells are prepared by: a) contacting a population of dendritic cells with a plurality of tumor antigen peptides to obtain a population of dendritic cells loaded with the plurality of tumor antigen peptides; b) culturing the population of dendritic cells loaded with the plurality of tumor antigen peptides in a DC maturation medium comprising MPLA, INFγ and PGE2; c) co-culturing the population of dendritic cells loaded with the plurality of tumor antigen peptides and a population of T cells in an initial co-culture medium comprising a plurality of cytokines comprising IL-2, IL-7, IL-15 and IL-21 and an anti-PD-1 antibody to provide a co-culture; and d) adding an anti-CD3 antibody to the co-culture at about 3 to 7 days (e.g., about 5 days) after the co-culturing starts, thereby obtaining the population of activated T cells. In some embodiments, the MPLA is present in the DC maturation medium at a concentration of at least about 0.5 µg/mL. In some embodiments, the INFγ is present in the DC maturation medium at a concentration of at least about 100 IU/mL. In some embodiments, the PGE2 is present in the DC maturation medium at a concentration of at least about 0.1 µg/mL. In some embodiments, the IL-2 is present in the initial co-culture medium at a concentration of at least about 500 IU/mL. In some embodiments, the anti-PD-1 antibody is present in the initial co-culture medium at a concentration of at least about 10 µg/mL. In some embodiments, the population of dendritic cells loaded with the plurality of tumor antigen peptides and the population of T cells are co-cultured for at least about 10 days in the presence of the anti-CD3 antibody. In some embodiments, the population of dendritic cells and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of dendritic cells loaded with the plurality of tumor antigen peptides. In some embodiments, the dendritic cells loaded with the plurality of tumor antigen peptides are administered for at least three times. In some embodiments, the dendritic cells loaded with the plurality of tumor antigen peptides are administered subcutaneously, intradermally or intravenously. In some embodiments, the plurality of tumor antigen peptides comprises tumor antigen peptides derived from hTERT, p53, Survivin, NY-ESO-1, CEA, CCND1, MUC1, Her2, MAGEA1, MAGEA3, WT-1, RGS5, VEGFR1, VEGFR2, and CDCA1. In some embodiments, the cancer is a solid cancer selected from the group consisting of hepatocellular carcinoma, gastric cancer, bladder cancer, soft tissue sarcoma, colorectal cancer, endometrial cancer, and lung cancer.

In addition to the administration step(s), some embodiments of the improved MASCT method further comprise one or more of the following cell preparation steps: 1) obtaining PBMCs from the individual; 2) obtaining a population of DCs from the PBMCs (e.g., by inducing differentiation of a population of monocytes from the PBMCs); 3) obtaining a population of T cells from the PBMCs; 4) preparing a population of dendritic cells loaded with the plurality of tumor antigen peptides; 5) inducing maturation of the population of dendritic cells loaded with the plurality of tumor antigen peptides in a DC maturation medium; 6) co-culturing the population of dendritic cells loaded with the plurality of tumor antigen peptides and a population of T cells (including, for example, co-culturing the population of dendritic cells loaded with the plurality of tumor antigen peptides and a population of T cells in an initial co-culture medium; and adding an anti-CD3 antibody to the co-culture); and 8) co-culturing the population of dendritic cells loaded with the plurality of tumor antigen peptides and the population of T cells in the presence of the anti-CD3 antibody for at least about 10 days.

Thus, in some embodiments, there is provided a method of treating a cancer (e.g., solid cancer) in an individual, comprising: (a) obtaining a population of PBMCs from the individual; (b) obtaining a population of dendritic cells from the population of PBMCs; (c) contacting the population of dendritic cells with a plurality of tumor antigen peptides to obtain a population of dendritic cells loaded with the plurality of tumor antigen peptides; (d) culturing the population of dendritic cells loaded with the plurality of tumor antigen peptides in a DC maturation medium comprising MPLA, INFγ and PGE2; (e) optionally administering an effective amount of the dendritic cells loaded with the plurality of tumor antigen peptides to the individual; (f) obtaining a population of T cells from the PBMCs; (g) co-culturing the population of dendritic cells loaded with the plurality of tumor antigen peptides and the population of T cells in an initial co-culture medium comprising a plurality of cytokines comprising IL-2, IL-7, IL-15 and IL-21 and an anti-PD-1 antibody to provide a co-culture; (h) adding an anti-CD3 antibody to the co-culture at about 3 to 7 days (e.g., about 5 days) after the co-culturing starts to obtain a population of activated T cells; and (i) administering an effective amount of the activated T cells to the individual. In some embodiments, the MPLA is present in the DC maturation medium at a concentration of at least about 0.5 µg/mL. In some embodiments, the INFγ is present in the DC maturation medium at a concentration of at least about 100 IU/mL. In some embodiments, the PGE2 is present in the DC maturation medium at a concentration of at least about 0.1 µg/mL. In some embodiments, the IL-2 is present in the initial co-culture medium at a concentration of at least about 500 IU/mL. In some embodiments, the anti-PD-1 antibody is present in the initial co-culture medium at a concentration of at least about 10 µg/mL. In some embodiments, the population of dendritic cells loaded with the plurality of tumor antigen peptides and the population of T cells are co-cultured for at least about 10 days in the presence of the anti-CD3 antibody. In some embodiments, the activated T cells are administered to the individual for at least three times. In some embodiments, the activated T cells are administered intravenously. In some embodiments, the dendritic cells loaded with the plurality of tumor antigen peptides are administered for at least three times. In some embodiments, the dendritic cells loaded with the plurality of tumor antigen peptides are administered subcutaneously, intradermally or intravenously. In some embodiments, the plurality of tumor antigen peptides comprises tumor antigen peptides derived from hTERT, p53, Survivin, NY-ESO-1, CEA, CCND1, MUC1, Her2, MAGEA1, MAGEA3, WT-1, RGS5, VEGFR1, VEGFR2, and CDCA1. In some embodiments, the cancer is a solid cancer selected from the group consisting of hepatocellular carcinoma, gastric cancer, bladder cancer, soft tissue sarcoma, colorectal cancer, endometrial cancer, and lung cancer.

The methods described herein are suitable for treating various cancers, including liquid and solid cancers. In some embodiments, the cancer is selected from the group consisting of hepatocellular carcinoma, cervical cancer, bladder cancer, soft-tissue sarcoma, lung cancer, colorectal cancer, endometrial cancer, lymphoma, renal carcinoma, breast cancer, pancreatic cancer, gastric cancer, esophageal cancer, ovarian cancer, prostate cancer, nasopharyngeal carcinoma, melanoma, and brain cancer. The methods are applicable to cancers of all stages, including early stage, advanced stage and metastatic cancer.

In some embodiments, the method reduces the severity of one or more symptoms associated with the cancer by at least about any of 10%, 20%, 30%, 40%, 50%, 60%, 70%, 80%, 90%, 95% or 100% compared to the corresponding symptom in the same individual prior to treatment or compared to the corresponding symptom in other individuals not receiving the treatment method. In some embodiments, the method delays progression of the cancer.

In some embodiments, the method is for treating hepatocellular carcinoma (HCC). In some embodiments, the HCC is early stage HCC, non-metastatic HCC, primary HCC, advanced HCC, locally advanced HCC, metastatic HCC, HCC in remission, or recurrent HCC. In some embodiments, the HCC is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve all lobes of the liver and/or has spread to involve other organs (e.g., lung, lymph nodes, bone). In some embodiments, the HCC is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage W tumor (tumors with direct invasion of adjacent organs other than the gallbladder, or perforation of visceral peritoneum), N1 tumor (regional lymph node metastasis), or M1 tumor (distant metastasis). In some embodiments, the HCC is, according to AJCC (American Joint Commission on Cancer) staging criteria, stage T1, T2, T3, or T4 HCC. In some embodiments, the HCC is any one of liver cell carcinomas, fibrolamellar variants of HCC, and mixed hepatocellularcholangiocarcinomas. In some embodiments, the HCC is caused by Hepatitis B Virus (HBV) infection.

In some embodiments, the method is for treating lung cancer. In some embodiments, the lung cancer is a non-small cell lung cancer (NSCLC). Examples of NCSLC include, but are not limited to, large-cell carcinoma (e.g., large-cell neuroendocrine carcinoma, combined large-cell neuroendocrine carcinoma, basaloid carcinoma, lymphoepithelioma-like carcinoma, clear cell carcinoma, and large-cell carcinoma with rhabdoid phenotype), adenocarcinoma (e.g., acinar, papillary (e.g., bronchioloalveolar carcinoma, non-mucinous, mucinous, mixed mucinous and nonmucinous and indeterminate cell type), solid adenocarcinoma with mucin, adenocarcinoma with mixed subtypes, well-differentiated fetal adenocarcinoma, mucinous (colloid) adenocarcinoma, mucinous cystadenocarcinoma, signet ring adenocarcinoma, and clear cell adenocarcinoma), neuroendocrine lung tumors, and squamous cell carcinoma (e.g., papillary, clear cell, small cell, and basaloid). In some embodiments, the NSCLC may be, according to TNM classifications, a stage T tumor (primary tumor), a stage N tumor (regional lymph nodes), or a stage M tumor (distant metastasis).

In some embodiments, the lung cancer is a carcinoid (typical or atypical), adenosquamous carcinoma, cylindroma, or carcinoma of the salivary gland (e.g., adenoid cystic carcinoma or mucoepidermoid carcinoma). In some embodiments, the lung cancer is a carcinoma with pleomorphic, sarcomatoid, or sarcomatous elements (e.g., carcinomas with spindle and/or giant cells, spindle cell carcinoma, giant cell carcinoma, carcinosarcoma, or pulmonary blastoma). In some embodiments, the lung cancer is small cell lung cancer (SCLC; also called oat cell carcinoma). The small cell lung cancer may be limited-stage, extensive stage or recurrent small cell lung cancer. In some embodiments, the individual may be a human who has a gene, genetic mutation, or polymorphism suspected or shown to be associated with lung cancer (e.g., SASH1, LATS1, IGF2R, PARK2, KRAS, PTEN, Kras2, Krag, Pas1, ERCC1, XPD, IL8RA, EGFR, $\alpha_1$-AD, EPHX, MMP1, MMP2, MMP3, MMP12, IL1$\beta$, RAS, and/or AKT) or has one or more extra copies of a gene associated with lung cancer.

In some embodiments, the method is for treating cervical cancer. In some embodiments, the cervical cancer is early stage cervical cancer, non-metastatic cervical cancer, locally advanced cervical cancer, metastatic cervical cancer, cervical cancer in remission, unresectable cervical cancer, cervical cancer in an adjuvant setting, or cervical cancer in a neoadjuvant setting. In some embodiments, the cervical cancer is caused by human papillomavirus (HPV) infection. In some embodiments, the cervical cancer may be, according to TNM classifications, a stage T tumor (primary tumor), a stage N tumor (regional lymph nodes), or a stage M tumor (distant metastasis). In some embodiments, the cervical cancer is any of stage 0, stage I (Tis, N0, M0), stage IA (T1 a, N0, M0), stage IB (T1b, N0, M0), stage IIA (T2a, N0, M0), stage IIB (T2b, N0, M0), stage IIIA (T3a, N0, M0), stage IIIB (T3b, N0, M0, or T1-3, N1, M0) stage IVA (T4, N0, M0), or stage IVB (T1-T3, N0-N1, M1) cervical cancer. In some embodiments, the cervical cancer is cervical squamous cell carcinoma, cervical adenonocarcinoma, or adenosquamous carcinoma.

In some embodiments, the method is for treating breast cancer. In some embodiments, the breast cancer is early stage breast cancer, non-metastatic breast cancer, locally advanced breast cancer, metastatic breast cancer, hormone receptor positive metastatic breast cancer, breast cancer in remission, breast cancer in an adjuvant setting, ductal carcinoma in situ (DCIS), invasive ductal carcinoma (IDC), or breast cancer in a neoadjuvant setting. In some embodiments, the breast cancer is hormone receptor positive metastatic breast cancer. In some embodiments, the breast cancer (which may be HER2 positive or HER2 negative) is advanced breast cancer. In some embodiments, the breast cancer is ductal carcinoma in situ. In some embodiments, the individual may be a human who has a gene, genetic mutation, or polymorphism associated with breast cancer (e.g., BRCA1, BRCA2, ATM, CHEK2, RAD51, AR, DIRAS3, ERBB2, TP53, AKT, PTEN, and/or PI3K) or has one or more extra copies of a gene (e.g., one or more extra copies of the HER2 gene) associated with breast cancer.

In some embodiments, the method is for treating pancreatic cancer. In some embodiments, the pancreatic cancer includes, but is not limited to, serous microcystic adenoma, intraductal papillary mucinous neoplasm, mucinous cystic neoplasm, solid pseudopapillary neoplasm, pancreatic adenocarcinoma, pancreatic ductal carcinoma, or pancreatoblastoma. In some embodiments, the pancreatic cancer is any of early stage pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, recurrent pancreatic cancer, pancreatic cancer in an adjuvant setting, or pancreatic cancer in a neoadjuvant setting.

In some embodiments, the method is for treating ovarian cancer. In some embodiments, the ovarian cancer is ovarian epithelial cancer. Exemplary ovarian epithelial cancer histological classifications include: serous cystomas (e.g., serous benign cystadenomas, serous cystadenomas with proliferating activity of the epithelial cells and nuclear abnormalities but with no infiltrative destructive growth, or serous cystadenocarcinomas), mucinous cystomas (e.g., mucinous benign cystadenomas, mucinous cystadenomas with proliferating activity of the epithelial cells and nuclear abnormalities but with no infiltrative destructive growth, or mucinous cystadenocarcinomas), endometrioid tumors (e.g., endometrioid benign cysts, endometrioid tumors with proliferating activity of the epithelial cells and nuclear abnormalities but with no infiltrative destructive growth, or endometrioid adenocarcinomas), clear cell (mesonephroid) tumors (e.g., benign clear cell tumors, clear cell tumors with proliferating activity of the epithelial cells and nuclear abnormalities but with no infiltrative destructive growth, or clear cell cystadenocarcinomas), unclassified tumors that cannot be allotted to one of the above groups, or other malignant tumors. In various embodiments, the ovarian epithelial cancer is stage I (e.g., stage IA, IB, or IC), stage II (e.g., stage IIA, IIB, or IIC), stage III (e.g., stage IIIA, IIIB, or IIIC), or stage IV. In some embodiments, the individual may be a human who has a gene, genetic mutation, or polymorphism associated with ovarian cancer (e.g., BRCA1 or BRCA2) or has one or more extra copies of a gene associated with ovarian cancer (e.g., one or more extra copies of the HER2 gene). In some embodiments, the ovarian cancer is an ovarian germ cell tumor. Exemplary histologic subtypes include dysgerminomas or other germ cell tumors (e.g., endodermal sinus tumors such as hepatoid or intestinal tumors, embryonal carcinomas, olyembryomas, choriocarcinomas, teratomas, or mixed form tumors). Exemplary teratomas are immature teratomas, mature teratomas, solid teratomas, and cystic teratomas (e.g., dermoid cysts such as mature cystic teratomas, and dermoid cysts with malignant transformation). Some teratomas are monodermal and highly specialized, such as struma ovarii, carcinoid, struma ovarii and carcinoid, or others (e.g., malignant neuroectodermal and ependymomas). In some embodiments, the ovarian germ cell tumor is stage I (e.g., stage IA, IB, or IC), stage II (e.g., stage IIA, IIB, or IIC), stage III (e.g., stage IIIA, IIIB, or IIIC), or stage IV.

The improved MASCT methods described herein in some embodiments are not applicable to patients with cancers of T-cell origin, such as T-cell lymphoma.

Several viruses are related to cancer in humans. For example, Hepatitis B virus (HBV) can cause chronic infection of the liver, increasing an individual's chance of liver cancer, or hepatocellular carcinoma (HCC). Human papilloma viruses (HPVs) are a group of more than 150 related viruses, which cause papilloma, or warts, when they infect and grow in skin or mucous membranes, such as the mouth, throat, or vagina. Several types of HPV (including types 16, 18, 31, 33, 35, 39, 45, 51, 52, 56, 58, 59 and 6) are known to cause cervical cancer. HPVs also play a role in inducing or causing other cancers of the genitalia, and are linked to some cancers of the mouth and throat. Epstein-Barr virus (EBV) is a type of herpes virus, which chronically infects and remains latent in B lymphocytes. EBV infection increases an individual's risk of developing nasopharyngeal carcinoma and certain types of fast-growing lymphomas such as Burkitt lymphoma. EBV is also linked to Hodgkin lymphoma and some cases of gastric cancer. In addition to causing cancer or increasing risk of developing cancer, viral infections, such as infections with HBV, HPV, and EBV, may result in damage to tissues or organs, which can increase the disease burden of an individual suffering from a cancer, and contribute to cancer progression. It is known in the art that the human body can be induced to mount effective and specific immune response, including cytotoxic T cell response, against several cancer-related viruses, such as HBV, HPV and EBV, including their various subtypes. Therefore, in some embodiments, there is provided a method of treating a virus-related cancer in an individual, comprising administering to the individual an effective amount of activated T cells, wherein the activated T cells are prepared by co-culturing a population of T cells with a population of dendritic cells loaded with a plurality of tumor antigen peptides, wherein the plurality of tumor antigen peptides comprise one or more tumor antigen peptides derived from the virus. In some embodiments, the cancer is HBV-related hepatocellular carcinoma, HPV-related cervical cancer, or EBV-related nasopharyngeal carcinoma.

The methods described herein can be used for any one or more of the following purposes: alleviating one or more symptoms of cancer, delaying progression of cancer, shrinking cancer tumor size, disrupting (such as destroying) cancer stroma, inhibiting cancer tumor growth, prolonging overall survival, prolonging disease-free survival, prolonging time to cancer disease progression, preventing or delaying cancer tumor metastasis, reducing (such as eradiating) preexisting cancer tumor metastasis, reducing incidence or burden of preexisting cancer tumor metastasis, preventing recurrence of cancer, and/or improving clinical benefit of cancer.

In some embodiments, there is provided a method of inhibiting cancer cell proliferation (such as tumor growth) in an individual, comprising administering to the individual an effective amount of activated T cells. In some embodiments, the method further comprises administering to the individual an effective amount of dendritic cells loaded with a plurality of tumor antigen peptides. In some embodiments, at least about 10% (including for example at least about any of 20%, 30%, 40%, 60%, 70%, 80%, 90%, or 100%) cell proliferation is inhibited.

In some embodiments, there is provided a method of inhibiting tumor metastasis in an individual, comprising administering to the individual an effective amount of activated T cells. In some embodiments, the method further comprises administering to the individual an effective amount of dendritic cells loaded with a plurality of tumor antigen peptides. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided.

In some embodiments, there is provided a method of reducing tumor size in an individual, comprising administering to the individual an effective amount of activated T cells. In some embodiments, the method further comprises administering to the individual an effective amount of dendritic cells loaded with a plurality of tumor antigen peptides. In some embodiments, the tumor size is reduced at least about 10% (including for example at least about any of 20%, 30%, 40%, 60%, 70%, 80%, 90%, or 100%).

In some embodiments, there is provided a method of prolonging progression-free survival of cancer in an individual, comprising administering to the individual an effective amount of activated T cells. In some embodiments, the method further comprises administering to the individual an effective amount of dendritic cells loaded with a plurality of tumor antigen peptides. In some embodiments, the method prolongs the time to disease progression by at least any of 1, 2, 3, 4, 5, 6, 7, 8, 9, 10, 11, or 12 weeks.

In some embodiments, there is provided a method of prolonging survival of an individual having cancer, comprising administering to the individual an effective amount of activated T cells. In some embodiments, the method further comprises administering to the individual an effective amount of dendritic cells loaded with a plurality of tumor antigen peptides. In some embodiments, the method prolongs the time to disease progression by at least about any one of 1, 2, 3, 4, 5, 6, 7, 8, 9, 10, 11, or 12 weeks. In some embodiments, the method prolongs the survival of the individual by at least about any one of 1, 2, 3, 4, 5, 6, 7, 8, 9, 10, 11, 12, 18, or 24 months.

In some embodiments, there is provided a method of reducing AEs and SAEs in an individual having cancer, comprising administering to the individual an effective amount of activated T cells. In some embodiments, the method further comprises administering to the individual an effective amount of dendritic cells loaded with a plurality of tumor antigen peptides.

In some embodiments, the method is predictive of and/or results in an objective response (such as a partial response or complete response). In some embodiments, the method is predictive of and/or results in improved quality of life.

Some cancer immunotherapies are associated with immune-related adverse events (irAEs) in additional to common adverse events generally associated with other cancer therapies. IrAEs are usually mechanistically related to either on-target T-cell toxicity against target antigens that are expressed in normal, non-tumor tissue, so called on-target off-tumor effect, or off-target effects such as breaking of self-tolerance or epitope cross-reaction. IrAEs can lead to severe symptoms and conditions on the dermatologic, gastrointestinal, endocrine, hepatic, ocular, neurologic, and other tissues or organs. Typical irAEs reported for cancer immunotherapy methods known in the art include fatal immune-mediated dermatitis, pneumonia, colitis, lymphocytic hypophysitis, pancreatitis, lymphadenopathy, endocrine disorders, CNS toxicity, and the like. In some embodiments, the improved MASCT method is associated with low incidence of adverse events, such as irAEs. In some embodiments, less than about any one of 50%, 40%, 30%, 20%, 10%, 5%, 4%, 3%, 2%, or 1% of individuals experience irAEs, such as irAEs of Grade 2-5.

Generally, dosages, schedules, and routes of administration of the activated T cells and the population of dendritic cells loaded with the plurality of tumor antigen peptides may be determined according to the size and condition of the individual, and according to standard pharmaceutical practice. Exemplary routes of administration include intravenous, intra-arterial, intraperitoneal, intrapulmonary, intravesicular, intramuscular, intra-tracheal, subcutaneous, intraocular, intrathecal, or transdermal. In some embodiments, the dendritic cells loaded with the plurality of tumor antigen peptides are administered subcutaneously. In some embodiments, the activated T cells are administered intravenously.

The dose of the cells administered to an individual may vary according to, for example, the particular type of cells being administered, the route of administration, and the particular type and stage of cancer being treated. The amount should be sufficient to produce a desirable response, such as a therapeutic response against cancer, but without severe toxicity or adverse events. In some embodiments, the amount of the activated T cells or the dendritic cells to be administered is a therapeutically effective amount. In some embodiments, the amount of the cells (such as multiple-antigen loaded dendritic cells, or the activated T cells) is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same individual prior to treatment or compared to the corresponding activity in other individuals not receiving the treatment. Standard methods can be used to measure the magnitude of this effect, such as in vitro assays with purified enzyme, cell-based assays, animal models, or human testing.

In some embodiments, the population of dendritic cells loaded with the plurality of tumor antigen peptides is administered at a dose at least about any one of $1\times10^5$, $5\times10^5$, $1\times10^6$, $1.5\times10^6$, $2\times10^6$, $3\times10^6$, $4\times10^6$, $5\times10^6$, $6\times10^6$, $7\times10^6$, $8\times10^6$, $9\times10^6$, $1\times10^7$ or $5\times10^7$ cells/individual. In some embodiments, the population of dendritic cells loaded with the plurality of tumor antigen peptides are administered at a dose about any one of $1\times10^5$-$5\times10^5$, $5\times10^5$-$1\times10^6$, $1\times10^6$-$2\times10^6$, $2\times10^6$-$3\times10^6$, $3\times10^6$-$4\times10^6$, $4\times10^6$-$5\times10^6$, $5\times10^6$-$6\times10^6$, $6\times10^6$-$7\times10^6$, $7\times10^6$-$8\times10^6$, $8\times10^6$-$1\times10^8$, $1\times10^6$-$3\times10^6$, $3\times10^6$-$5\times10^6$, $5\times10^6$-$7\times10^6$, $2\times10^6$-$2\times10^7$, $5\times10^6$-$2\times10^7$, or $1\times10^6$-$2\times10^7$ cells/individual. In some embodiments, the dendritic cells loaded with the plurality of tumor antigen peptides are administered at a dose of at least about $1\times10^6$ cells/individual. In some embodiments, the dendritic cells loaded with the plurality of tumor antigen peptides are administered at a dose of about $1.5\times10^6$ to about $1.5\times10^7$ cells/individual.

In some embodiments, the population of dendritic cells loaded with the plurality of tumor antigen peptides are administered at a dose at least about any one of $1\times10^4$, $2.5\times10^4$, $5\times10^4$, $1\times10^5$, $2\times10^5$, $2.5\times10^5$, $4\times10^5$, $6\times10^5$, $8\times10^5$, $1\times10^6$, $2\times10^6$ or $1\times10^7$ cells/kg. In some embodiments, the population of dendritic cells loaded with the plurality of tumor antigen peptides are administered at a dose about any one of $1\times10^4$-$5\times10^4$, $5\times10^4$-$1\times10^5$, $1\times10^5$-$2\times10^5$, $2\times10^5$-$4\times10^5$, $4\times10^5$-$6\times10^5$, $6\times10^5$-$8\times10^5$, $8\times10^5$-$1\times10^6$, $1\times10^6$-$2\times10^6$, $2\times10^6$-$1\times10^7$, $1\times10^4$-$1\times10^5$, $1\times10^5$-$1\times10^6$, $1\times10^6$-$1\times10^7$, $1\times10^4$-$1\times10^6$, or $1\times10^5$-$1\times10^7$ cells/kg. In some embodiments, the dendritic cells loaded with the plurality of tumor antigen peptides are administered at a dose of at least about $2\times10^5$ cells/kg. In some embodiments, the dendritic cells loaded with the plurality of tumor antigen peptides are administered at a dose of about $2.5\times10^4$ to about $2.5\times10^5$ cells/kg.

In some embodiments, the activated T cells are administered at a dose of at least about any one of $1\times10^8$, $5\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $1.5\times10^{10}$, $2\times10^{10}$, or $5\times10^{10}$ cells/individual. In some embodiments, the activated T cells are administered at a dose of about any one of $1\times10^8$-$5\times10^8$, $5\times10^8$-$1\times10^9$, $1\times10^9$-$5\times10^9$, $5\times10^9$-$1\times10^{10}$, $3\times10^9$-$7\times10^9$, $1\times10^{10}$-$2\times10^{10}$, or $1\times10^9$-$1\times10^{10}$ cells/individual. In some embodiments, the activated T cells are administered at a dose of at least about $3\times10^9$ cells/individual. In some embodiments, the activated T cells are administered at a dose of about $1\times10^9$ to about $1\times10^{10}$ cells/individual.

In some embodiments, the activated T cells are administered at a dose of at least about any one of $1\times10^7$, $2\times10^7$, $4\times10^7$, $6\times10^7$, $8\times10^7$, $1\times10^8$, $2\times10^8$, $4\times10^8$, $6\times10^8$, $8\times10^8$, $1\times10^9$ cells/kg. In some embodiments, the activated T cells are administered at a dose of about any one of $1\times10^7$-$1\times10^8$, $1\times10^7$-$5\times10^7$, $2\times10^7$-$4\times10^7$, $5\times10^7$-$1\times10^8$, $1\times10^8$-$2\times10^8$, $5\times10^7$-$1\times10^8$, $1\times10^8$-$2\times10^8$, $2\times10^8$-$5\times10^8$, $1\times10^8$-$1\times10^9$, or $1\times10^7$-$1\times10^9$ cells/kg. In some embodiments, the activated T cells are administered at a dose of at least about $6\times10^7$ cells/kg. In some embodiments, the activated T cells are administered at a dose of about $1.5\times10^7$ to about $2\times10^8$ cells/kg.

In some embodiments, a stabilizing agent or an excipient, such as human albumin, is used together with the activated T cells, and/or the dendritic cells loaded with the plurality of tumor antigen peptides.

The dosage and dosing schedule of the cells in the improved MASCT method may be adjusted over the course of the treatment, based on the judgment of the administering physician. In some embodiments, the activated T cells are administered at least about any one of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 28 days, after the dendritic cells loaded with the plurality of tumor antigen peptides are administered. In some embodiments, the activated T cells are administered concurrently with the dendritic cells. In some embodiments, the activated T cells are administered about 17-26 days after the dendritic cells are administered. In some embodiments, the activated T cells are administered about 17 days after the dendritic cells are administered.

The improved MASCT method may comprise a single treatment, or repeated treatments. In some embodiments, the activated T cells are administered for at least about any one of 1, 2, 3, 4, 5, 6, 7, 8, 9, 10, or more than 10 times. In some embodiments, the activated T cells are administered at least 3 times. In some embodiments, the dendritic cells are administered for at least about any one of 1, 2, 3, 4, 5, 6, 7, 8, 9, 10, or more than 10 times. In some embodiments, the dendritic cells are administered at least 3 times. In some embodiments, one or more cell (such as antigen-loaded dendritic cell or activated T cells) preparation steps are repeated prior to the repeated administration of the dendritic cells, the activated T cells, or both. In some embodiments, the improved MASCT method is repeated once per week, once 2 weeks, once 3 weeks, once 4 weeks, once per month, once per 2 months, once per 3 months, once per 4 months, once per 5 months, once per 6 months, once per 7 months, once per 8 months, once per 9 months, or once per year. In some embodiments, the interval between each administration of the dendritic cells, or the activated T cells is about any one of 1 week to 2 weeks, 2 weeks to 1 month, 2 weeks to 2 months, 1 month to 2 months, 1 month to 3 months, 3 months to 6 months, or 6 months to a year. In some embodiments, the interval between each administration of the dendritic cells or the activated T cells is about 1 day to about 5 months, such as about 2 weeks to about 2 months, or about 2 months to about 5 months. In some embodiments, all steps of the improved MASCT method are repeated once per month during the first 6 months of treatment, every two months for the second 6 months of treatment, and every half a year after first 12 months of treatment if the individual has stable disease. Any embodiment of the improved MASCT method described herein can be combined with any other embodiment of the improved MASCT method during the full course of a repeated treatment.

The improved MASCT method provided herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radio-frequency ablation or the like, in an adjuvant setting or a neoadjuvant setting. In some embodiments, the improved MASCT method is used as a first therapy. In some embodiments, there exists no other approved anti-cancer therapy for the individual. In some embodiments, the improved MASCT method is used as a second therapy, wherein the individual has previously received resection, radio-frequency ablation, chemotherapy, radiation therapy, or other types of cancer therapy. In some embodiments, the individual has progressed or has not been able to tolerate standard anti-cancer therapy. In some embodiments, the individual receives other types of cancer therapy prior to, concurrently with, or after the improved MASCT treatment(s). For example, the improved MASCT method may precede or follow the other cancer therapy (such as chemotherapy, radiation, surgery or combination thereof) by intervals ranging from minutes, days, weeks to months. In some embodiments, the interval between the first and the second therapy is such that the activated T cells of the improved MASCT method and the other cancer therapy (such as chemotherapy, radiation, surgery, or combination thereof) would be able to exert an advantageously combined effect on the individual. In some embodiments, the improved MASCT method is used in conjunction with other cancer therapy (such as chemotherapy, radiation, surgery, or combination thereof) treat cancer in an individual. The combination therapy methods described herein may be performed alone or in conjunction with another therapy, such as surgery, radiation, gene therapy, immunotherapy, bone marrow transplantation, stem cell transplantation, hormone therapy, targeted therapy, cryotherapy, ultrasound therapy, photodynamic therapy, chemotherapy or the like. Additionally, a person having a greater risk of developing a proliferative disease may receive treatments to inhibit and/or delay the development of the disease.

The methods described herein for treating cancer can be used in monotherapy as well as in combination therapy with another agent. For example, any of the treatment methods described herein may be combined with administration of one or more (such as any of 1, 2, 3, 4, or more) immune checkpoint inhibitors. In some embodiments, the immune checkpoint inhibitor is selected from the group consisting of inhibitors of PD-1, PD-L1, CTLA-4, IDO, TIM-3, BTLA, VISTA, and LAG-3.

In some embodiments, the immune checkpoint inhibitor is an inhibitor of PD-1. In some embodiments, the immune checkpoint inhibitor is an anti-PD-1 antibody. Exemplary anti-PD-1 antibodies include, but are not limited to, Nivolumab, pembrolizumab, pidilizumab, BMS-936559, and atezolizumab, Pembrolizumab, MK-3475, AMP-224, AMP-514, STI-A1110, and TSR-042. In some embodiments, the immune checkpoint inhibitor is nivolumab (for example, OPDIVO®). In some embodiments, the immune checkpoint inhibitor is Pembrolizumab (for example, KEYTRUDA®). In some embodiments, the immune checkpoint inhibitor is SHR-1210.

In some embodiments, the immune checkpoint inhibitor is an inhibitor of PD-L1. In some embodiments, the immune checkpoint inhibitor is an anti-PD-L1 antibody. Exemplary anti-PD-L1 antibodies include, but are not limited to, KY-1003, MCLA-145, RG7446, BMS935559, MPDL3280A, MEDI4736, Avelumab, or STI-A1010.

In some embodiments, the immune checkpoint inhibitor is an inhibitor of CTLA-4. In some embodiments, the immune checkpoint inhibitor is an anti-CTLA-4 antibody. Exemplary anti-CTLA-4 antibodies include, but are not limited to, Ipilimumab, Tremelimumab, and KAHR-102. In some embodiments, the immune checkpoint inhibitor is Ipilimumab (for example, YERVOY®).

In some embodiments, the activated T cells and the immune checkpoint inhibitor are administered simultaneously. In some embodiments, the activated T cells and the immune checkpoint inhibitor are administered in a single composition. In some embodiments, the immune checkpoint inhibitor is present in the co-culture. In some embodiments, the activated T cells and the immune checkpoint inhibitor are admixed prior to (such as immediately prior to) the administration. In some embodiments, the activated T cells and the immune checkpoint inhibitor are administered simultaneously via separate compositions.

In some embodiments, the activated T cells and the immune checkpoint inhibitor are administered sequentially. In some embodiments, the immune checkpoint inhibitor is administered prior to the administration of the activated T cells. In some embodiments, the immune checkpoint inhibitor is administered after the administration of the activated T cells.

Exemplary routes of administration of the immune checkpoint inhibitor include, but are not limited to, intratumoral, intravesical, intramuscular, intraperitoneal, intravenous, intra-arterial, intracranial, intrapleural, subcutaneous, and epidermal routes, or be delivered into lymph glands, body spaces, organs or tissues known to contain such live cancer cells. In some embodiments, the immune checkpoint inhibitor is administered intravenously. In some embodiments, the immune checkpoint inhibitor is administered by infusion. In some embodiments, the immune checkpoint inhibitor is infused over at least about any of 10 minutes, 30 minutes, 1 hour, 2 hours, 4 hours, 6 hours, or more. In some embodiments, the immune checkpoint inhibitor is administered via the same administration route as the activated T cells. In some embodiments, the immune checkpoint inhibitor is administered via a different administration route as the activated T cells.

Suitable dose of the immune checkpoint inhibitor include, but are not limited to, about any one of 1 mg/m$^2$, 5 mg/m$^2$, 10 mg/m$^2$, 20 mg/m$^2$, 50 mg/m$^2$, 100 mg/m$^2$, 200 mg/m$^2$, 300 mg/m$^2$, 400 mg/m$^2$, 500 mg/m$^2$, 750 mg/m$^2$, 1000 mg/m$^2$, or more. In some embodiments, the dose of immune checkpoint inhibitor is any one of about 1 to about 5 mg/m$^2$, about 5 to about 10 mg/m$^2$, about 10 to about 20 mg/m$^2$, about 20 to about 50 mg/m$^2$, about 50 to about 100 mg/m$^2$, about 100 mg/m$^2$ to about 200 mg/m$^2$, about 200 to about 300 mg/m$^2$, about 300 to about 400 mg/m$^2$, about 400 to about 500 mg/m$^2$, about 500 to about 750 mg/m$^2$, or about 750 to about 1000 mg/m$^2$. In some embodiments, the dose of immune checkpoint inhibitor is about any one of 1 µg/kg, 2 µg/kg, 5 µg/kg, 10 µg/kg, 20 µg/kg, 50 µg/kg, 0.1 mg/kg, 0.2 mg/kg, 0.3 mg/kg, 0.4 mg/kg, 0.5 mg/kg, 1 mg/kg, 2 mg/kg, 5 mg/kg, 10 mg/kg, 20 mg/kg, 50 mg/kg, 100 mg/kg, or more. In some embodiments, the dose of the immune checkpoint inhibitor is any one of about 1 µg/kg to about 5 µg/kg, about 5 µg/kg to about 10 µg/kg, about 10 µg/kg to about 50 µg/kg, about 50 µg/kg to about 0.1 mg/kg, about 0.1 mg/kg to about 0.2 mg/kg, about 0.2 mg/kg to about 0.3 mg/kg, about 0.3 mg/kg to about 0.4 mg/kg, about 0.4 mg/kg to about 0.5 mg/kg, about 0.5 mg/kg to about 1 mg/kg, about 1 mg/kg to about 5 mg/kg, about 5 mg/kg to about 10 mg/kg, about 10 mg/kg to about 20 mg/kg, about 20 mg/kg to about 50 mg/kg, about 50 mg/kg to about 100 mg/kg, or about 1 mg/kg to about 100 mg/kg.

In some embodiments, the immune checkpoint inhibitor is administered daily. In some embodiments, the immune checkpoint inhibitor is administered is administered at least about any one of 1×, 2×, 3×, 4×, 5×, 6×, or 7× (i.e., daily) a week. In some embodiments, the immune checkpoint inhibitor is administered weekly. In some embodiments, the immune checkpoint inhibitor is administered weekly without break; weekly, two out of three weeks; weekly three out of four weeks; once every two weeks; once every 3 weeks; once every 4 weeks; once every 6 weeks; once every 8 weeks, monthly, or every two to 12 months. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, the immune checkpoint inhibitor is administered once every 3 months. In some embodiments, there is no break in the dosing schedule. In some embodiments, the interval between each administration is no more than about a week. In some embodiments, the immune checkpoint inhibitor is administered with the same dosing schedule as the activated T cells. In some embodiments, the immune checkpoint inhibitor is administered with a different dosing schedule as the activated T cells.

In some embodiments, the immune checkpoint inhibitor is administered in every improved MASCT treatment cycle. For example, the immune checkpoint inhibitor may be administered about any of 1, 2, 3, 4, 5, 6, or more times every improved MASCT treatment cycle. In some embodiments, the immune checkpoint inhibitor is not administered in every improved MASCT treatment cycle. For example, the immune checkpoint inhibitor may be administered about once every 1, 2, 3, 4, 5, or more improved MASCT treatment cycles.

The administration of the immune checkpoint inhibitor can be over an extended period of time, such as from about a month up to about seven years. In some embodiments, the immune checkpoint inhibitor is administered over a period of at least about any one of 1, 2, 3, 4, 5, 6, 7, 8, 9, 10, 11, 12, 18, 24, 30, 36, 48, 60, 72, or 84 months. In some embodiments, the immune checkpoint inhibitor is administered for a single time. In some embodiments, the immune checkpoint inhibitor is administered repeatedly. In some embodiments, the immune checkpoint inhibitor is administered repeatedly until disease progression.

IV. Precision Improved MASCT Methods

Further provided herein are precision improved MASCT methods that are customized to the individual being treated based on the genetics and therapeutic response of the individual. Any of the methods of treatment described above in Section III may be customized to provide a precision improved MASCT method.

The improved MASCT methods described herein in some embodiments are particularly suitable for a certain population of individuals, such as individuals with a low mutation load (such as in the MHC genes) in the cancer (such as all or a subset of cancer cells), and/or individuals with one or more neoantigens.

Mutation Load

In some embodiments, the improved MASCT method is particularly suitable for an individual with a low total mutation load in the cancer of the individual. In some embodiments, the improved MASCT method is particularly suitable for an individual with a low mutation load in the cancer-associated genes in the cancer of the individual. In some embodiments, the improved MASCT method is particularly suitable for an individual with a low mutation load in immune genes related to T cell response in the cancer of the individual. In some embodiments, the improved MASCT method is particularly suitable for an individual with a low mutation load in the MHC genes in the cancer of the individual. The mutation load may be mutation load in all cancer cells, or a subset of cancer cells, such as a primary or metastatic tumor site, for example, cells in a tumor biopsy sample.

Thus, in some embodiments, there is provided a method of treating a cancer in an individual, comprising: (a) optionally administering an effective amount of dendritic cells loaded with a plurality of tumor antigen peptides; and (b) administering to the individual an effective amount of activated T cells, wherein the activated T cells are prepared by any one of the methods of preparing activated T cells described above in Section II, and wherein the individual has a low mutation load in the cancer.

In some embodiments, there is provided a method of treating a cancer in an individual, comprising: (a) selecting the individual for the method based on the mutation load in the cancer; (b) optionally administering an effective amount of dendritic cells loaded with a plurality of tumor antigen peptides; and (c) administering to the individual an effective amount of activated T cells, wherein the activated T cells are prepared by any one of the methods of preparing activated T cells described above in Section II.

In some embodiments, there is provided a method of treating a cancer in an individual, comprising: (a) optionally administering an effective amount of dendritic cells loaded with a plurality of tumor antigen peptides; and (b) administering to the individual an effective amount of activated T cells, wherein the activated T cells are prepared by any one of the methods of preparing activated T cells described above in Section II, and wherein the individual is selected for treatment based on having a low mutation load in the cancer.

In some embodiments, a low mutation load of one or more genes is a low number of mutations accumulated on the one or more genes. In some embodiments, a total number of no more than about any of 500, 400, 300, 200, 100, 50, 40, 30, 20, 10, 5 or fewer mutations indicate a low mutation load. In some embodiments, no more than about any of 50, 40, 30, 25, 20, 15, 14, 13, 12, 11, 10, 9, 8, 7, 6, 5, 4, 3, 2 or 1 mutations in the one or more MEC genes indicate a low mutation load of the one or more MHC genes. In some embodiments, a low mutation load of one or more genes is a low ratio between the number of mutations accumulated on the one or more genes (such as MHC genes) and the total number of mutations in a selected set of genes (such as cancer-associated genes) or the full genome.

In some embodiments, the one or more MHC genes comprise MHC class I genes (or loci). In some embodiments, the one or more MHC genes comprise MEC class II genes (or loci). In some embodiments, wherein the individual is a human individual, the one or more MHC genes are selected from the group consisting of HLA-A, HLA-B, HLA-C and B2M.

Exemplary mutations include, but are not limited to, deletion, frameshift, insertion, indel, missense mutation, nonsense mutation, point mutation, copy number variation, single nucleotide variation (SNV), silent mutation, splice site mutation, splice variant, gene fusion, and translocation. In some embodiments, the copy number variation of the MEC gene is caused by structural rearrangement of the genome, including deletions, duplications, inversion, and translocation of a chromosome or a fragment thereof. In some embodiments, the mutations in the one or more MHC genes are selected from point mutations, frameshift mutations, gene fusions, and copy number variations. In some embodiments, the mutations are in the protein-coding region of the MHC genes. In some embodiments, the mutation is a nonsynonymous mutation. In some embodiments, the mutation is not a polymorphism. In some embodiments, the mutation is present in normal cells of the individual. In some embodiments, the mutation is not present in normal cells of the individual. In some embodiments, the mutation affects the physiochemical or functional properties, such as stability or binding affinity, of the MEC molecule encoded by the affected gene. In some embodiments, the mutation results in an irreversible deficiency in the MHC molecule. In some embodiments, the mutation reduces the binding affinity of the MHC molecule to T cell epitopes and/or T cell receptors. In some embodiments, the mutation is a loss-of-function mutation. In some embodiments, the mutation results in reversible deficiency in the MHC molecule. In some embodiments, the mutation does not affect the binding affinity of the MHC molecule to T cell epitopes and/or T cell receptors. In some embodiments, the mutation is a somatic mutation. In some embodiments, the mutation is a germline mutation.

The mutations counted towards the mutation load may be present in all cancer cells or in a subset of cancer cells. In some embodiments, the mutations are present in all cancer cells in the individual. In some embodiments, the mutations are present in all cancer cells of a tumor site. In some embodiments, the mutations are clonal. In some embodiments, the mutations are subclonal. In some embodiments, the mutations are present in at least about any of 10%, 20%, 30%, 40%, 50%, 60%, 70%, 80%, 90%, 95%, or more cancer cells of the individual.

The mutations in certain MHC genes and/or in certain domains or positions of the one or more MEC genes may have more profound influence on the clinical response of the individual to the improved MASCT methods described herein. For example, loss-of-function mutations may occur in the leader peptide sequence, a3 domain (which binds the CD8 co-receptor of T cells), al peptide binding domain, or a2 peptide binding domain of the HLA molecule; see, for example, Shukla S. et al. *Nature Biotechnology* 33, 1152-1158 (2015), incorporated herein by reference. Mutations in B2M (β2-macroglobulin) gene may also promote tumor escape phenotypes. See, for example, Monica B et al. *Cancer Immunol. Immu.,* (2012) 61: 1359-1371. In some embodiments, presence of any number (such as 1, 2, 3, 4, 5, or more) of mutations in the functional regions of the one or more MEC genes, such as the leader peptide sequence, a1 domain, a2 domain, or a3 domain, indicates a high mutation load. In some embodiments, presence of any number (such as 1, 2, 3, 4, 5, or more) loss-of-function mutations in the one or more MHC genes (such as HLA-A, HLA-B or FILA-C genes in human individuals) indicates a high mutation load. In some embodiments, a low mutation load in the one or more MHC genes comprises no mutation in the functional regions, including leader peptide sequence, a1 domain (for example, residues in direct contact with the CD8 co-receptor), a2 domain, and a3 domain (for example, residues in direct contact with the epitope), of the one or more MHC genes (such as HLA-A, HLA-B or HLA-C genes). In some embodiments, presence of any number of mutations (such as loss-of-function mutations) in the B2M gene indicates a high mutation load. In some embodiments, a low mutation load in the one or more MHC genes comprises no mutation in the B2M gene.

The mutation load of one or more genes (such as MHC genes) may be determined by any known methods in the art, including, but not limited to, genomic DNA sequencing, exome sequencing, or other DNA sequencing-based methods using Sanger sequencing or next generation sequencing platforms; polymerase chain reaction assays; in situ hybridization assays; and DNA microarrays.

In some embodiments, the mutation load of the one or more MHC genes is determined by sequencing a tumor sample from the individual. In some embodiments, the sequencing is next generation sequencing. In some embodiments, the sequencing is full genome sequencing. In some embodiments, the sequencing is exome sequencing. In some embodiments, the sequencing is targeted sequencing of candidate genes, such as cancer-associated genes plus HLA genes. For example, ONCOGXONE™ Plus (Admera Health), are available to sequence cancer-associated genes and HLA loci with high sequencing depth. In some embodiments, the same sequencing data can be used to determine the mutation load of the one or more MHC genes and to identify neoantigens in the individual.

In some embodiments, the tumor sample is a tissue sample. In some embodiments, the tumor sample is a tumor biopsy sample, such as fine needle aspiration of tumor cells or laparoscopy obtained tumor cells (such as including tumor stroma). In some embodiments, the tumor sample is freshly obtained. In some embodiments, the tumor sample is frozen. In some embodiments, the tumor sample is a Formaldehyde Fixed-Paraffin Embedded (FFPE) sample. In some embodiments, the tumor sample is a cell sample. In some embodiments, the tumor sample comprises a circulating metastatic cancer cell. In some embodiments, the tumor sample is obtained by sorting circulating tumor cells (CTCs) from blood. In some embodiments, nucleic acids (such as DNA and/or RNA) are extracted from the tumor sample for the sequencing analysis. In some embodiments, the sequencing data of the tumor sample is compared to the sequencing data of a reference sample, such as a sample of a healthy tissue from the same individual, or a sample of a healthy individual, to identify mutations and determine mutation load in the tumor cells. In some embodiments, the sequencing data of the tumor sample is compared to the reference sequences from a genome database to identify mutations and determine mutation load in the tumor cells.

Neoantigen Peptides

In some embodiments, the improved MASCT method is particularly suitable for treating an individual with one or more neoantigens. Any of the improved MASCT methods described herein using one or more neoantigen peptides in the plurality of tumor antigen peptides may further comprise the steps of selecting the individual for the method of treating based on having one or more (such as at least 5) neoantigens in the individual, and/or the steps of: (i) identifying a neoantigen of the individual; and (ii) incorporating a neoantigen peptide derived from the neoantigen in the plurality of tumor antigen peptides for use in the improved MASCT method.

Thus, in some embodiments, there is provided a method of treating a cancer in an individual, comprising: (a) identifying a neoantigen of the individual; (b) incorporating a neoantigen peptide in a plurality of tumor antigen peptides, wherein the neoantigen peptide comprises a neoepitope in the neoantigen; (c) optionally administering an effective amount of dendritic cells loaded with the plurality of tumor antigen peptides; (d) preparing a population of activated T cells using any one of the methods of preparing activated T cells described above in Section II; and (e) administering to the individual an effective amount of activated T cells, wherein the individual has one or more neoantigens.

The individual may have any number (such as at least about any one of 1, 2, 4, 5, 6, 7, 8, 9, 10, 11, 12, 13, 14, 15, 20, 50, 100 or more) of neoantigens in order to benefit from the improved MASCT method using a plurality of tumor antigen peptides comprising a neoantigen peptide. In some embodiments, the improved MASCT method is particularly suitable for an individual having at least about any one of 4, 5, 6, 7, 8, 10, 15, 20, 50, 100 or more neoantigens. In some embodiments, the neoantigen comprises one or more neoepitopes. In some embodiments, the improved MASCT method is particularly suitable for an individual having at least about any one of 4, 5, 6, 7, 8, 10, 15, 20, 50, 100 or more neoepitopes. In some embodiments, the T cell epitopes are MHC-I restricted epitopes. In some embodiments, the neoepitope has a higher affinity to the MHC molecules of the individual than the corresponding wildtype T cell epitope. In some embodiments, the neoepitope has higher affinity to a model T cell receptor than the corresponding wildtype T cell epitope. In some embodiments, the neoantigen (or neoepitope) is a clonal neoantigen. In some embodiments, the neoantigen (or neoepitope) is a subclonal neoantigen. In some embodiments, the neoantigen (or neoepitope) is present in at least about any one of 10%, 20%, 30%, 40%, 50%, 60%, 70%, 80%, 90%, 95% or more tumor cells in the individual.

The number of neoantigens may be combined with other biomarkers or selection criteria to select an individual for any one of the improved MASCT methods described herein. In some embodiments, the improved MASCT method is particularly suitable for an individual having a low mutation load (such as in one or more MHC genes) in the cancer cells, and at least about any of 4, 5, 6, 7, 8, 10 or more neoantigens (such as neoantigens with high affinity MHC-I restricted neoepitopes).

Any number (such as any of 1, 2, 3, 4, 5, 6, 7, 8, 9, 10, or more) of neoantigen peptides may be designed based on the neoantigens of the individual and to be incorporated in the plurality of tumor antigen peptides for use in any of the improved MASCT methods described herein. In some embodiments, the plurality of tumor antigen peptides comprises a single neoantigen peptide. In some embodiments, the plurality of tumor antigen peptides comprises a plurality of neoantigen peptides. Each neoantigen peptide may comprise one or more neoepitopes from a neoantigen of the individual. In some embodiments, the neoepitope is a T cell epitope. Methods of designing a neoantigen peptide based on a neoantigen are described in the section "Plurality of tumor antigen peptides."

The neoantigens in the individual may be identified using any known methods in the art. In some embodiments, the neoantigen is identified based on the genetic profile of a tumor sample from the individual. Each neoantigen comprises one or more neoepitopes. In some embodiments, the one or more neoepitopes in the neoantigen are identified based on the genetic profile of the tumor sample. Any known genetic profiling methods, such as next generation sequencing (NGS) methods, microarrays, or proteomic methods may be used to provide the genetic profile of the tumor sample.

In some embodiments, the neoantigen is identified by sequencing a tumor sample from the individual. In some embodiments, the sequencing is next generation sequencing. In some embodiments, the sequencing is full-genome sequencing. In some embodiments, the sequencing is exome sequencing, such as whole exome sequencing ("WES"). In some embodiments, the sequencing is RNA sequencing. In some embodiments, the sequencing is targeted sequencing of candidate genes, such as cancer-associated genes. Many commercial NGS cancer panels, for example, ONCOGXONE™ Plus (Admera Health), are available to sequence cancer-associated genes with high sequencing depth.

In some embodiments, the tumor sample is a tissue sample. In some embodiments, the tumor sample is a tumor biopsy sample, such as fine needle aspiration of tumor cells or laparoscopy obtained tumor cells (such as including tumor stroma). In some embodiments, the tumor sample is freshly obtained. In some embodiments, the tumor sample is frozen. In some embodiments, the tumor sample is a Formaldehyde Fixed-Paraffin Embedded (FFPE) sample. In some embodiments, the tumor sample is a cell sample. In some embodiments, the tumor sample comprises a circulating metastatic cancer cell. In some embodiments, the tumor sample is obtained by sorting circulating tumor cells (CTCs) from blood. In some embodiments, nucleic acids (such as DNA and/or RNA) are extracted from the tumor sample for the sequencing analysis. In some embodiments, proteins are extracted from the tumor sample for the sequencing analysis.

In some embodiments, the genetic profile of the tumor sample is compared to the genetic profile of a reference sample, such as a sample of a healthy tissue from the same individual, or a sample of a healthy individual, to identify candidate mutant genes in the tumor cells. In some embodiments, the genetic profile of the tumor sample is compared to the reference sequences from a genome database to identify candidate mutant genes in the tumor cells. In some embodiments, the candidate mutant genes are cancer-associated genes. In some embodiments, each candidate mutant gene comprises one or more mutations, such as non-synonymous substitutions, single nucleotide variation (SNV), indel (insertion or deletion, e.g., non-frame shift indel), new open reading frame (ORF), or gene fusion, which may give rise to a neoantigen. Common Single Nucleotide Polymorphisms (SNPs) are excluded from the candidate mutations.

In some embodiments, neoepitopes in neoantigens are identified from the candidate mutant proteins. In some embodiments, the neoepitopes are predicted in silico. Exemplary bioinformatics tools for T cell epitope prediction are known in the art, for example, see Yang X. and Yu X. (2009) "An introduction to epitope prediction methods and software" *Rev. Med. Virol.* 19(2): 77-96. Factors considered in the T cell epitope prediction algorithms include, but are not limited to, MEC subtype of the individual, sequence-derived physiochemical properties of the T cell epitope, MEC binding motifs, proteasomal cleavage pattern, transporter associated with antigen processing (TAP) transport efficiency, MEC binding affinity, peptide-MHC stability, and T-cell receptor binding affinity. In some embodiments, the neoepitope is an MHC-I restricted epitope. In some embodiments, the neoepitope is an MHC-II restricted epitope.

In some embodiments, the neoepitope has high affinity to the MHC molecules of the individual. In some embodiments, the method further comprises determining the MHC subtype of the individual, for example, from the sequencing data, to identify one or more MHC molecules of the individual. In some embodiments, the method further comprises determining the affinity of the neoepitope to an MHC molecule, such as an MEC class I molecule. In some embodiments, the method comprises determining the affinity of the neoepitope to one or more MHC (such as MHC class I) molecules of the individual. In some embodiments, the affinity of the neoepitope to one or more MHC molecules of the individual is compared to the affinity of the corresponding wildtype epitope to the one or more MHC molecules of the individual. In some embodiments, the neoepitope is selected for having a higher (such as at least about any of 1.5, 2, 5, 10, 15, 20, 25, 50, 100, or more times) affinity to the one or more MHC molecules (such as MHC-I molecules) of the individual than the corresponding wildtype epitope. In some embodiments, the MHC binding affinity is predicted in silico using any known tools or methods in the art. In some embodiments, the MEC binding affinity is determined experimentally, such as using an in vitro binding assay.

In some embodiments, the method further comprises determining the affinity of the complex comprising the neoepitope and an MEC molecule (such as an MHC class I molecule of the individual) to a T cell receptor. In some embodiments, the affinity of the complex comprising the neoepitope and the MHC molecule to the T cell receptor is compared to that of the complex comprising the corresponding wildtype epitope and the MHC molecule. In some embodiments, the MHC molecule is from the individual. In some embodiments, the T cell receptor is on the surface of one or more T cells of the individual. In some embodiments, the neoepitope is selected for having a higher (such as at least about any one of 1.5, 2, 5, 10, 15, 20, 25, 50, 100, or more times) affinity in a complex comprising the neoepitope and an MEC molecule to a T cell receptor model than the corresponding wildtype epitope. In some embodiments, the TCR binding affinity is predicted in silico using any known tools or methods in the art. In some embodiments, the TCR binding affinity is determined experimentally, for example, by determining the T cell response against the neoepitope.

In some embodiments, the neoantigen (or the neoepitope) is identified further based on the expression level of the neoantigen (or the neoepitope) in the tumor sample. Expression level of the neoantigen (or the neoepitope) may be determined using any methods for quantification of mRNA or protein levels known in the art, such as RT-PCR, antibody-based assays, mass spectrometry. In some embodiments, the expression level of the neoantigen (or the neoepitope) is determined from the sequencing data of the tumor sample. In some embodiments, the neoantigen (or the neoepitope) is expressed in the tumor cells at a level of at least about any one of 10, 20, 50, 100, 200, 500, 1000, 2000, 5000, $10^4$, or more copies per cell. In some embodiments, the neoantigen (or the neoepitope) is expressed at a level of more than about any one of 1.5, 2, 5, 10, 20, 50, 100, or more times than the corresponding wildtype protein (or the corresponding wildtype epitope) in the tumor cells.

In some embodiments, the neoantigen peptide is selected or identified by the steps comprising: (a) sequencing a tumor sample from the individual to identify a neoantigen; (b) identifying a neoepitope in the neoantigen; optionally (c) determining the MHC subtype of the individual (e.g., using the sequencing data) to identify an MHC molecule of the individual; optionally (d) determining the affinity of the neoepitope to the MHC molecule of the individual; optionally (e) determining the affinity of the complex comprising the neoepitope and the MHC molecule to a T cell receptor; and (f) obtaining a peptide comprising the neoepitope to provide the neoantigen peptide. In some embodiments, the neoepitope has higher affinity to the MHC molecule (such as MHC-I molecule) of the individual and/or higher affinity in the complex comprising the neoepitope and the MHC molecule to the TCR as compared to the complex comprising the corresponding wildtype T cell epitope and the MHC molecule. In some embodiments, the neoepitope is extended at the N terminus or the C terminus or both termini according to the natural sequence of the neoantigen harboring the epitope to obtain an extended sequence, wherein the extended sequence is amenable for presentation by both class I and class II MHC molecules. Any of the improved MASCT methods described herein using one or more neoantigen peptides may further comprise any one or more of the neoantigen selection/identification steps.

Monitoring After Improved MASCT

Any of the improved MASCT methods described herein may further comprise a monitoring step after the individual receives the improved MASCT treatment. Post-treatment monitoring may be beneficial for adjusting the treatment regimen of the individual to optimize treatment outcome.

For example, the plurality of tumor antigen peptides described herein may be adjusted or customized based on the specific immune response of the individual against each of the plurality of tumor antigen peptides and/or the clinical response of the individual to the activated T cells in order to provide a plurality of customized tumor antigen peptides, which may be used for repeated improved MASCT treatment(s). In some embodiments, tumor antigen peptides that do not elicit a strong specific immune response can be removed from the antigen peptide pool for future preparations of the pulsed DCs or activated T cells. In some embodiments, if the individual does not respond (such as having signs of disease progression, metastasis, etc.) to the improved MASCT treatment using one antigen peptide pool, the antigen peptide pool may be adjusted, or neoantigens may be incorporated in the antigen peptide pool for use in a second cycle of the improved MASCT treatment.

Specific immune response against one or more tumor antigen peptides may be determined using any known methods in the art, for example, by measuring levels of cytotoxic factor (such as perforin or granzyme B), or cytokine release (such as IFNγ or TNFα) from T cells (or PBMCs) after stimulation by the individual tumor antigen peptide. An antibody-based assay, such as ELISPOT, may be used to quantify the cytotoxic factor, or cytokine (such as IFNγ) levels. In some embodiments, the cytokine (such as IFNγ) release level from T cells (or PBMCs) in response to a tumor antigen peptide is normalized to a reference, such as a baseline cytokine release level, or a nonspecific cytokine release level of from T cells (or PBMCs) in response to an irrelevant peptide, to provide a cytokine (such as IFNγ) fold change value. In some embodiments, a cytokine (such as IFNγ) fold change value of more than about any one of 1.2, 1.5, 2, 2.5, 3, 4, 5, 6, 8, 10, or more in an ELISPOT assay indicate strong specific immune response against the tumor antigen peptide. In some embodiments, a tumor antigen peptide with a cytokine (such as IFNγ) fold change value of less than about any one of 10, 8, 6, 5, 4, 3, 2.5, 2, 1.5, 1.2 or less in an ELISPOT assay is removed from the plurality of tumor antigen peptides to provide a plurality of customized tumor antigen peptides for future improved MASCT treatments.

Clinical response of the individual to the improved MASCT methods may be assessed by known methods in the art by a physician, such as by imaging methods, blood tests, biomarker assessment, and biopsy. In some embodiments, the clinical response is monitored by determining the number of circulating tumor cells (CTC) in the individual before and after receiving the improved MASCT treatment. In some embodiments, the CTCs have detached from a primary tumor and circulate in a bodily fluid. In some embodiments, the CTCs have detached from a primary tumor and circulate in the bloodstream. In some embodiments, the CTCs are an indication of metastasis. CTC numbers can be determined by a variety of methods known in the art, including, but not limited to, CellSearch method, Epic Science method, isoflux, and maintrac. In some embodiments, the number of single CTCs, including specific subtypes of CTCs, in a blood sample of the individual is determined. In some embodiments, a number of more than about any of 10, 20, 50, 100, 150, 200, 300 or more of single CTCs per mL of the blood sample in the individual after receiving the improved MASCT treatment indicates an increased risk of metastasis, and/or poor clinical response to the improved MASCT treatment. In some embodiments, an increased number (such as at least about any one of 1.5, 2, 3, 4, 5, 10, or more fold increase) of single CTCs of the individual after receiving the improved MASCT treatment compared to before receiving the improved MASCT treatment indicates poor clinical response to the improved MASCT treatment. In some embodiments, the number of CTC clusters in a blood sample of the individual is determined. In some embodiments, detection of at least about any of 1, 5, 10, 50, 100, or more CTC clusters in a blood sample of the individual after receiving the improved MASCT treatment indicates an increased risk of metastasis, and/or poor clinical response to the improved MASCT treatment. In some embodiments, an increased number (such as at least about any one of 1.5, 2, 3, 4, 5, 10, or more fold increase) of CTC clusters of the individual after receiving the improved MASCT treatment compared to before receiving the improved MASCT treatment indicates poor clinical response to the improved MASCT treatment.

V. Compositions, Kits and Articles of Manufacture

The present application further provides kits, compositions (such as pharmaceutical compositions), and articles of manufacture for use in any embodiment of the improved MASCT methods (including the precision improved MASCT methods) or the cell (such as antigen-loaded DCs or activated T cells) preparation methods described herein.

In some embodiments, there is provided a kit useful for cancer immunotherapy, comprising at least 10 tumor antigen peptides. A person skilled in the art may use any combinations of tumor antigen peptides from the first core group and optionally any combinations of cancer-type specific antigen peptides from the second group, and/or neoantigen peptides to load a population of dendritic cells, which can further be used to prepare activated T cells useful for treating cancer in an individual.

The kit may contain additional components, such as containers, reagents, culturing media, cytokines, immune checkpoint inhibitors, TLR agonists, buffers, antibodies, and the like to facilitate execution of any embodiment of the treatment methods or cell preparation methods described herein. For example, in some embodiments, the kit further comprises a peripheral blood collection and storage apparatus, which can be used to collect an individual's peripheral blood. In some embodiments, the kit further comprises containers and reagents for density gradient centrifugation of peripheral blood, which can be used to isolate PBMCs from a sample of human peripheral blood. In some embodiments, the kit further comprises culturing media, cytokines, or buffers for obtaining dendritic cells from peripheral blood. In some embodiments, the kit further comprises culturing media, TLR agonists (e.g., MPLA), IFNγ, PGE2, reagents and buffers for loading the plurality of tumor antigen peptides into dendritic cells. In some embodiments, the kit further comprises cytokines (e.g., IL-2, IL-7, IL-15 and IL-21), immune checkpoint inhibitors (e.g., anti-PD1 antibody), anti-CD3 antibody, buffers, or culturing media for co-culturing T cells obtained from the peripheral blood with the dendritic cells loaded with the plurality of tumor antigen peptides. In some embodiments, the kit further comprises reagents for determining the mutation load (such as in one or more MHC genes) in cancer cells. In some embodiments, the kit further comprises an immune checkpoint inhibitor for combination therapy with the improved MASCT. In some embodiments, the kit further comprises reagents for identifying a neoantigen (such as by sequencing) in a tumor sample. In some embodiments, the kit further comprises an ELISPOT assay for assessing specific immune response against the plurality of tumor antigen peptides.

The kits of the present application are in suitable packaging. Suitable packaging include, but is not limited to, vials, bottles, jars, flexible packaging (e.g., Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions may also comprise instructions relating to the use of the tumor antigen peptides (and optionally additional components described above). In some embodiments, the kit further comprises an instructional manual, such as a manual describing a protocol of an embodiment of the improved MASCT methods (including the precision improved MASCT methods), or an embodiment of the cell preparation methods as described herein. The instructions may also include information on dosage, dosing schedule, and routes of administration of the dendritic cells and/or the activated T cells prepared using the kit for the intended treatment. In some embodiments, the kit further comprises instructions for selecting an individual for the improved MASCT method. In some embodiments, the kit further comprises instructions for determining the mutation load of cancer cells, and/or determining the number of neoantigens in an individual. In some embodiments, the kit further comprises instructions for administering an immune checkpoint inhibitor in combination with the improved MASCT, including, for example, information on dosage, dosing schedule, and route of administration of the immune checkpoint inhibitor. In some embodiments, the kit further comprises instructions for identifying a neoantigen (such as by sequencing) in a tumor sample. In some embodiments, the kit further comprises instructions for monitoring an individual after receiving the improved MASCT treatment.

The containers may be unit doses, bulk packages (e.g., multi-dose packages) or sub-unit doses. For example, kits may be provided that contain sufficient tumor antigen peptides as disclosed herein to prepare sufficient activated T cells and/or antigen-loaded dendritic cells (such as dendritic cells) to provide effective treatment of an individual for an extended period, such as any of 3 weeks, 6 weeks, 9 weeks, 3 months, 4 months, 5 months, 6 months, 8 months, 9 months, 1 year or more.

Kits may also include multiple unit doses of tumor antigen peptides and instructions for use and packaged in quantities sufficient for storage and use in pharmacies, for example, hospital pharmacies and compounding pharmacies.

Further provided are kits, compositions (such as pharmaceutical compositions), and articles of manufacture of any one of the isolated population of cells (such as dendritic cells, or activated T cells) described herein.

The isolated population of cells described herein may be used in pharmaceutical compositions or formulations, by combining the isolated population of cells described with a pharmaceutically acceptable carrier, excipients, stabilizing agents and/or other agents, which are known in the art, for use in the methods of treatment, methods of administration, and dosage regimens described herein. In some embodiments, human albumin is used as a pharmaceutically acceptable carrier.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. The final form may be sterile and may also be able to pass readily through an injection device such as a hollow needle. The proper viscosity may be achieved and maintained by the proper choice of solvents or excipients.

The pharmaceutical compositions described herein may include other agents, excipients, or stabilizers to improve properties of the composition. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. In some embodiments, the pharmaceutical composition is formulated to have a pH in the range of about 4.5 to about 9.0, including for example pH ranges of about any one of 5.0 to about 8.0, about 6.5 to about 7.5, or about 6.5 to about 7.0. In some embodiments, the pharmaceutical composition can also be made to be isotonic with blood by the addition of a suitable tonicity modifier, such as glycerol.

In some embodiments, the isolated cell compositions (such as pharmaceutical compositions) is suitable for administration to a human. In some embodiments, the compositions (such as pharmaceutical compositions) is suitable for administration to a human by parenteral administration. Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as ampules and vials, and can be stored in a condition requiring only the addition of the sterile liquid excipient methods of treatment, methods of administration, and dosage regimens described herein (i.e., water) for injection, immediately prior to use. In some embodiments, the compositions (such as pharmaceutical compositions) is contained in a single-use vial, such as a single-use sealed vial. In some embodiments, each single-use vial contains about $10^9$ activated T cells. In some embodiments, each single-use vial contains enough activated T cells to be expanded to about $10^9$ activated T cells. In some embodiments, the composition (such as pharmaceutical composition) is contained in a multi-use vial. In some embodiments, the composition (such as pharmaceutical composition) is contained in bulk in a container.

Also provided are unit dosage forms comprising the isolated cell compositions (such as pharmaceutical compositions) and formulations described herein. These unit dosage forms can be stored in a suitable packaging in single or multiple unit dosages and may also be further sterilized and sealed. In some embodiments, the composition (such as pharmaceutical composition) also includes one or more other compounds (or pharmaceutically acceptable salts thereof) that are useful for treating cancer.

The present application further provides kits comprising any of the isolated population of cells, compositions (such as pharmaceutical compositions), formulations, unit dosages, and articles of manufacture described herein for use in the methods of treatment, methods of administration, and dosage regimens described herein. Kits described herein include one or more containers comprising the activated T cells.

VI. Exemplary Embodiments

Among the embodiments provided herein are:

1. A method of preparing a population of activated T cells, the method comprising:
   a) contacting a population of dendritic cells with a plurality of tumor antigen peptides to obtain a population of dendritic cells loaded with the plurality of tumor antigen peptides;
   b) co-culturing the population of dendritic cells loaded with the plurality of tumor antigen peptides and a population of T cells in an initial co-culture medium comprising a plurality of cytokines and an immune checkpoint inhibitor to provide a co-culture; and
   c) adding an anti-CD3 antibody to the co-culture at about 3 to 7 days after the co-culturing starts, thereby obtaining the population of activated T cells.

2. The method of embodiment 1, wherein step a) further comprises culturing the population of dendritic cells loaded with the plurality of tumor antigen peptides in a DC maturation medium comprising a toll-like receptor (TLR) agonist.

3. The method of embodiment 2, wherein the TLR agonist is selected from the group consisting of MPLA, Poly I:C, resquimod, gardiquimod, and CL075.

4. A method of preparing a population of activated T cells, the method comprising:
   a) contacting a population of dendritic cells with a plurality of tumor antigen peptides to obtain a population of dendritic cells loaded with the plurality of tumor antigen peptides;
   b) culturing the population of dendritic cells loaded with the plurality of tumor antigen peptides in a DC maturation medium comprising MPLA; and
   c) co-culturing the population of dendritic cells loaded with the plurality of tumor antigen peptides and a population of T cells, thereby obtaining the population of activated T cells.

5. The method of embodiment 3 or 4, wherein the DC maturation medium comprises INFγ and MPLA.

6. The method of embodiment 5, wherein the DC maturation medium further comprises PGE2.

7. The method of embodiment 5 or 6, wherein the INFγ is present in the DC maturation medium at a concentration of at least about 100 IU/mL.

8. The method of any one of embodiments 3-7, wherein the MPLA is present in the DC maturation medium at a concentration of at least about 0.5 μg/mL.

9. The method of any one of embodiments 6-8, wherein the PGE2 is present in the DC maturation medium at a concentration of at least about 0.1 μg/mL.

10. The method of any one of embodiments 4-9, wherein step c) comprises: co-culturing the population of dendritic cells loaded with the plurality of tumor antigen peptides and a population of T cells in an initial co-culture medium comprising a plurality of cytokines and an immune checkpoint inhibitor to provide a co-culture; and adding an anti-CD3 antibody to the co-culture, thereby obtaining the population of activated T cells.

11. The method of any one of embodiments 1-3 and 5-10, wherein the plurality of cytokines comprises IL-2, IL-7, IL-15 and IL-21.

12. The method of embodiment 11, wherein the IL-2 is present in the initial co-culture medium at a concentration of at least about 500 IU/mL.

13. The method of any one of embodiments 1-3 and 5-12, wherein the immune checkpoint inhibitor is an anti-PD-1 antibody.

14. The method of embodiment 13, wherein the anti-PD-1 antibody is present in the initial co-culture medium at a concentration of at least about 10 μg/mL.

15. The method of any one of embodiments 10-14, wherein the anti-CD3 antibody is added to the co-culture at about 3 to 7 days after the co-culturing starts.

16. The method of any one of embodiments 1-3 and 5-15, wherein the anti-CD3 antibody is added to the co-culture at about 5 days after the co-culturing starts.

17. The method of any one of embodiments 1-16, wherein the population of dendritic cells loaded with the plurality of tumor antigen peptides and the population of T cells are co-cultured for at least about 10 days in the presence of the anti-CD3 antibody.

18. The method of any one of embodiments 1-17, wherein the population of T cells is present in a population of PBMCs.

19. The method of any one of embodiments 1-18, wherein the population of dendritic cells is obtained by inducing differentiation of a population of monocytes from PBMCs.

20. The method of any one of embodiments 1-19, wherein the population of dendritic cells and the population of T cells are obtained from the same individual.

21. The method of any one of claims 1-20, wherein the plurality of tumor antigen peptides comprises a neoantigen peptide, optionally wherein the plurality of tumor antigen peptides consists of neoantigen peptides.

22. The method of any one of embodiments 1-21, wherein the plurality of tumor antigen peptides is a plurality of synthetic tumor antigen peptides.

23. The method of any one of embodiments 1-22, wherein the plurality of tumor antigen peptides is not obtained from a cell sample.

24. An isolated population of activated T cells prepared using the method of any one of embodiments 1-23.

25. A method of treating a cancer in an individual, comprising administering to the individual an effective amount of the activated T cells of embodiment 24.

26. The method of embodiment 25, further comprising administering to the individual an effective amount of dendritic cells loaded with the plurality of tumor antigen peptides.

27. The method of embodiment 26, wherein the population of dendritic cells and the population of T cells are obtained from the individual being treated.

28. The method of any one of embodiments 25-27, wherein the activated T cells are administered to the individual for at least three times.
29. The method of any one of embodiments 25-28, wherein the activated T cells are administered intravenously.
30. The method of any one of embodiments 25-29, wherein the dendritic cells loaded with the plurality of tumor antigen peptides are administered for at least three times.
31. The method of any one of embodiments 25-30, wherein the dendritic cells loaded with the plurality of tumor antigen peptides are administered subcutaneously, intradermally or intravenously.
32. The method of any one of embodiments 25-31, wherein the cancer is a solid cancer.
33. The method of embodiment 32, wherein the solid cancer is selected from the group consisting of hepatocellular carcinoma, gastric cancer, bladder cancer, soft tissue sarcoma, colorectal cancer, endometrial cancer, and lung cancer.
34. The method of any one of embodiments 25-33, wherein the individual is a human individual.
35. A composition comprising the activated T cells of embodiment 24 for treating a cancer in an individual.
36. Use of the activated T cells of embodiment 24 in the preparation of a medicament for treating a cancer in an individual.

EXAMPLES

The examples below are intended to be purely exemplary of the present application and should therefore not be considered to limit the invention in any way. The following examples and detailed description are offered by way of illustration and not by way of limitation.

Example 1: Optimized DC Maturation Media

Experimental Methods

Peripheral blood mononuclear cells (PBMCs) from healthy volunteers were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed by multiple tumor antigens peptide pool (1 μg/mL/peptide), followed by incubation in a DC maturation medium for 2 days to differentiate into mature DCs.

The cell culture was subject to flow cytometry to determine the number of mature DCs (CD11C+ cells) and subpopulations thereof that expressed various co-stimulatory molecules. The number of mature DCs was normalized to the total number of cells. The number of cells in each DC subpopulation was normalized to the total number of mature DCs. Antibodies for dendritic cell surface staining were obtained from BD Biosciences (anti-human CD86-FITC, CD40-FITC, CD11C-PE, CCR7-FITC, PD-L1-FITC, HLA-DR-FITC). Flow cytometry was performed using FACS CantoII (BD Biosciences) flow cytometers and data was analyzed with the Flowjo program.

Cytokine secretion by mature DCs was assessed by ELISA. The supernatants of mature DCs were centrifuged to remove particulate debris and stored at −80° C. until use. IL-12p70 and IL-10 secretion levels were measured by specific ELISA kits (eBioscience) according to the manufacturer's protocols. TNF-α secretion level was determined using Procarta Plex Multiplex Immunoassays (Affymetrix).

Effects of Different TLRs

The antigen-loaded immature DCs were incubated in DC maturation media comprising different Toll-like receptors (TLRs): DC3/4 indicates a DC maturation medium from a previously reported exemplary MASCT method, including IL6, TNFα, IL1β, and Poly I:C; M+I medium, comprising MPLA ("M") and INFγ ("I"); I+P+R medium, comprising INFγ, Poly I:C ("P''") and resquimod ("R"); M+I+G medium, comprising MPLA, INFγ and gardiquimod ("G"); M+I+P medium, comprising MPLA, INFγ, and Poly I:C; and M+I+C medium, comprising MPLA, INFγ, and CL075. In the situation where two DC maturation media contain the same ingredient, the concentration of that ingredient was identical in the two DC maturation media.

Figure 1B:
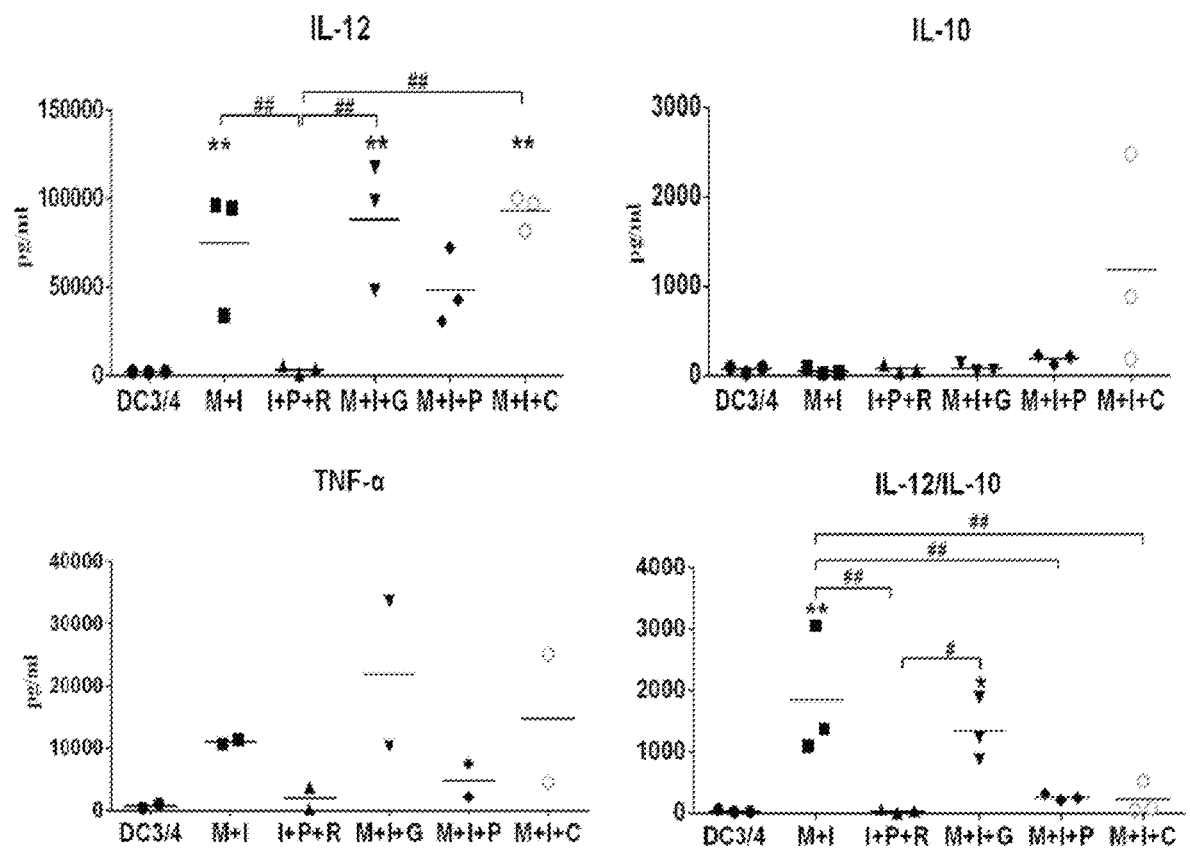
FIG. 1B shows secretion levels of cytokines by mature DCs. DC3/4: a DC maturation medium comprising IL6, TNFα, IL1β, and Poly I:C; I: INFγ; M: MPLA; P: Poly I:C; R: resquimod; G: gardiquimod; C: CL075.

As shown in FIG. 1A, different TLRs and combinations thereof did not have significant impact on the expression of co-stimulatory molecules on mature DCs. However, as shown in FIG. 1B, M+I and M+I+G media led to significantly increased secretion levels of IL12 and TNFα by the mature DCs.

Effects of TLRs at Different Concentrations

The antigen-loaded immature DCs were incubated in DC maturation media comprising TLRs at different concentrations: DC3/4 indicates a DC maturation medium from a previously reported exemplary MASCT method, including IL6, TNFα, IL1β, and Poly I:C; I+M medium, comprising INFγ and a low concentration of MPLA; I+M2 medium, comprising INFγ and a high concentration of MPLA; I+M+G1 medium, comprising MPLA, INFγ and a low concentration of gardiquimod; I+M+G2 medium, comprising MPLA, INFγ and a high concentration of gardiquimod; I+M+R1 medium, comprising MPLA, INFγ and a low concentration of resquimod; I+M+R2 medium, comprising MPLA, INFγ and a high concentration of resquimod; I+M+CL1 medium, comprising MPLA, INFγ, and a low concentration of CL075; and I+M+CL2 medium, comprising MPLA, INFγ, and a high concentration of CL075. The concentration of M was between 1 μg/mL and 10 μg/mL. The concentration of gardiquimod was between 1 μg/mL and 10 μg/mL. The concentration of resquimod was between 1 μg/mL and 10 μg/mL. The concentration of CL075 was between 1 μg/mL and 5 μg/mL.

Figure 2A:
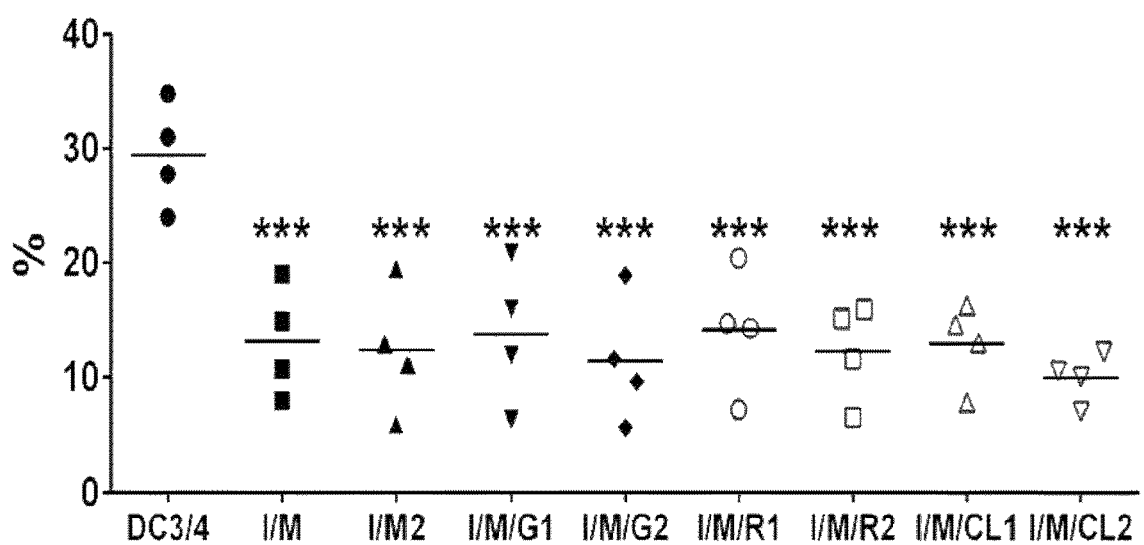
FIG. 2A shows numbers of mature DCs after incubation in DC maturation media containing TLRs at different concentrations.
Figure 2B:
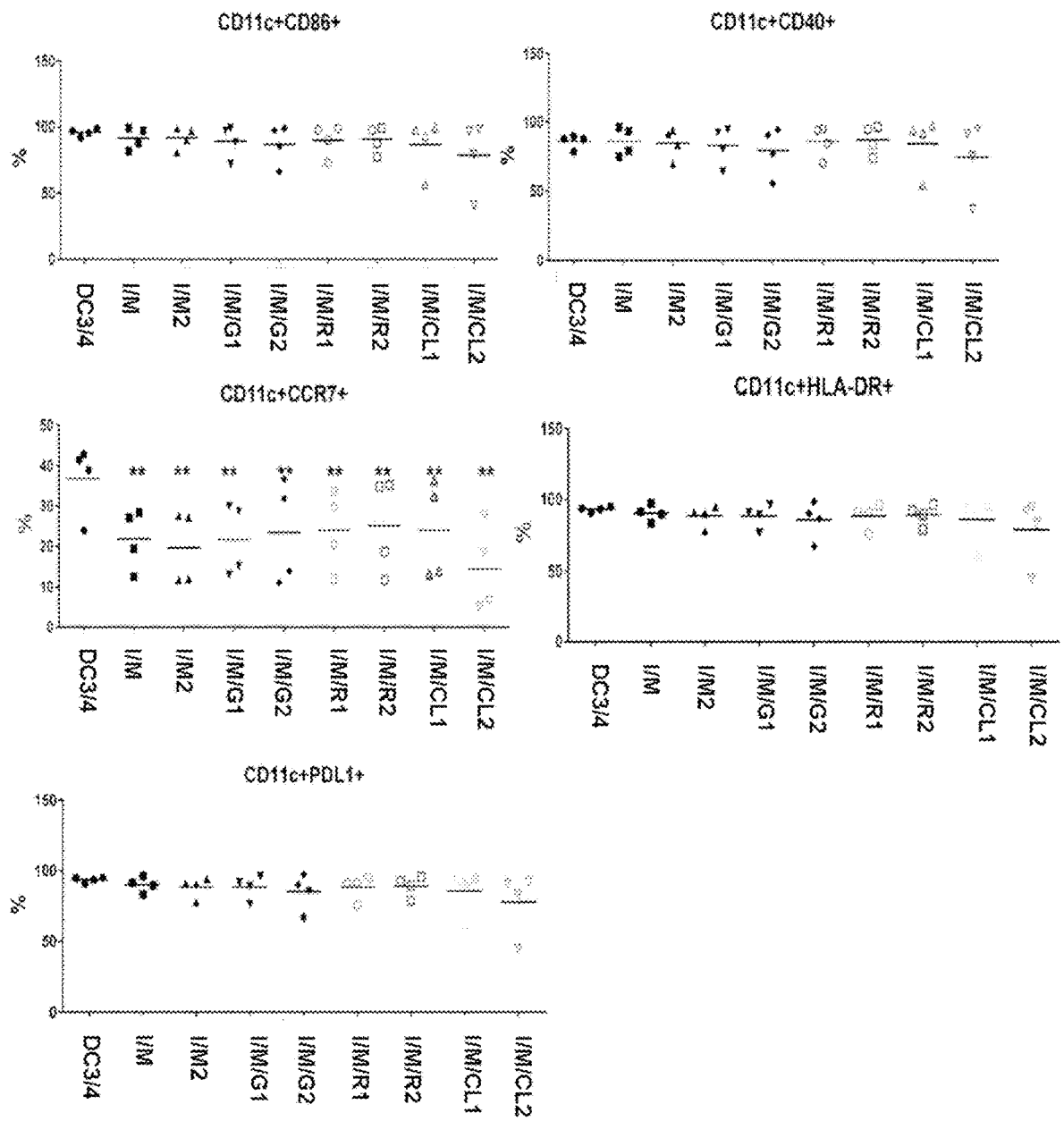
FIG. 2B shows expression levels of co-stimulatory molecules on mature DCs.
Figure 2C:
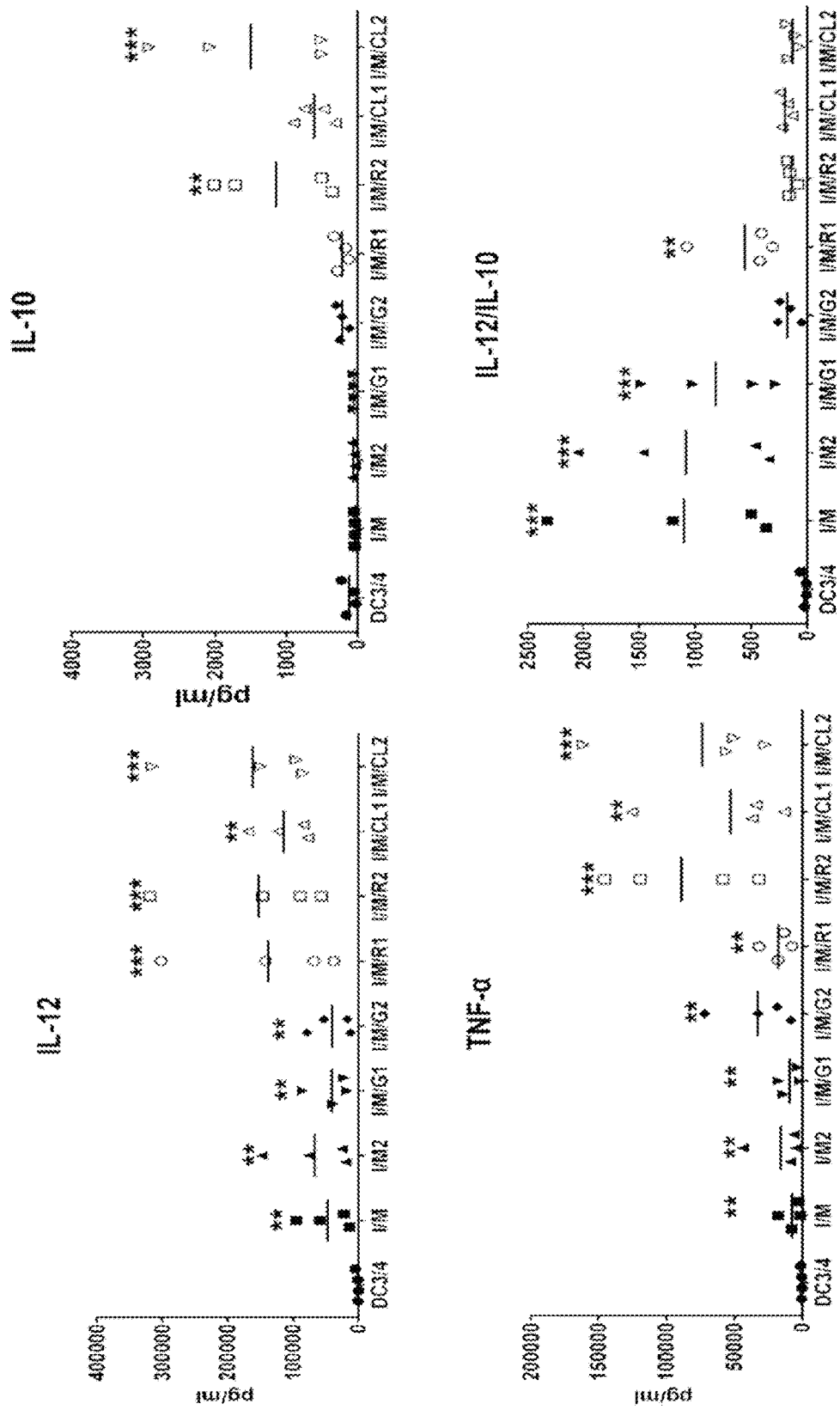
FIG. 2C shows secretion levels of cytokines by mature DCs. DC3/4: a DC maturation medium comprising IL6, TNFα, IL1β, and Poly I: C; I: INFγ; M1: MPLA, low concentration; M2: MPLA, high concentration; R1: resquimod, low concentration; R2: resquimod, high concentration; G1: gardiquimod, low concentration; G2: gardiquimod, high concentration; CL1: CL075, low concentration; CL2: CL075, high concentration.

As shown in FIG. 2A, the DC3/4 medium resulted in a higher number of mature DCs. However, as shown in FIG. 2B, the various DC maturation media did not result in significant difference in the expression of co-stimulatory molecules on the mature DCs. As shown in FIG. 2C, the I+M, I+M1, and I+M+G1 media significantly increased the IL12/IL10 ratio by the mature DCs. The DC maturation media ranked from the highest efficacy to lowest efficacy for induction of DC maturation are as follows: I+M>I+M+G1>I+M+R1.

Effects of PGE2

The antigen-loaded immature DCs were incubated in DC maturation media comprising MPLA, INFγ, and different concentrations of PGE2: DC3/4 indicates a DC maturation medium from a previously reported exemplary MASCT method, including IL6, TNFα, IL1β, and Poly I:C; M+I medium, comprising INFγ and MPLA, but no PGE2; M+I+P1 medium, comprising INFγ, MPLA, and a low concentration of PGE2; M+I+P2 medium, comprising INFγ, MPLA, and a medium concentration of PGE2; M+I+P3 medium, comprising INFγ, MPLA, and a high concentration of PGE2. The concentration of PGE2 was between 0.1 μg/mL and 5 μg/mL.

Figure 3A:
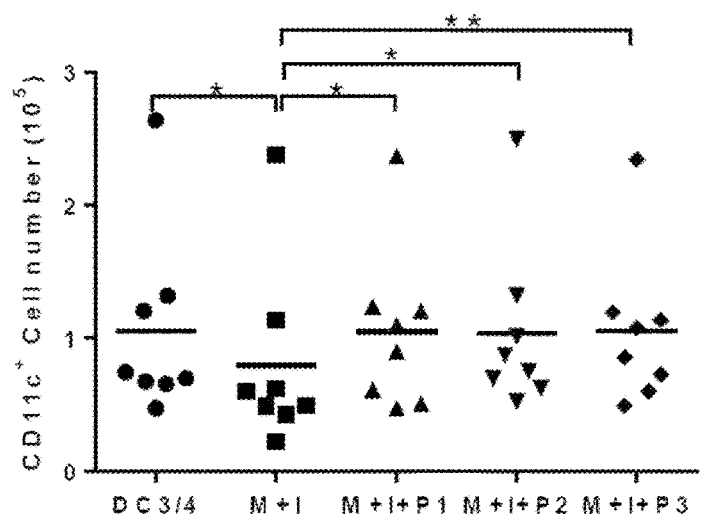
FIG. 3A shows numbers of DCs after induction of maturation by Toll-like receptor (TLR) compositions having different PGE2 concentrations.
Figure 3B:
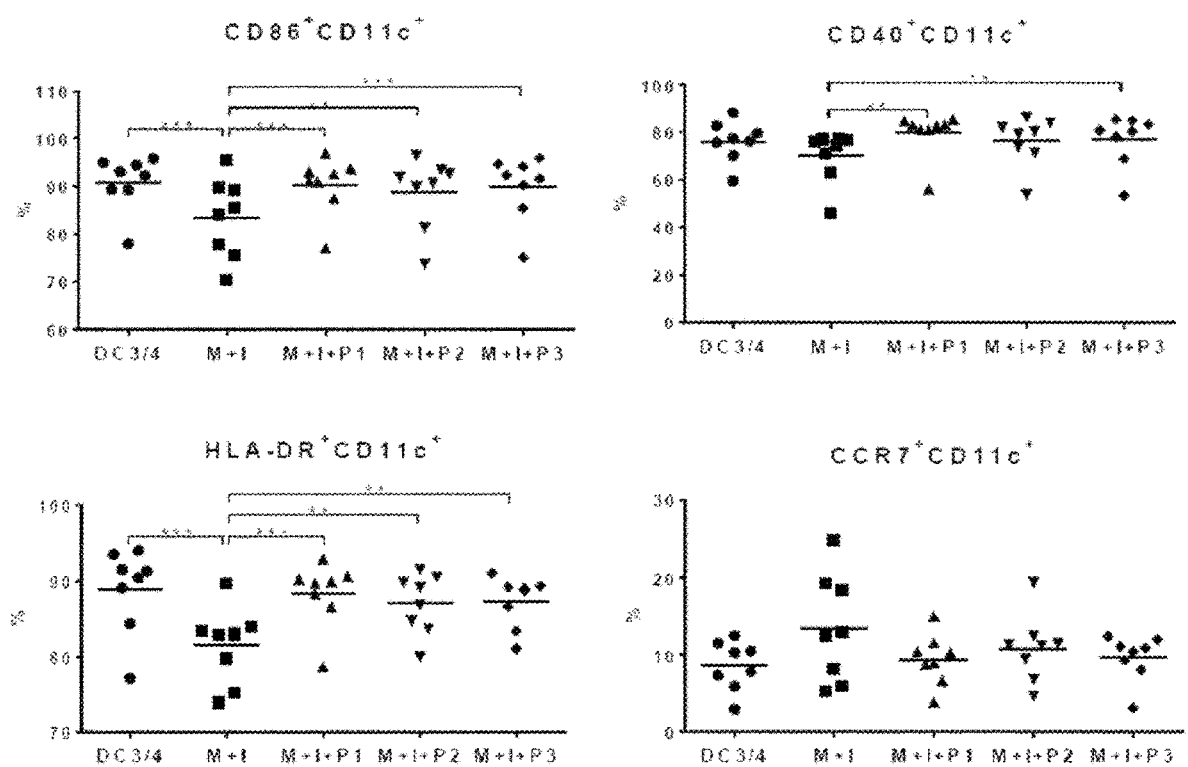
FIG. 3B shows secretion levels of co-stimulatory molecules on induced antigen-loaded mature DCs.
Figure 3C:
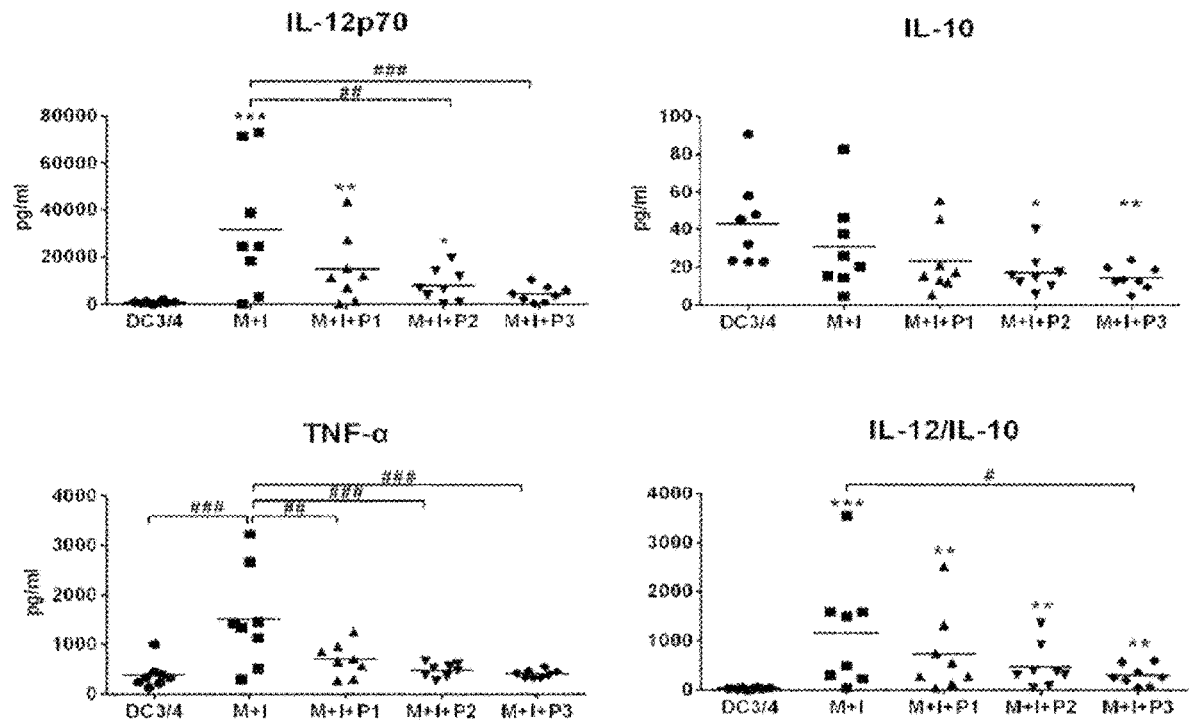
FIG. 3C shows expression levels of cytokines by induced antigen-loaded mature DCs. DC3/4: a DC maturation medium comprising IL6, TNFα, IL1β, and Poly I:C; I: INFγ; M: MPLA; P1: PGE2, low concentration; P2: PGE2, medium concentration; P3: PGE2, high concentration.

The effects of the DC maturation media on induction of DC maturation are shown in FIGS. 3A-3C, and summarized below in Table 1. The DC maturation medium having the highest efficacy on induction of DC maturation is M+I+P1.

TABLE 1

Effects of PGE2 on DC maturation

| Parameter | DC3/4 | M + I | M + I + P1 | M + I + P2 | M + I + P3 |
|---|---|---|---|---|---|
| Number of DCs | 2 | 1 | 2 | 2 | 2 |
| Expression of co-stimulatory molecules on DCs | 2 | 1 | 3 | 2 | 3 |
| Secretion of IL-12 | 1 | 3 | 3 | 2 | 1 |
| Total | 5 | 5 | 8 | 6 | 6 |

Example 2: Optimized Co-Culturing Conditions

Effects of Cytokine Cocktail

Thawed T cells from a frozen stock were mixed with antigen-loaded mature DCs prepared in Example 1 in an initial co-culture medium (AIM-V medium) to provide a co-culture. The initial co-culture medium contained either IL-2 or an interleukin cocktail (including IL-2, IL-7, IL-15 and IL-21), and an anti-PD-1 antibody SHR-1210 (Jiangsu Hengrui). The co-culture was cultured for 19 days.

To determine the proliferation of tumor antigen-specific T cells, FACS analysis was performed as described in the Click-iT EdU Alexa Fluor 488 Flow Cytometry Assay Kit (Invitrogen). IFNγ production of tumor antigen-specific T cells was detected by intracellular cytokine staining and FACS analysis. Anti-human CD3-PE antibody for cell surface staining and anti-human IFN-γ-APC antibody for intracellular cytokine staining were obtained from BD Biosciences. Intracellular cytokine staining was performed by fixing and permeabilizing cells with cytofix/cytoperm (BD Biosciences). Flow cytometry was performed using FACS CantoII (BD Biosciences) flow cytometers and data was analyzed with the Flowjo program.

Figure 4:
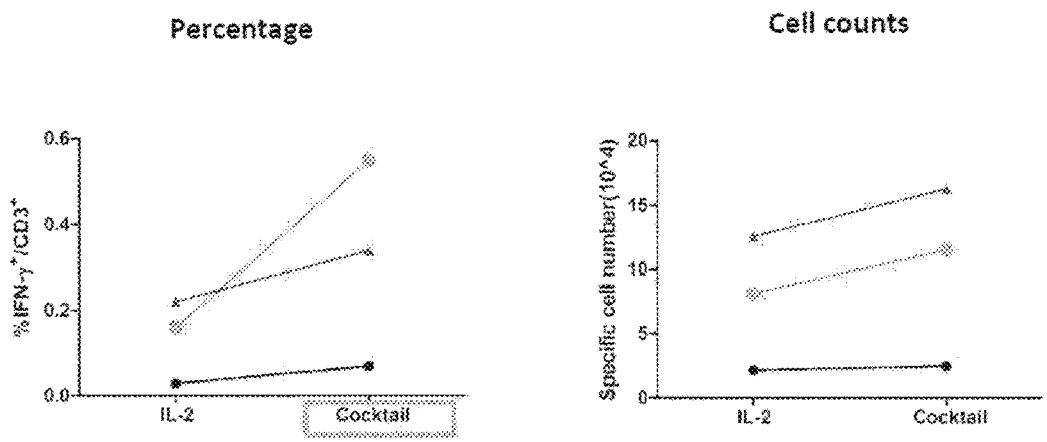
FIG. 4 shows percentages and numbers of tumor antigen-specific T cells, which secreted IFNγ after tumor antigen peptides stimulation, in the co-cultures of antigen-loaded mature DCs and T cells supplemented with IL-2 or an interleukin cocktail (IL-2, IL-7, IL-15 and IL-21).

FIG. 4 shows results from co-culture using DCs and T cells from PBMC samples of three healthy donors. Compared to an initial co-culture medium having IL-2 alone, an initial co-culture medium having an interleukin cocktail yielded higher level of proliferation and percentage of IFNγ-secreting tumor antigen-specific T cells in the co-culture.

Effects of Anti-PD-1, IL-2 and Anti-CD3 Antibody

Thawed T cells from a frozen stock were mixed with antigen-loaded mature DCs prepared in Example 1 in an initial co-culture medium (AIM-V medium) to provide a co-culture. The co-culture was subject to various conditions as shown in Table 2 below. For example, initial co-culture media with or without anti-PD-1 antibody SHR-1210 (Jiangsu Hengrui), with a low concentration or high concentration of IL-2 (rIL-2; R&D Systems, Minneapolis, Minn.), and addition of an anti-CD3 antibody (eBioscience, San Diego, Calif.) to the co-culture after 3 days or 5 days from the start of the co-culture were tested. The DCs and T cells were co-cultured for a total of 19 days. The numbers of tumor-antigen specific T cells and percentages of IFNγ-secreting T cells in the co-culture were determined as described above.

TABLE 2

Co-culturing conditions.

| Conditions | Anti-PD1 | Interleukin cocktail (− IL-2) | IL-2 low | IL-2 high | Anti-CD3 Add at 3 days | Anti-CD3 Add at 5 days |
|---|---|---|---|---|---|---|
| CIK | − | − | | | + | + |
| Previous MASCT | − | − | | | + | + |
| 1 | + | + | | | + | + |
| 2 | + | + | | | + | + |

Figure 5A:
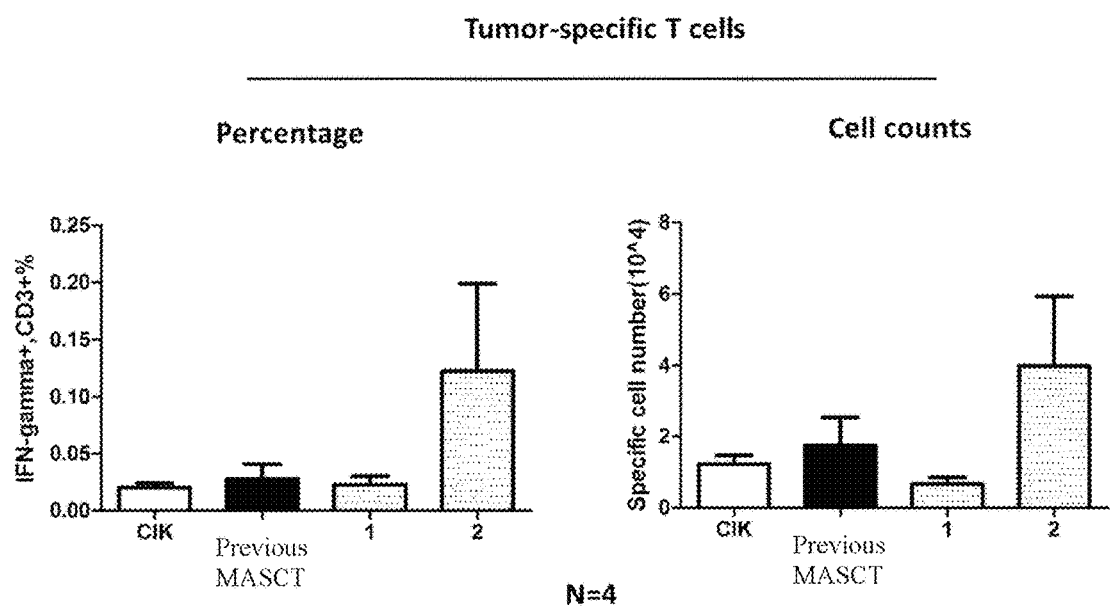
FIG. 5A shows percentages and numbers of tumor antigen-specific T cells in cell preparations under various conditions. CIK: PBMCs cultured with a high concentration of IL-2, and an anti-CD3 antibody was added after 3 days of co-culturing; previous MASCT: co-culture of antigen-loaded DCs and PBMCs with a high concentration of IL-2, and an anti-CD3 antibody was added after 3 days of co-culturing; 1: co-culture of antigen-loaded DCs and PBMCs with an anti-PD1 antibody, an interleukin cocktail (including a high concentration of IL-2), and an anti-CD3 antibody added after 3 days of co-culturing; 2: co-culture of antigen-loaded DCs and PBMCs with an anti-PD1 antibody, an interleukin cocktail (including a high concentration of IL-2), and an anti-CD3 antibody was added after 5 days of co-culturing.

The "CIK" condition resembles a standard condition for preparing cytokine-induced killer cells, except the anti-CD3 antibody was added 3 days after the co-culture started. The "previous MASCT" condition resembles an exemplary condition for preparing activated T cells as disclosed previously in WO2016145578A1, except the anti-CD3 antibody was added 3 days after the co-culture started. As shown in FIG. 5A, condition 2 yielded the highest number of tumor antigen-specific T cells, and highest percentage of IFNγ-secreting T cells in the co-culture.

Effects of Different Concentrations of IL-2

Thawed T cells from a frozen stock were mixed with antigen-loaded mature DCs prepared in Example 1 in an initial co-culture medium (AIM-V medium) to provide a co-culture. The initial co-culture media contained an anti-PD-1 antibody SHR-1210 (Jiangsu Hengrui), interleukin cocktail, a low concentration or high concentration of IL-2 (rIL-2; R&D Systems, Minneapolis, Minn.), and addition of an anti-CD3 antibody (eBioscience, San Diego, Calif.) to the co-culture after 3 days or 5 days from the start of the co-culture. The DCs and T cells were co-cultured for a total of 19 days. The concentration of IL-2 was between 100 IU/mL and 1000 IU/mL. The number of tumor-antigen specific T cells, and percentage of IFNγ-secreting T cells in the co-culture were determined as described above.

Figure 5B:
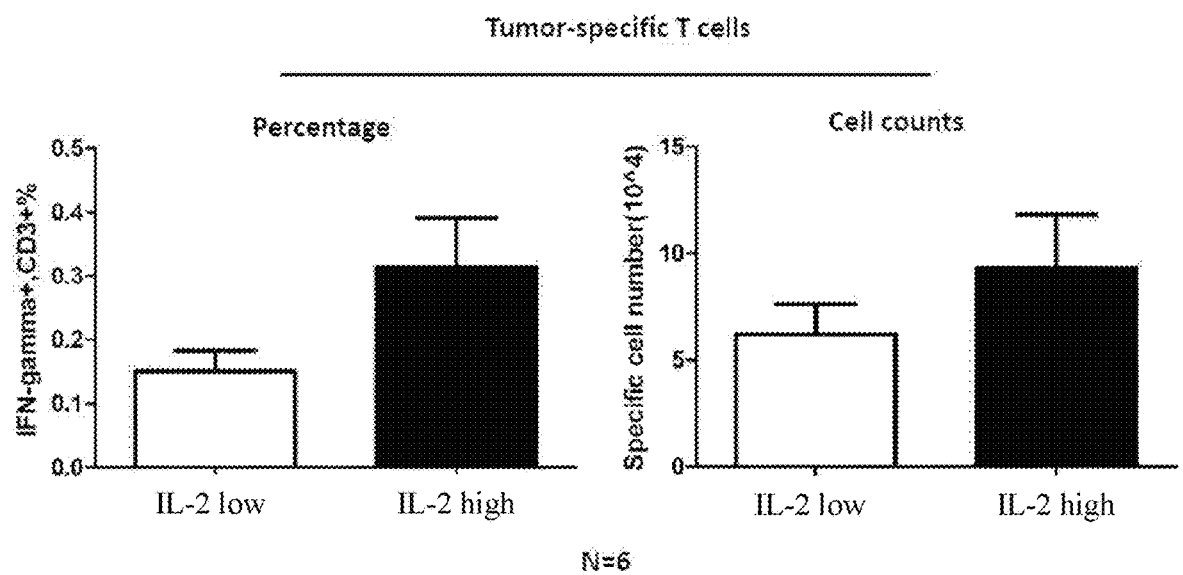
FIG. 5B shows percentages and numbers of tumor antigen-specific T cells in co-cultures of antigen-loaded DCs and PBMCs with an anti-PD1 antibody, an interleukin cocktail (including a low concentration or a high concentration of IL-2), and an anti-CD3 antibody was added after 5 days of co-culturing.

As shown in FIG. 5B, compared to a low concentration of IL-2, a high concentration of IL-2 yielded a higher number of tumor antigen-specific T cells, and a higher percentage of IFNγ-secreting T cells in the co-culture.

Example 3: Comparison of Exemplary Improved MASCT and Previous MASCT Cell Preparation Methods This example provides a head-to-head comparison of immune cells prepared using exemplary cell preparation methods described in the present application ("improved MASCT protocol") versus exemplary cell preparation methods disclosed in WO2016145578A1 ("previous MASCT protocol").

Effects on IL-12 Secretion by Mature DCs

Peripheral blood mononuclear cells (PBMCs) from healthy volunteers and cancer patients were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed by multiple tumor antigens peptide pool (1 μg/mL/peptide), followed by incubation in either "improved MASCT" DC maturation medium or "previous MASCT" DC maturation medium for two days to differentiate into mature DCs. The improved MASCT DC maturation medium comprises IFN-γ, MPLA, and PGE2. The previous MASCT DC maturation medium comprises IL-6, TNF-α, IL-1β, POLY(I:C) and PGE2. IL-12p secretion levels from the mature DCs were determined.

Cytokine secretion by mature DCs was assessed by ELISA. As shown in FIGS. 6A-6B, DCs induced by the improved MASCT DC maturation medium secreted significantly higher levels of IL-12p70 than DCs induced by the previous MASCT DC maturation medium. Notably, using PBMCs from cancer patients, the improved MASCT DC maturation medium led to more than 70 fold increase in the IL-12p70 secretion level than the previous MASCT DC maturation medium. This increase in IL-12 secretion was more pronounced with DCs derived from cancer patients than DCs derived from healthy volunteers. The enhanced cytokine secretion level by mature DCs prepared using the improved MASCT DC maturation medium increased the cytotoxicity of DCs against solid tumors.

Effects on Tumor-Specific T Cells

T cells and antigen-loaded mature DCs derived from PBMCs of healthy volunteers (n=5) were co-cultured according to an exemplary improved MASCT protocol or an exemplary previous MASCT protocol. The improved MASCT protocol involved co-culturing T cells with antigen-loaded mature DCs in an initial co-culture medium containing an interleukin cocktail (including IL-2, IL-7, IL-15 and IL-21), and an anti-PD-1 antibody SHR-1210 (Jiangsu Hengrui). The co-culture was incubated for 5 days when an anti-CD3 antibody was added to the co-culture. The cells were co-cultured for a total of 19 days to provide activated T cells. The previous MACT protocol involved co-culturing T cells with antigen-loaded mature DCs in a co-culture medium containing IL-2 and an anti-CD3 antibody. The cells were co-cultured for a total of 19 days to provide activated T cells.

IFNγ production by the activated T cells in response to tumor antigens was detected by intracellular cytokine staining and FACS analysis as described in Example 2. As shown in FIG. 7, the percentage of IFNγ-producing activated T cells in the co-culture increased significantly (about 2-4 times) using the improved MASCT protocol compared to that using the previous MASCT protocol.

Anti-tumor effects of the activated T cells prepared using the improved MASCT protocol and the previous MASCT protocol was determined using various solid tumor cell lines, including MBA231 (breast cancer cells), CNE1 (nasopharyngeal carcinoma cells), HepG2 (liver carcinoma cells) and Saos-2 (osteosarcoma cells). Briefly, tumor cells were cultured in DMEM supplemented with 10% inactivated fetal bovine serum, 100 U/mL penicillin, 100 μg/mL streptomycin, Glutamax, MEM NEAA, (Gibico, Carlsbad, Calif.). Tumor cells were washed with D-PBS (Invitrogen) and co-cultured with the activated T cells at a T cells: target (T: Target) ratio of 1:10 or 1:30 in 96-well round-bottom plates in triplicates in AIM-V for 4 hours. Cytotoxicity was shown as the percentage of maximal LDH released after lysis and measured by the Cytotox 96 Assay kit (Promega G1780, Canada).

Figure 8:
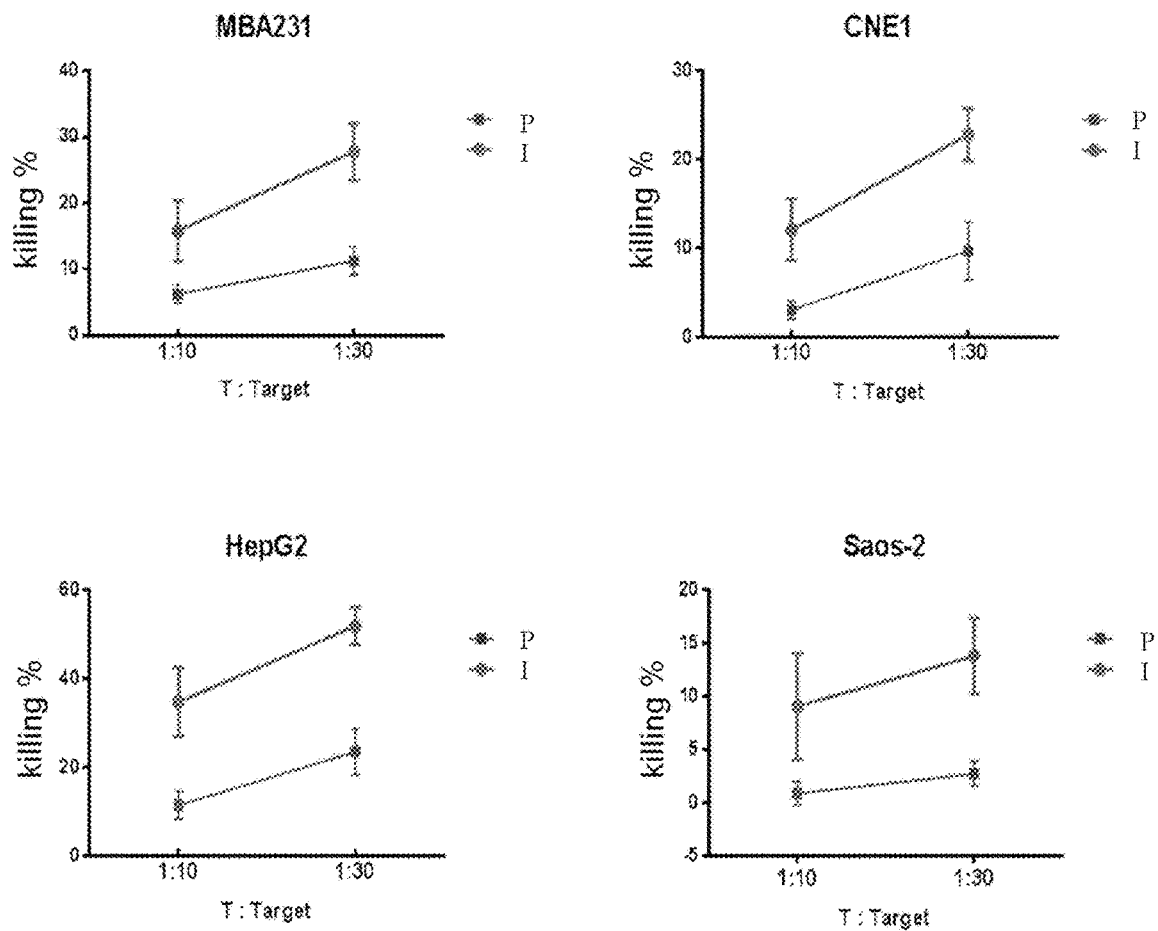
FIG. 8 shows anti-tumor effects of activated T cells prepared using a previous MASCT protocol ("P") or an improved MASCT protocol ("I").

As shown in FIG. 8, activated T cells prepared using the improved MASCT protocol had significantly enhanced cytotoxicity against all four types of tumor cells lines, compared to activated T cells prepared using the previous MASCT protocol.

Example 4: Improved MASCT Clinical Study

The improved MASCT study is an open-label, multi-center study that aims to investigate the safety and efficacy of an embodiment of the improved MASCT method in treating patients having solid tumors, including hepatocellular carcinoma, gastric cancer, bladder cancer, soft tissue sarcoma, endometrial cancer, colorectal cancer, and lung cancer. Enrolled patients may have previously received curative resection, such as resection or RFA, or first-line chemotherapy.

Patients receive one or more cycles of improved MASCT treatment. For example, patients may receive one cycle of improved MASCT treatment every 1-3 months for 1-2 years. In each cycle of improved MASCT treatment, PBMCs are obtained from each patient. Immature dendritic cells are obtained from the PBMCs. On day 1, immature dendritic cells are pulsed with a pool of antigen peptides, including up to 44 antigen peptides derived from hTERT, p53, Survivin, NY-ESO-1, CEA, CCND1, MUC1, Her2, MAGEA1, MAGEA3, WT-1, RGS5, VEGFR1, VEGFR2, CDCA1, HBcAg, HBV polymerase, GPC3, SSX, and AFP. The pool of antigen peptides may also contain up to 10 antigen peptides derived from neoantigens. The immature dendritic cells loaded with the pool of antigen peptides are cultured in a DC maturation medium containing IFN-γ, MPLA, and PGE2 to provide mature dendritic cells loaded with the pool of antigen peptides. On day 8, the patient receives subcutaneous injection of the mature dendritic cells loaded with the pool of antigen peptides. From day 8 to day 13, T cells in PBMCs and mature dendritic cells loaded with the pool of antigen peptides are co-cultured in the presence of a cytokine cocktail (IL-2, IL-7, IL-15, IL-21) and anti-PD-1 antibody (e.g., SHR-1210). On day 13, anti-CD3 antibody (e.g., OKT-3) is added to the co-culture. On day 28, the co-culture containing activated T cells are infused to the patient. In the combination therapy group, patients received anti-PD-1 antibody treatment or chemotherapy treatment.

Each patient receives improved MASCT treatment for up to 18 cycles unless the patient experiences disease progression or unacceptable toxicity. Patients are followed for about 2.5 years or until death or disease progression of all patients, whichever occurs earlier.

Patients must fulfill all of the following criteria to be eligible for admission to the study.

1. The patient is diagnosed with solid tumors, including hepatocellular carcinoma, gastric cancer, bladder cancer, soft tissue sarcoma, endometrial cancer, colorectal cancer, and NSCLC;
2. At least one measurable lesion as defined by RECIST criteria 1.1 for solid tumors;
3. No cancer embolus in the main portal vein, first branch of hepatic duct, first branch of hepatic vein, or inferior vena cava;
4. ECOG Performance status (ECOG-PS) ≤2;
5. The expected survival time is more than 6 months;
6. Tests of blood, liver and kidney meeting the following criteria:
    a. WBC>3×10$^9$/L
    b. Neutrophil counts >1.5×10$^9$/L
    c. Hemoglobin ≥85 g/L
    d. Platelet counts ≥50×10$^9$/L
    e. PT is normal or The extend time <3 s
    f. BUN≤1.5 times the upper-limit,
    g. Serum creatinine ≤1.5 times of the upper-limit
7. Patient consent obtained and signed according to local Institutional and/or University Human Experimentation Committee requirements and/or a central Institutional Review Board (IRB) or other as appropriate.

Patients who meet any of the following criteria are not eligible for admission to the study:

1. Women who are pregnant or during breast feeding or plan to be pregnant within 2 years;
2. Known active brain metastases as determined by CT or MRI evaluation;
3. Know the period of systemic and continuous use of immunomodulatory agents (such as interferon, thymosin, traditional Chinese medicine) within 6 months;
4. Positive for HIV antibody or HCV antibody;
5. Have a history of immunodeficiency disease or autoimmune diseases (such as rheumatoid arthritis, Buerger's disease, multiple sclerosis or diabetes type 1);
6. Patients with organ failure;
7. Patients with serious mental disease;
8. Drug addiction within 1 year before enrollment, including alcoholism;
9. Participated in other clinical trials within 3 months before screening;
10. Other reasons the researchers deem unsuitable for the study.

The primary outcome measures include safety and efficacy of the improved MASCT treatment. Secondary outcome measures include overall survival (OS), progression-free survival (PFS), objective response rate (ORR), complete response (CR), partial response (PR), stable disease rate (SDR), and disease-related biomarker measurements. Tumor response and progression are assessed using RECIST criteria (v1.1). Safety is assessed on the basis of vital signs, clinical laboratory findings, and adverse events graded according to the NCI CTCAE version 4.02. ELISPOT assays are performed to determine antigen peptide-specific response of the activated T cells of each patient in each cycle of the improved MASCT treatment.

Example 5: Immune Response Against Neoantigens by Neo-MASCT-Treated Patients

To investigate whether neoantigens could induce tumor specific immune responses in patients with solid tumor (e.g., HCC, endometrial cancer, and colon cancer), neoantigen stimulating cellular therapy using the improved MASCT preparation protocol ("neo-MASCT") was applied to patients after radical resection.

Figure 9:
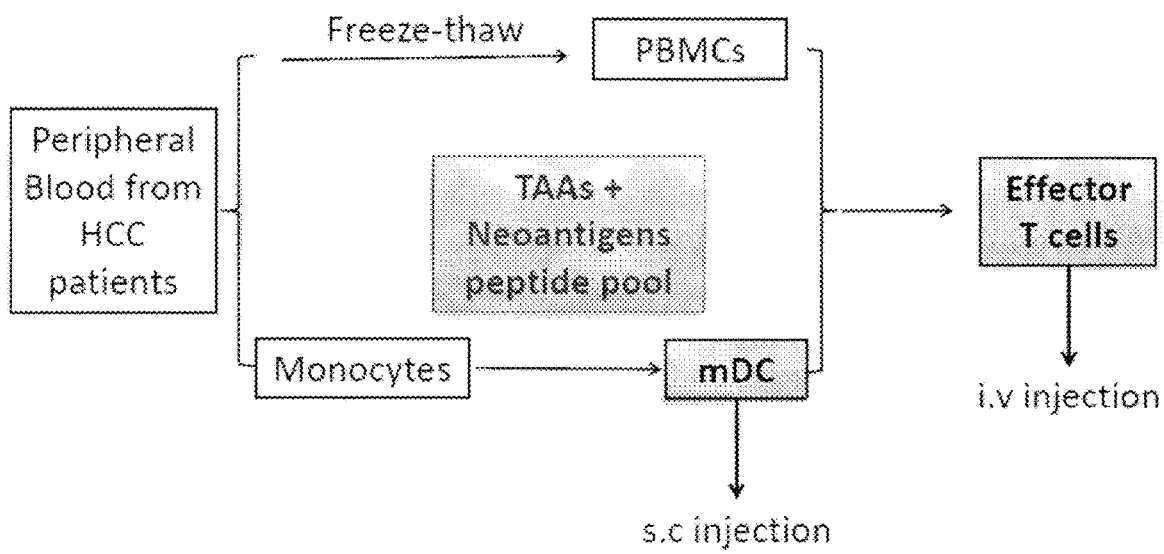
FIG. 9 shows a schematic workflow of an exemplary neo-MASCT treatment. The neo-MASCT treatment shown in this figure uses antigen peptides derived from both neoantigens and tumor-associated antigens (TAA). In some embodiments, the neo-MASCT treatment uses a pool of antigen peptides derived only from neoantigens.

Patients received neo-MASCT treatments according to the clinical protocol described in Example 4. As shown in FIG. 9, in each cycle of neo-MASCT treatment, each patient received injection of mature dendritic cells (DCs) loaded with a peptide pool of multiple shared tumor associated antigens (TAAs) and several personalized neoantigens, followed by infusion of autologous T cells stimulated by these DCs. The shared tumor associated antigens (TAAs) included both general tumor antigens and cancer-type specific tumor antigens. The patients received 1 to 10 cycles of neo-MASCT treatments.

Figure 10:
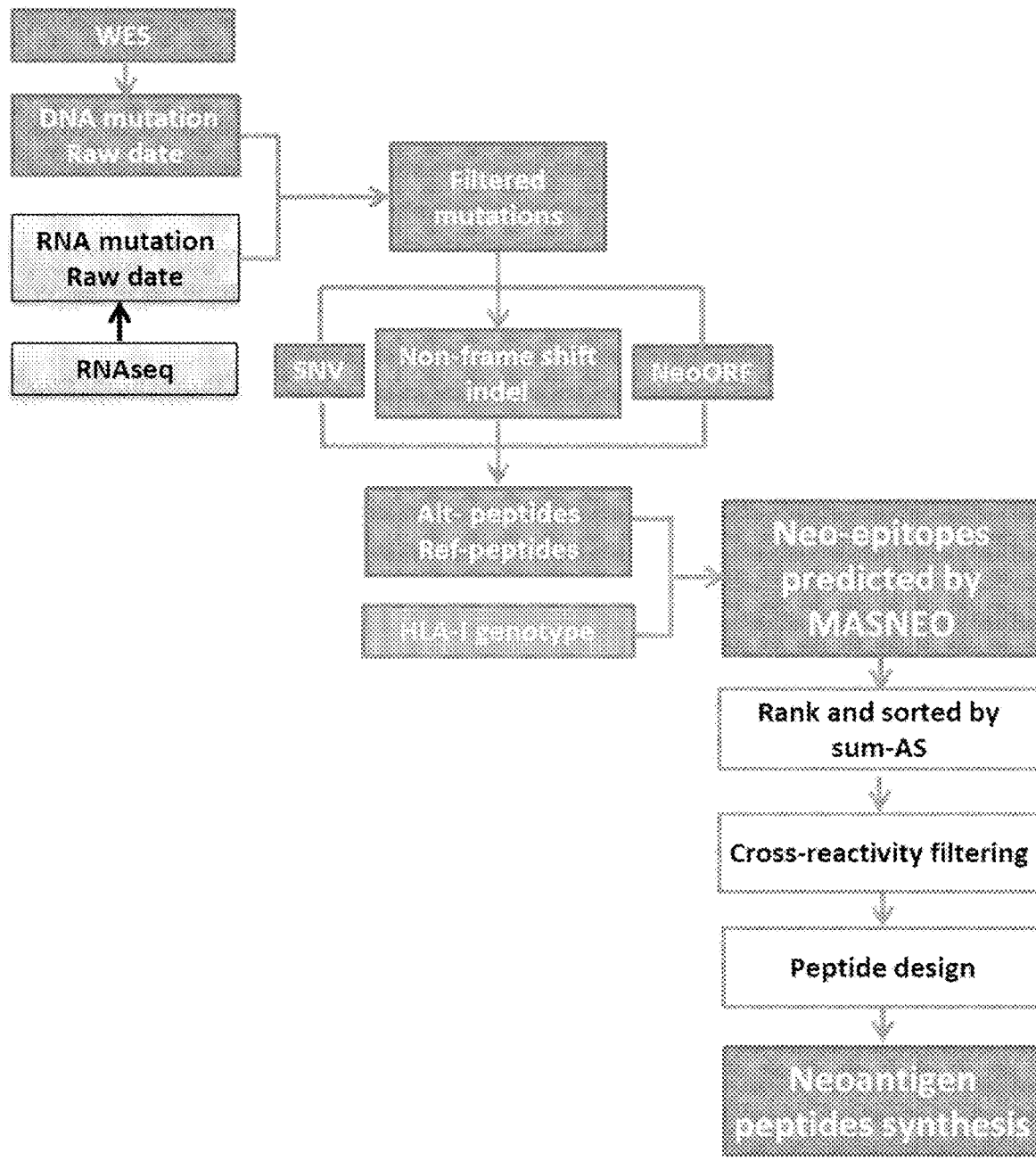
FIG. 10 shows a schematic workflow for designing neoantigen peptides.

FIG. 10 shows a schematic flowchart for designing neoantigen peptides. To obtain neoantigen sequences, fresh tumor samples were acquired immediately after biopsy or surgery for subsequent Whole Exosome Sequencing (WES) and RNAseq. All mutations including SNV, non-frame shift insert/deletion (Indel), and neoORF were detected by comparing the next-generation sequencing data from tumors to normal tissues. All neo-epitope candidates were predicted by the MASNEO™ algorithm according to the patient's HLA class I genotypes. Long neoantigen peptides containing 25-31 amino acids with higher affinities were selected for further synthesis and treatment. Peptides containing multiple neo-epitopes were preferred. A smaller number of neoantigen peptides could be predicted using the NetMHC algorithm (Andreatta M, Nielsen M. *Bioinformatics* (2016) February 15; 32(4):511-7) from the same next-generation sequencing results.

Figure 14:
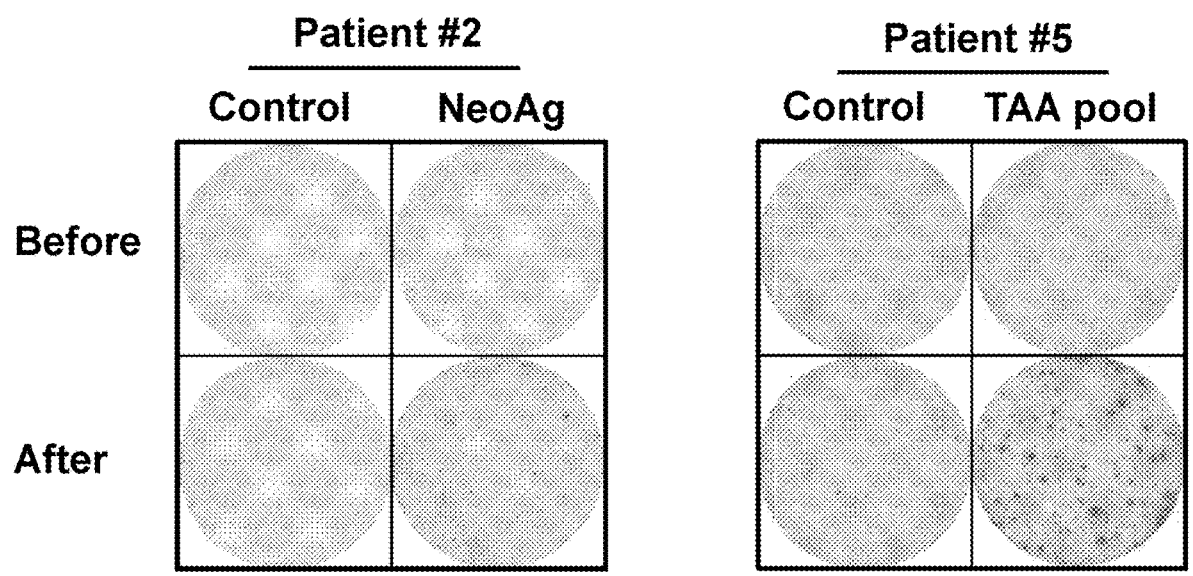
FIG. 14 shows exemplary ELISPOT results of PBMCs from Patient #2 and patient #5 before and after neo-MASCT treatments.

ELISPOT assays were carried out to determine whether the patients developed MHC-restricted T cell response against each of the tumor antigen peptides, including neoantigen peptides. Briefly, PBMCs from patients were plated ($1 \times 10^6$ cells/well) in AIM-V medium without any cytokines on cell culture plate, and further stimulated with individual antigen peptides for 48 h. PBMCs were then transferred onto a 96-well ELISPOT assay plate (U-CyTech Biosciences) for IFNγ detection. PBMCs were further stimulated with peptides for another 16 h. The ELISPOT assay was performed and analyzed according to the manufacturer's instructions. The number of spot-forming units was determined with computer-assisted image analysis software (ChampSpot; Saizhi). The responses were shown as spot-forming units per $10^5$ PBMC/well. Results were demonstrated as an IFNγ-producing fold index compute by specific peptide group: irrelevant peptide group. Exemplary raw ELISPOT results are shown in FIG. 14.

FIG. 11 summarizes the ELISPOT results of eight neoantigen peptide-responding patients, including six HCC patients, one endometrial cancer patient, and one colon cancer patient. Each patient responded to 25% to 100% of the neoantigen peptides as predicted by MASNEO™. An overall response rate of 66% was achieved among the patients using neoantigen peptides predicted by MASNEO™.

Within the HCC patient group, eight HCC patients have received neo-MASCT, and seven of them were tested for specific immune responses against both TAAs and neoantigens using the ELISPOT assay. The results showed that Neo-MASCT induced TAA-specific immune responses in five patients (5/7, 71%), and induced neoantigen-specific immune responses in six patients (6/7, 86%), respectively. One patient (Patient #2) demonstrated specific T cell responses against all five neoantigen peptides (5/5, 100%) after neo-MASCT treatment. The average responsive rate of neoantigens was 65% (22/34 peptides) among the six responding HCC patients.

Figure 12:
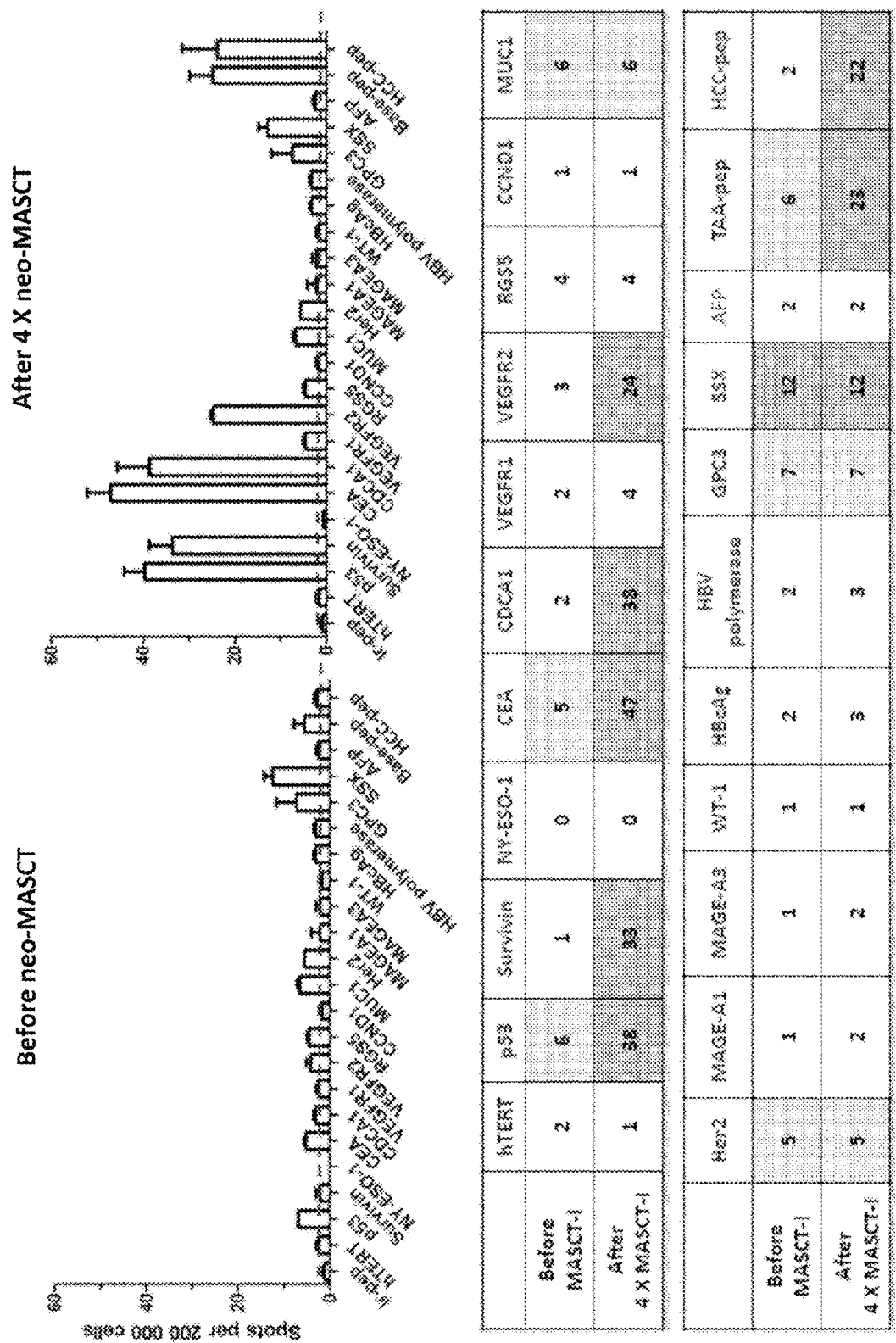
FIG. 12 shows ELISPOT results of PBMCs from Patient #2 before and after improved MASCT treatments.

FIG. 12 shows ELISPOT results using PMBCs from Patient #2 before the neo-MASCT treatment and after four cycles of neo-MASCT treatment. "Base-pep" indicates results using a pool of general tumor antigen peptides, including hTERT, p53, Survivin, NY-ESO-1, CEA, CDCA1, VEGFR1, VEGFR2, RGS5, CCND1, MUC1, Her2, MAGEA1, MAGEA3 and WT-1. "HCC-pep" indicates results using a pool of HCC-specific tumor antigen peptides, including HBcAg, HBV polymerase, GPC3, SSX and AFP. Enhanced T-cell response against the Base-pep pool, the HCC-pep pool, as well as individual tumor antigen peptides (e.g., p53, Survivin, CEA, CDCA1, VEGFR1, VEGFR2, MUC1, Her2, GPC3, and SSC) was observed after the neo-MASCT treatment.

Figure 13:
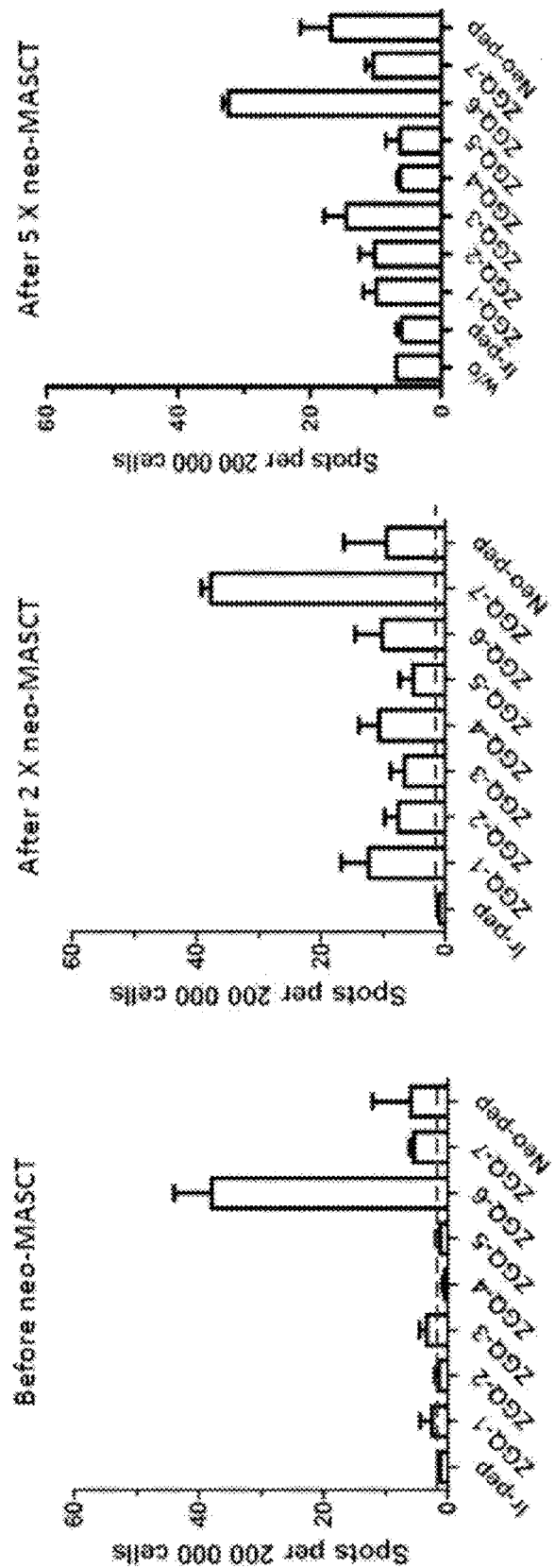
FIG. 13 shows ELISPOT results of PBMCs from Patient #2 before and after neo-MASCT treatments.

FIG. 13 shows ELISPOT results using PMBCs from Patient #2 before the neo-MASCT treatment, after 2 cycles of neo-MASCT treatment, and after 5 cycles of neo-MASCT treatment. "Neo-pep" indicates results using a pool of neoantigen peptides, including ZGQ-1, ZGQ-2, ZGQ-4, ZGQ-5, ZGQ-6 and ZGQ-7. Enhanced T-cell response against the Neo-pep pool and individual neoantigen peptides was observed after multiple rounds of neo-MASCT treatment.

In conclusion, the results demonstrate that neo-MASCT with improved MASCT preparation protocol is well-tolerated in cancer patients and elicits immune responses against multiple tumor antigens, especially personalized neoantigens. The neo-MASCT treatment in this example uses both neoantigen peptides and tumor-associated antigen peptides. In view of the high rate of specific T-cell response to neoantigen peptides, we plan to conduct clinical studies using a pool of neoantigen peptides without any general tumor antigen peptides to prepare activated T cells for neo-MASCT treatments of patients with solid tumors.

What is claimed is:

1. A method of preparing a population of activated T cells, the method comprising:
   a) contacting a population of dendritic cells with a plurality of tumor antigen peptides to obtain a population of dendritic cells loaded with the plurality of tumor antigen peptides;
   b) co-culturing the population of dendritic cells loaded with the plurality of tumor antigen peptides and a population of T cells in an initial co-culture medium comprising a plurality of cytokines and an immune checkpoint inhibitor to provide a co-culture; and
   c) adding an anti-CD3 antibody to the co-culture at 5 days after the co-culturing starts, thereby obtaining the population of activated T cells.

2. The method of claim 1, wherein step a) further comprises culturing the population of dendritic cells loaded with the plurality of tumor antigen peptides in a dendritic cell (DC) maturation medium comprising a toll-like receptor (TLR) agonist.

3. The method of claim 2, wherein the TLR agonist is selected from the group consisting of monophosphoryl lipid (MPLA), Poly I:C, resquimod, gardiquimod, and CL075.

4. The method of claim 1, wherein the plurality of cytokines comprises IL-2, IL-7, IL-15 and IL-21.

5. The method of claim 4, wherein the IL-2 is present in the initial co-culture medium at a concentration of at least about 500 IU/mL.

6. The method of claim 1, wherein the immune checkpoint inhibitor is an anti-programmed cell death protein-1 (PD-1) antibody.

7. The method of claim 6, wherein the anti-PD-1 antibody is present in the initial co-culture medium at a concentration of at least about 10 μg/mL.

8. The method of claim 1, wherein the population of dendritic cells loaded with the plurality of tumor antigen peptides and the population of T cells are co-cultured for at least about 10 days in the presence of the anti-CD3 antibody.

9. The method of claim 1, wherein the plurality of tumor antigen peptides comprises a neoantigen peptide.

10. A method of preparing a population of activated T cells, the method comprising:
   a) contacting a population of dendritic cells with a plurality of tumor antigen peptides to obtain a population of dendritic cells loaded with the plurality of tumor antigen peptides;
   b) culturing the population of dendritic cells loaded with the plurality of tumor antigen peptides in a DC maturation medium comprising MPLA, interferon-$\gamma$ (INF$\gamma$), and prostaglandin E2(PGE2); and
   c) co-culturing the population of dendritic cells loaded with the plurality of tumor antigen peptides and a population of T cells, thereby obtaining the population of activated T cells.

11. The method of claim 10, wherein the INFγ is present in the DC maturation medium at a concentration of at least about 100 IU/mL.

12. The method of claim 10, wherein the MPLA is present in the DC maturation medium at a concentration of at least about 0.5 μg/mL.

13. The method of claim 10, wherein the PGE2 is present in the DC maturation medium at a concentration of at least about 0.1 μg/mL.

14. The method of claim 10, wherein step c) comprises: co-culturing the population of dendritic cells loaded with the plurality of tumor antigen peptides and a population of T cells in an initial co-culture medium comprising a plurality of cytokines and an immune checkpoint inhibitor to provide a co-culture; and adding an anti-CD3 antibody to the co-culture, thereby obtaining the population of activated T cells.

15. The method of claim 14, wherein the anti-CD3 antibody is added to the co-culture at about 3 to 7 days after the co-culturing starts.

16. The method of claim 15, wherein the anti-CD3 antibody is added to the co-culture at about 5 days after the co-culturing starts.

17. A method of treating a cancer in an individual, comprising:
   a) contacting a population of dendritic cells with a plurality of tumor antigen peptides to obtain a population of dendritic cells loaded with the plurality of tumor antigen peptides;
   b) co-culturing the population of dendritic cells loaded with the plurality of tumor antigen peptides and a population of T cells in an initial co-culture medium comprising a plurality of cytokines and an immune checkpoint inhibitor to provide a co-culture;
   c) adding an anti-CD3 antibody to the co-culture at 5 days after the co-culturing starts, thereby obtaining activated T cells; and
   d) administering to the individual an effective amount of the activated T cells.

18. The method of claim 17, wherein step a) further comprises culturing the population of dendritic cells loaded with the plurality of tumor antigen peptides in a DC maturation medium comprising MPLA, interferon-$\gamma$ (INF$\gamma$), and prostaglandin E2 (PGE2).

19. The method of claim 17, further comprising administering an effective amount of the dendritic cells loaded with the plurality of tumor antigen peptides to the individual.

\* \* \* \* \*